(12) United States Patent
Zankel et al.

(10) Patent No.: US 7,829,537 B2
(45) Date of Patent: Nov. 9, 2010

(54) RECEPTOR ASSOCIATED PROTEIN (RAP) CONJUGATES

(75) Inventors: Todd C. Zankel, San Francisco, CA (US); Christopher M. Starr, Sonoma, CA (US)

(73) Assignee: Raptor Pharmaceuticals Inc., Novato, CA (US)

(*) Notice: Subject to any disclaimer, the term of this patent is extended or adjusted under 35 U.S.C. 154(b) by 0 days.

(21) Appl. No.: 12/508,956

(22) Filed: Jul. 24, 2009

(65) Prior Publication Data

US 2010/0028370 A1 Feb. 4, 2010

Related U.S. Application Data

(63) Continuation of application No. 10/812,849, filed on Mar. 30, 2004, now Pat. No. 7,569,544, which is a continuation-in-part of application No. 10/600,862, filed on Jun. 20, 2003, now abandoned.

(51) Int. Cl.
*A61K 38/18* (2006.01)
*A61K 38/30* (2006.01)
*A61K 33/24* (2006.01)

(52) U.S. Cl. ...................................... 514/12; 424/649
(58) Field of Classification Search ........................ None
See application file for complete search history.

(56) References Cited

U.S. PATENT DOCUMENTS

| | | | |
|---|---|---|---|
| 4,018,884 | A | 4/1977 | Cleeland, Jr. et al. |
| 4,391,904 | A | 7/1983 | Litman et al. |
| 4,394,448 | A | 7/1983 | Szoka, Jr. et al. |
| 4,744,981 | A | 5/1988 | Pavanasasivam |
| 4,897,255 | A | 1/1990 | Fritzberg et al. |
| 4,988,496 | A | 1/1991 | Srinivasan et al. |
| 5,106,951 | A | 4/1992 | Morgan, Jr. et al. |
| 5,186,941 | A | 2/1993 | Callahan et al. |
| 5,474,766 | A | 12/1995 | Schwartz et al. |
| 5,604,198 | A | 2/1997 | Poduslo et al. |
| 5,650,391 | A | 7/1997 | Schwartz et al. |
| 5,962,012 | A | 10/1999 | Lin et al. |
| 5,962,266 | A | 10/1999 | White et al. |
| 5,981,194 | A | 11/1999 | Jeffries et al. |
| 6,072,041 | A | 6/2000 | Davis et al. |
| 6,165,476 | A | 12/2000 | Strom et al. |
| 6,261,595 | B1 | 7/2001 | Stanley et al. |
| 6,426,208 | B1 | 7/2002 | Kakkis et al. |
| 6,447,775 | B1 | 9/2002 | Strickland et al. |
| 6,455,494 | B1 | 9/2002 | Jefferies et al. |
| 6,569,661 | B1 | 5/2003 | Qin et al. |
| 6,585,971 | B1 | 7/2003 | Kakkis |
| 6,743,427 | B1 | 6/2004 | Schenk |
| 6,919,311 | B2 | 7/2005 | Lenting et al. |
| 7,122,353 | B2 | 10/2006 | Shen |
| 7,700,554 | B2 * | 4/2010 | Beliveau et al. .............. 514/12 |
| 2001/0025026 | A1 | 9/2001 | Heartlein et al. |
| 2002/0168370 | A1 | 11/2002 | McDonald et al. |
| 2003/0129186 | A1 | 7/2003 | Beliveau et al. |
| 2004/0009906 | A1 | 1/2004 | Kakkis et al. |
| 2007/0083334 | A1 | 4/2007 | Mintz et al. |

FOREIGN PATENT DOCUMENTS

| | | |
|---|---|---|
| WO | WO-00/04926 | 2/2000 |
| WO | WO-00/28021 | 5/2000 |
| WO | WO-00/71714 | 11/2000 |
| WO | WO-01/59459 | 8/2001 |
| WO | WO-02/13843 | 2/2002 |
| WO | WO-03/009815 | 2/2003 |

OTHER PUBLICATIONS

Albeck et al., "A non-invasive transport system for GDNF across the blood-brain barrier", *NeuroReport*, 8:2293-8 (1997).
Altschul et al., "Basic local alignment search tool", *J. Mol. Biol.*, 215:403-10 (1990).
Anderson et al., "Differential binding of ligands to the apolipoprotein E receptor 2," *Biochemistry*, 42:9355-64 (2003).
Anderson et al., "Dominant thermodynamic role of the third independent receptor binding site in the receptor-associated protein RAP," *Biochemistry*, 40:15408-17 (2001).
Anderson et al., "Identification of the minimal funcational unit in the low density lipoprotein receptor-related protein for binding the receptor-associated protein (RAP)," *J. Biol. Chem.*, 275:21017-24 (2000).
Ashcom et al., "The human alpha 2-macroglobulin receptor: identification of a 420-kD cell surface glycoprotein specific for the activated conformation of alpha 2-macroglobulin", *J. Cell. Biol.*, 110:1041-8 (1990).
Bajari et al., "A minimal binding domain of the low density lipoprotein receptor family," *Biol. Chem.*, 379:1053-62 (1998).
Bickel et al., "Delivery of peptides and proteins through the blood-brain barrier", *Adv. Drug Deliv. Rev.*, 46:247-79 (2001).
Bickel et al., "Pharmacologic effects in vivo in brain by vector-mediated peptide drug delivery," *Proc. Natl. Acad. Sci. USA*, 90:2618-22 (1993).
"BioMarin reports interim data on NeuroTrans brain delivery program", *Biotech Week*, p. 3 (Jun. 19, 2002).
Blair et al., "Linkage of cytotoxic agents to immunoglobulins", *J. Immunol. Methods*, 59:129-43 (1983).
Blattler et al., "New heterobifunctional protein crosslinking reagent that forms an acid-labile link", *Biochem.*, 24:1517-24 (1985).
Bogan et al., "Anatomy of hot spots in protein interfaces," *J. Mol. Biol.*, 280:1-9 (1998).
Bu et al., "RAP, a novel type of ER chaperone," *Trends Cell Biol.*, 8:272-6 (1998).
Bu et al., "Receptor-associated protein is a folding chaperone for low density lipoprotein receptor-related protein," *J. Biol. Chem.*, 271:22218-24 (1996).
Bu, "The roles of receptor-associated protein (RAP) as a molecular chaperone for members of the LDL receptor family," *Int. Rev. Cytol.*, 209:79-116 (2001).

(Continued)

*Primary Examiner*—Daniel E. Kolker
(74) *Attorney, Agent, or Firm*—Marshall, Gerstein & Borun LLP

(57) ABSTRACT

The present invention is directed to a methods and compositions for receptor mediated drug delivery, particularly across the blood-brain barrier.

13 Claims, 37 Drawing Sheets

OTHER PUBLICATIONS

Canals et al., "Brain-derived neurotrophic factor regulates the onset and severity of motor dysfunction associated with enkephalinergic neuronal degeneration in Huntington's disease", *J. Neurosci.*, 24:7727-39 (2004).

Christensen et al., "Megalin and cubilin: synergistic endocytic receptors in renal proximal tubule", *Am. J. Physiol. Renal Physiol.*, 280:F562-73 (2001).

Clackson et al., "A hot spot of binding energy in a hormone-receptor interface," *Science*, 267:383-6 (1995).

Czekay et al., "Endocytic trafficking of megalin/RAP complexes: dissociation of the complexes in late endosomes", *Mol. Biol. Cell.*, 8:517-32 (1997).

Dehouck et al., "A new function for the LDL receptor: transcytosis of LDL across the blood-brain barrier", *J. Cell Biol.*, 138:877-89 (1997).

Delano, "Unraveling hot spots in binding interfaces: progress and challenges," *Curr. Opin. Struct. Biol.*, 12:14-20 (2002).

Dwyer et al., "High affinity RNase S-peptide variants obtained by phage display have a novel hot-spot of binding energy," *Biochemistry*, 40:13491-500 (2001).

Fahrlander et al., "Amplifying DNA probe signals: a 'Christmas Tree' approach", *Bio/Technology*, 6:1165-1168 (1988).

Faucheux et al., "Expression of lactoferrin receptors is increased in the mesencephalon of patients with Parkinson disease", *Proc. Natl. Acad. Sci. USA*, 92:9603-7 (1995).

Feng et al., "Progressive sequence alignment as a prerequisite to correct phylogenetic trees", *J. Mol. Evol.*, 25:351-60 (1987).

Ferrer et al., "Brain-derived neurotrophic factor in Huntington disease", *Brain Res.*, 866:257-61 (2000).

Fillebeen et al., "Receptor-mediated transcytosis of lactoferrin through the blood-brain barrier," *J. Biol. Chem.*, 274:7011-7 (1999).

Fisher et al., "Structure of an LDLR-RAP complex reveals a general mode for ligand recognition by lipoprotein receptors", *Mol. Cell.*, 22:277-83 (2006).

Fitzgerald et al., "Pseudomonas exotoxin-mediated selection yields cells with altered expression of low-density lipoprotein receptor-related protein", *J. Cell Biol.*, 129:1533-41 (1995).

Gao et al., "Structure-based method for analyzing protein-protein interfaces," *J. Mol. Model*, 10:4-54 (2004).

GenBank accession No. AAH49517, Low density lipoprotein receptor-related protein associated protein 1 (printed Apr. 22, 2004).

GenBank accession No. AAM90301, low density lipoprotein receptor-related protein-associated protein 1, (printed Apr. 22, 2004).

GenBank accession No. CAA05085, receptor-associated protein [*Gallus gallus*] (printed Apr. 22, 2004).

GenBank accession No. NP_506187, hypothetical protein C15C8.4 [*Caenorhabditis elegans*] (printed May 21, 2004).

GenBank accession No. NP_649950, CG8507 [*Drosophila melanogaster*] (printed May 21, 2004).

GenBank accession No. P30533, low density lipoprotein receptor-related protein-associated protein 1 (printed Apr. 22, 2004).

GenBank accession No. Q99068, low density lipoprotein receptor-related protein-associated protein 1 (printed Apr. 22, 2004).

GenBank accession No. X13916, human mRNA for LDL-receptor related protein (printed Apr. 22, 2004).

GenBank Accession No. XP_132029, low density lipoprotein receptor-related protein associated protein 1 [*Mus musculus*] (printed May 21, 2004).

Genbank Accession No. XP_313261, AGAP003521-PA [*Anopheles gambiae* str. PEST] (printed May 21, 2004).

Gutierrez et al., "Murine tumor necrosis factor alpha is transported from blood to brain in the mouse", *J. Neuroimmunology*, 47(2):169-76 (1993).

Halperin et al., "Protein-protein interactions: coupling of structurally conserved residues and of hot spots across interfaces. Implications for docking", *Structure*, 12:1027-38 (2004).

Henikoff et al., "Amino acid substitution matrices from protein blocks", *Proc. Natl. Acad. Sci. USA*, 89:10915-9 (1992).

Herz et al., "39-kDa protein modulates binding of ligands to low density lipoprotein receptor-related protein/alpha 2-macroglobulin receptor", *J. Biol. Chem.*, 266:21232-8 (1991).

Herz et al., "Gene transfer and disruption strategies to elucidate hepatic lipoprotein receptor functions", *Atherosclerosis*, 118 Suppl: S37-41 (1995).

Herz et al., "LRP: a multifunctional scavenger and signaling receptor," *J. Clin. Invest.*, 108:779-84 (2001).

Higgins et al., "Fast and sensitive multiple sequence alignments on a microcomputer", *Comput. Appl. Biosci.*, 5:151-3 (1989).

Hoogerbrugge et al., "Allogeneic bone marrow transplantation for lysosomal storage diseases. The European Group for Bone Marrow Transplantation", *Lancet*, 345:1398-402 (1995).

Horn et al., "Molecular analysis of ligand binding to the second cluster of complement-type repeats of the low density lipoprotein receptor-related protein", *J. Biol. Chem.*, 272:13608-13 (1997).

International Search Report for corresponding International Application No. PCT/US02/23923 (Apr. 4, 2005).

International Search Report for corresponding International Application No. PCT/US04/19153 (Feb. 3, 2005).

Jensen et al., "Binding site structure of one LRP-RAP complex: Implications for a common ligand-receptor binding motif," *J. Mol. Biol.*, 362:700-716 (2006).

Jensen et al., "Purification of the human placental alpha 2-macroglobulin receptor", *FEBS Lett.*, 255:275-80 (1989).

Karlin et al., "Applications and statistics for multiple high-scoring segments in molecular sequences", *Proc. Natl. Acad. Sci. USA*, 90:5873-7 (1993).

Kells et al., "AAV-mediated gene delivery of BDNF or GDNF is neuroprotective in a model of Huntington disease", *Mol. Ther.*, 9:682-8 (2004).

Kilic et al., "Intravenous TAT-GDNF is protective after focal cerebral ischemia in mice", *Stroke*, 34:1304-10 (2003).

King et al., "Preparation of protein conjugates via intermolecular hydrazone linkage", *Biochemistry*, 25:5774-9 (1986).

Kounnas et al., "The 39-kDa receptor-associated protein interacts with two members of the low density lipoprotein receptor family, $\alpha_2$-macroglobulin receptor and glycoprotein 330," *J. Biol. Chem.*, 267(29):21162-21166 (1992).

Kusuhara et al., "Efflux transport systems for drugs at the blood-brain barrier and blood-cerebrospinal fluid barrier (part 1)", *Drug Discov. Today*, 6:150-6 (2001).

Lee et al., "RAP uses a histidine switch to regulate its interaction with LRP in the ER and Golgi", *Mol. Cell*, 22:423-30 (2006).

Li et al., "Differential functions of members of the low density lipoprotein receptor family suggested by their distinct endocytosis rates", *J. Biol. Chem.*, 276:18000-6 (2001).

Li et al., "Magnitude of the hydrophobic effect at central versus peripheral sites in protein-protein interfaces," *Structure*, 13:297-307 (2005).

Lin et al., "GDNF: a glial cell line-derived neurotrophic factor for midbrain dopaminergic neurons", *Science*, 260:1130-2 (1993).

Lisi et al., "Preferential megalin-mediated transcytosis of low-hormonogenic thyroglobulin: a control mechanism for thyroid hormone release," *Proc. Natl. Acad. Sci. USA*, 100:14858-63 (2003).

Marino et al., "Binding of the low density lipoprotein receptor-associated protein (RAP) to thyroglobulin (Tg): putative role of RAP in the Tg secretory pathway", *Mol. Endocrinol.*, 15:1829-37 (2001).

Marino et al., "Role of thyroglobulin endocytic pathways in the control of thyroid hormone release", *Am. J. Physiol. Cell Physiol.*, 279:C1295-306 (2000).

Marzolo et al., "Differential distribution of low-density lipoprotein-receptor-related protein (LRP) and megalin in polarized epithelial cells is determined by their cytoplasmic domains", *Traffic*, 4:273-88 (2003).

Mazumder et al., "Translational control by the 3'-UTR: the ends specify the means", *Trends Biochem. Sci.*, 28:91-8 (2003).

McCormick et al., "Independent and cooperative roles of N-Glycans and molecular chaperones in the folding and disulfide bond formation of the low-density lipoprotein (LDL) receptor-related protein," *Biochemistry*, 44:5794-803 (2005).

Medved et al., "Domain organization of the 39-kDa receptor-associated protein", *J. Biol. Chem.*, 274:717-27 (1999).

Meilinger et al., "Removal of lactoferrin from plasma is mediated by binding to low density lipoprotein receptor-related protein/$\alpha_2$-macroglobulin receptor and transport to endosomes", *FEBS Lett.*, 360(1):70-4 (1995).

Melman et al., "High affinity binding of receptor-associated protein to heparin and low density lipoprotein receptor-related protein requires similar basic amino acid sequence motifs", *J. Biol. Chem.*, 274:29338-46 (2001).

Migliorini et al., "Allosteric modulation of ligand binding to low density lipoprotein receptor-related protein by the receptor-associated protein requires critical lysine residues within its carboxyl-terminal domain," *J. Biol. Chem.*, 278(20):17986-92 (2003).

Mikhailenko et al., "Functional domains of the very low density lipoprotein receptor: molecular analysis of ligand binding and acid-dependent ligand dissociation mechanisms", *J. Cell Sci.*, 112:3269-81 (1999).

Moestrup et al. "B2-Glycoprotein-1 (Apolipoprotein H) and B2-glycoprotein-I-phospholipid complex harbor a recognition site for the endocytic receptor megalin", *J. Clin. Invest.*, 102:902-9 (1998).

Needleman et al., "A general method applicable to the search for similarities in the amino acid sequence of two proteins", *J. Mol. Biol.*, 48:443-53 (1970).

Neels et al., "The second and fourth cluster of class a cysteine-rich repeats of the low density lipoprotein receptor-related protein share ligand-binding properties," *J. Biol. Chem.*, 274(44):31305-11 (1999).

Nielsen et al., "The solution structure of the N-terminal domain of alpha2-macroglobulin receptor-associated protein", *Proc. Natl. Acad. Sci. USA*, 94:7521-5 (1997).

Niemeier et al., "Identification of megalin/gp330 as a receptor for lipoprotein(a) in vitro", *Arterioscler. Thromb. Vasc. Biol.*, 19:552-61 (1999).

Obermoeller et al., "Differential functions of triplicated repeats suggest two independent roles for the receptor-associated protein as a molecular chaperone," *J. Biol. Chem.*, 272(16):10761-8 (1997).

Orlando et al., "Functional domains of the receptor-associated protein (RAP)", *Proc. Natl. Acad. Sci. USA*, 91:3161-5 (1994).

Orlando et al., "Identification of the second cluster of ligand-binding repeats in megalin as a site for receptor-ligand interactions", *Proc. Natl. Acad. Sci. USA*, 94:2368-73 (1997).

Pan et al., "Efficient transfer of receptor-associated protein (RAP) across the blood-brain barrier", *J. Cell Sci.*, 177: 5071-8 (2004).

Pardridge, "Blood-brain barrier biology and methodology," *J. Neurovirol.*, 5:556-69 (1999).

Pardridge, "Drug and gene targeting to the brain with molecular Trojan horses", *Nat. Rev. Drug Discov.*, 1:131-9 (2002).

Pearson et al., "Improved tools for biological sequence comparison", *Proc. Natl. Acad. Sci. USA*, 85:2444-8 (1988).

Perez-Navarro et al., "Brain-derived neurotrophic factor, neurotrophin-3, and neurotrophin-4/5 prevent the death of striatal projection neurons in a rodent model of Huntington's disease", *J. Neurochem.*, 75:2190-9 (2000).

Prince et al., "Lipoprotein receptor binding, cellular uptake, and lysosomal delivery of fusions between the receptor-associated protein (RAP) and $\alpha$-$_L$-iduronidase or acid $\alpha$-glucosidase," *J. Biol. Chem.*, 279:35037-46 (2004).

Qian et al., "Expression of iron transport proteins and excessive iron accumulation in the brain in neurodegenerative disorders", *Brain Res. Rev.*, 27:257-67 (1998).

Quinn et al., "Soluble low density lipoprotein receptor-related protein (LRP) circulates in human plasma", *J. Biol. Chem.*, 272:23946-51 (1997).

Rall et al., "The domain structure of human receptor-associated protein. Protease sensitivity and guanidine HCl denaturation", *J. Biol. Chem.*, 273:24152-7 (1998).

Reddy, "Controlled-release, pegylation, liposomal formulations: new mechanisms in the delivery of injectable drugs", *Ann. Pharmacother.*, 34:915-23 (2000).

Russell et al., "Recombinant proteins for genetic disease", *Clin. Genet.*, 55:389-94 (1999).

Savonen et al., "The carboxyl-terminal domain of receptor-associated protein facilitates proper folding and trafficking of the very low density lipoprotein receptor by interaction with the three amino-terminal ligand-binding repeats of the receptor", *J. Biol. Chem.*, 274:25877-82 (1999).

Schullek, "A high-density screening format for encoded combinatorial libraries: Assay miniaturization and its application to enzymatic reactions", *Anal. Biochem.*, 246:20-9 (1997).

Shibata et al., "Clearance of alzheimer's amyloid-$\beta_{1-40}$ peptide from brain by LDL Receptor-related Protein-1 at the Blood-brain Barrier," *J. Clin. Invest.*, 106:1489-1499 (2000).

Smith et al., "Comparison of biosequences", *Adv. Appl. Math.*, 2:482-9 (1981).

Spires et al., "Environmental enrichment rescues protein deficits in a mouse model of Huntington's disease, indicating a possible disease mechanism", *J. Neurosci.*, 24:2270-6 (2004).

Srinivasachar et al., "New protein cross-linking reagents that are cleaved by mild acid", *Biochemistry*, 28:2501-9 (1989).

Supplementary European Search Report for corresponding European Application No. 04776636 (Jun. 8, 2009).

Swiss-Prot Primary Accession No. Q07954 (printed Apr. 22, 2004).

Takahashi et al., "Rabbit very low density lipoprotein receptor: a low density lipoprotein receptor-like protein with distinct ligand specificity", *Proc. Natl. Acad. Sci. USA*, 89:9252-6 (1992).

Thompson et al., "CLUSTAL W: improving the sensitivity of progressive multiple sequence alignment through sequence weighting, position-specific gap penalties and weight matrix choice", *Nucleic Acids Res.*, 22:4673-80 (1994).

Tsuji et al., "Carrier-mediated or specialized transport of drugs across the blood-brain barrier," *Adv. Drug Deliv. Rev.*, 36:277-90 (1999).

Tsuji et al., "Lysosomal enzyme replacement using alpha 2-macroglobulin as a transport vehicle", *J. Biochem.*, 115:937-44 (1994).

Van Den Hout et al., "Recombinant human alpha-glucosidase from rabbit milk in Pompe patients", *Lancet*, 356:397-8 (2000).

Vash et al., "Three complement-type repeats of the low-density lipoprotein receptor-related protein define a common binding site for RAP, PAI-1, and lactoferrin", *Blood*, 92:3277-85 (1998).

Warshawsky et al., "Binding analysis of amino-terminal and carboxyl-terminal regions of the 39-kDa protein to the low density lipoprotein receptor-related protein", *J. Biol. Chem.*, 269:3325-30 (1994).

Wilchek et al., "The avidin-biotin complex in bioanalytical applications", *Anal. Biochem.*, 171:1-32 (1988).

Williams et al., "A novel mechanism for controlling the activity of alpha 2-macroglobulin receptor/low density lipoprotein receptor-related protein. Multiple regulatory sites for 39-kDa receptor-associated protein", *J. Biol. Chem.*, 267:9035-40 (1992).

Willnow et al., "Low density lipoprotein receptor-related protein and gp330 bind similar ligands, Including plasminogen activator-inhibitor complexes and lactoferrin, an inhibitor of chylomicron remnant clearance," *J. Biol. Chem.*, 267(36):26172-80 (1992).

Wisselaar et al., "Structural and functional changes of lysosomal acid alpha-glucosidase during intracellular transport and maturation", *J. Biol. Chem.*, 268:2223-31 (1993).

Yenofsky et al., "A mutant neomycin phosphotransferase II gene reduces the resistance of transformants to antibiotic selection pressure", *Proc. Natl. Acad. Sci. USA*, 87:3435-9 (1990).

Zlokovic et al., "Glycoprotein 330/megalin: probable role in receptor-mediated transport of apolipoprotein J alone and in a complex with Alzheimer disease amyloid beta at the blood-brain and blood-cerebrospinal fluid barriers," *Proc. Natl. Acad. Sci. USA*, 93:4229-34 (1996).

Zuccato et al., "Loss of huntingtin-mediated BDNF gene transcription in Huntington's disease", *Science*, 293:493-8 (2001).

\* cited by examiner

FIGURE 2 Primers used to obtain sequences high-fidelity PCR amplification of human cDNA.

RAPF: GCGATAGGATCCTACTCGCGGGAGAAGAACCAGCCCAAGCCGTCCCCGA (SEQ ID NO: 12)

RAPR: GCGATAAACCGGTTTCTGCCTCGGCGCGAGCTCTGGAGATCCTGCCGGACAGGTCCT (SEQ ID NO: 13)

GAAF: GCGATAACCGGTGCACACCCCGGCCGTCCCAGAGCAGTG (SEQ ID NO: 14)

GAAR: GCGATACTCGAGTCAACACCAGCTGACGAGAAACTGC (SEQ ID NO: 15)

IDUF: GCGATAACCGGTGAGGCCCCCCGCACCTGGTGCATGTGGACGCGGC (SEQ ID NO: 16)

IDUR: GCGATACTCGAGTCATGGATTGCCCGGGGATGGGGGCCCTCTTGG (SEQ ID NO: 17)

GDNF: ACAGTGACCGGTTCACCAGATAAACAAATGGCA (SEQ ID NO: 18)

GDNR: ACAGTGCTCGAGTCTAGATCAGATACATCCACACCTTT (SEQ ID NO: 19)

GDNF fusion, substitution of RAPF with RAPBACF in RAP amplification of GDNF construct.

RAPBACF: ACAGTGGCCATGGGGGGTTCTTACTCGCGGGAGAAGAACCAGCCCAAGCCG (SEQ ID NO: 20)

Figure 3. Nucleotide (SEQ ID NO:6) and protein (SEQ ID NO:7) sequences of the RAP-GAA fusion

```
cttaccgccatgcggggtccgagcggggctctgtggctgctcctggctctgcgcaccgtg
            M  R  G  P  S  G  A  L  W  L  L  A  L  R  T  V
ctcggatcctactcgcgggagaagaaccagcccaagccgtccccgaaacgcgagtccgga
 L  G  S  Y  S  R  E  K  N  Q  P  K  P  S  P  K  R  E  S  G
gaggagttccgcatggagaagttgaaccagctgtgggagaaggcccagcgactgcatctt
 E  E  F  R  M  E  K  L  N  Q  L  W  E  K  A  Q  R  L  H  L
cctcccgtgaggctggccgagctccacgctgatctgaagatacaggagagggacgaactc
 P  P  V  R  L  A  E  L  H  A  D  L  K  I  Q  E  R  D  E  L
gcctggaagaaactaaagcttgacggcttggacgaagatggggagaaggaagcgagactc
 A  W  K  K  L  K  L  D  G  L  D  E  D  G  E  K  E  A  R  L
atacgcaacctcaatgtcatcttggccaagtatggtctggacggaaagaaggacgctcgg
 I  R  N  L  N  V  I  L  A  K  Y  G  L  D  G  K  K  D  A  R
caggtgaccagcaactccctcagtggcacccaggaagacgggctggatgaccccaggctg
 Q  V  T  S  N  S  L  S  G  T  Q  E  D  G  L  D  D  P  R  L
gaaaagctgtggcacaaggcgaagacctctgggaaattctccggcgaagaactggacaag
 E  K  L  W  H  K  A  K  T  S  G  K  F  S  G  E  E  L  D  K
ctctggcgggagttcctgcatcacaaagagaaagttcacgagtacaacgtcctgctggag
 L  W  R  E  F  L  H  H  K  E  K  V  H  E  Y  N  V  L  L  E
accctgagcaggaccgaagaaatccacgagaacgtcattagcccctcggacctgagcgac
 T  L  S  R  T  E  E  I  H  E  N  V  I  S  P  S  D  L  S  D
atcaagggcagcgtcctgcacagcaggcacacggagctgaaggagaagctgcgcagcatc
 I  K  G  S  V  L  H  S  R  H  T  E  L  K  E  K  L  R  S  I
aaccagggcctggaccgcctgcgcagggtcagccaccagggctacagcactgaggctgag
 N  Q  G  L  D  R  L  R  R  V  S  H  Q  G  Y  S  T  E  A  E
ttcgaggagcccagggtgattgacctgtgggacctggcgcagtccgccaacctcacggac
 F  E  E  P  R  V  I  D  L  W  D  L  A  Q  S  A  N  L  T  D
aaggagctggaggcgttccgggaggagctcaagcacttcgaagccaaaatcgagaagcac
 K  E  L  E  A  F  R  E  E  L  K  H  F  E  A  K  I  E  K  H
aaccactaccagaagcagctggagattgcgcacgagaagctgaggcacgcagagagcgtg
 N  H  Y  Q  K  Q  L  E  I  A  H  E  K  L  R  H  A  E  S  V
ggcgacggcgagcgtgtgagccgcagccgcgagaagcacgccctgctggaggggcggacc
 G  D  G  E  R  V  S  R  S  R  E  K  H  A  L  L  E  G  R  T
aaggagctgggctacacggtgaagaagcatctgcaggacctgtccggcaggatctccaga
 K  E  L  G  Y  T  V  K  K  H  L  Q  D  L  S  G  R  I  S  R
gctcgcgccgaggcagaaaccggtgcacaccccggccgtcccagagcagtgcccacacag
 A  R  A  E  A  E  T  G  A  H  P  G  R  P  R  A  V  P  T  Q
tgcgacgtcccccccaacagccgcttcgattgcgcccctgacaaggccatcacccaggaa
 C  D  V  P  P  N  S  R  F  D  C  A  P  D  K  A  I  T  Q  E
cagtgcgaggcccgcggctgctgctacatccctgcaaagcaggggctgcagggagcccag
 Q  C  E  A  R  G  C  C  Y  I  P  A  K  Q  G  L  Q  G  A  Q
atggggcagccctggtgcttcttcccacccagctaccccagctacaagctggagaacctg
 M  G  Q  P  W  C  F  F  P  P  S  Y  P  S  Y  K  L  E  N  L
agctcctctgaaatgggctacacggccaccctgacccgtaccaccccaccttcttcccc
 S  S  S  E  M  G  Y  T  A  T  L  T  R  T  T  P  T  F  F  P
aaggacatcctgacccTgcggctggacgtgatgatggagactgagaaccgcctccacttc
 K  D  I  L  T  L  R  L  D  V  M  M  E  T  E  N  R  L  H  F
acgatcaaagatccagctaacaggcgctacgaggtgcccttggagacccgcgtgtccac
 T  I  K  D  P  A  N  R  R  Y  E  V  P  L  E  T  P  R  V  H
agccgggcaccgtccccactctacagcgtggagttctccgaggagcccttcggggtgatc
 S  R  A  P  S  P  L  Y  S  V  E  F  S  E  E  P  F  G  V  I
```

Figure 3A

```
gtgcaccggcagctggacggccgcgtgctgctgaacacgacggtggcgcccctgttcttt
 V  H  R  Q  L  D  G  R  V  L  L  N  T  T  V  A  P  L  F  F
gcggaccagttccttcagctgtccacctcgctgccctcgcagtatatcacaggcctcgcc
 A  D  Q  F  L  Q  L  S  T  S  L  P  S  Q  Y  I  T  G  L  A
gagcacctcagtcccctgatgctcagcaccagctggaccaggatcaccctgtggaaccgg
 E  H  L  S  P  L  M  L  S  T  S  W  T  R  I  T  L  W  N  R
gaccttgcgccacgcccggtgcgaacctctacgggtctcacccttttctacctggcgctg
 D  L  A  P  T  P  G  A  N  L  Y  G  S  H  P  F  Y  L  A  L
gaggacggcgggtcggcacacggggtgttcctgctaaacagcaatgccatggatgtggtc
 E  D  G  G  S  A  H  G  V  F  L  L  N  S  N  A  M  D  V  V
ctgcagccgagccctgcccttagctggaggtcgacaggtgggatcctggatgtctacatc
 L  Q  P  S  P  A  L  S  W  R  S  T  G  G  I  L  D  V  Y  I
ttcctgggcccagagcccaagagcgtggtgcagcagtacctggacgttgtgggataccCg
 F  L  G  P  E  P  K  S  V  V  Q  Q  Y  L  D  V  V  G  Y  P
ttcatgccgccatactggggcctgggcttccacctgtgccgctggggctactcctccacc
 F  M  P  P  Y  W  G  L  G  F  H  L  C  R  W  G  Y  S  S  T
gctatcacccgccaggtggtggagaacatgaccagggcccacttcccCctggacgtccaa
 A  I  T  R  Q  V  V  E  N  M  T  R  A  H  F  P  L  D  V  Q
tggaacgacctggactacatggactcccggagggacttcacgttcaacaaggatggcttc
 W  N  D  L  D  Y  M  D  S  R  R  D  F  T  F  N  K  D  G  F
cgggacttccCggccatggtgcaggagctgcaccagggcggccggcgctacatgatgatc
 R  D  F  P  A  M  V  Q  E  L  H  Q  G  G  R  R  Y  M  M  I
gtggatcctgccatcagcagctcgggccctgccggagctacaggccctacgacgaggt
 V  D  P  A  I  S  S  S  G  P  A  G  S  Y  R  P  Y  D  E  G
ctgcggggggggttttcatcaccaacgagaccggccagccgctgattgggaaggtatgg
 L  R  R  G  V  F  I  T  N  E  T  G  Q  P  L  I  G  K  V  W
cccgggtccactgccttccccgacttcaccaaccccacagccctggcctggtggaggac
 P  G  S  T  A  F  P  D  F  T  N  P  T  A  L  A  W  W  E  D
atggtggctgagttccatgaccaggtgcccttcgacggcttgtggattgacatgaacgag
 M  V  A  E  F  H  D  Q  V  P  F  D  G  L  W  I  D  M  N  E
ccttccaacttcatcagaggctctgaggacggctgccccaacaatgagctggagaaccca
 P  S  N  F  I  R  G  S  E  D  G  C  P  N  N  E  L  E  N  P
ccctacgtgcctggggtggttggggggaccctccaggcggccaccatctgtgcctccagc
 P  Y  V  P  G  V  V  G  G  T  L  Q  A  A  T  I  C  A  S  S
caccagtttctctccacacactacaacctgcacaacctctacggcctgaccgaagccatc
 H  Q  F  L  S  T  H  Y  N  L  H  N  L  Y  G  L  T  E  A  I
gcctcccacagggcgctggtgaaggctcgggggacacgcccatttgtgatctcccgctcg
 A  S  H  R  A  L  V  K  A  R  G  T  R  P  F  V  I  S  R  S
acctttgctggccacggccgatacgccggccactggacgggggacgtgtggagctcctgg
 T  F  A  G  H  G  R  Y  A  G  H  W  T  G  D  V  W  S  S  W
gagcagctcgcctcctccgtgccagaaatcctgcagtttaacctgctgggggtgcctctg
 E  Q  L  A  S  S  V  P  E  I  L  Q  F  N  L  L  G  V  P  L
gtcggggccgacgtctgcggcttcctgggcaacacctcagaggagctgtgtgtgcgctgg
 V  G  A  D  V  C  G  F  L  G  N  T  S  E  E  L  C  V  R  W
acccagctgggggccttctaccccttcatgcggaaccacaacagcctgctcagtctgccc
 T  Q  L  G  A  F  Y  P  F  M  R  N  H  N  S  L  L  S  L  P
caggagccgtacagcttcagcgagccggcccagcaggccatgaggaaggccctcaccctg
 Q  E  P  Y  S  F  S  E  P  A  Q  Q  A  M  R  K  A  L  T  L
cgctacgcactcctcccccacctctacacactgttccaccaggcccacgtcgcggggag
 R  Y  A  L  L  P  H  L  Y  T  L  F  H  Q  A  H  V  A  G  E
accgtggcccggcccctcttcctggagttccccaaggactctagcacctggactgtggac
 T  V  A  R  P  L  F  L  E  F  P  K  D  S  S  T  W  T  V  D
caccagctcctgtgggggaggccctgctcatcaccccagtgctccaggccgggaaggcc
 H  Q  L  L  W  G  E  A  L  L  I  T  P  V  L  Q  A  G  K  A
```

Figure 3B

```
gaagtgactggctacttcccttgggcacatggtacgacctgcagacggtgccaatagag
 E  V  T  G  Y  F  P  L  G  T  W  Y  D  L  Q  T  V  P  I  E
gcccttggcagcctccacccccacctgcagctccccgtgagccagccatccacagcgag
 A  L  G  S  L  P  P  P  P  A  A  P  R  E  P  A  I  H  S  E
gggcagtgggtgacgctgccggccccctggacaccatcaacgtccacctccgggctggg
 G  Q  W  V  T  L  P  A  P  L  D  T  I  N  V  H  L  R  A  G
tacatcatcccctgcagggccctggcctcacaaccacagagtcccgccagcagcccatg
 Y  I  I  P  L  Q  G  P  G  L  T  T  T  E  S  R  Q  Q  P  M
gccctggctgtggccctaaccaagggtggagaggcccgaggggagctgttctgggacgat
 A  L  A  V  A  L  T  K  G  G  E  A  R  G  E  L  F  W  D  D
ggagagagcctggaagtgctggagcgaggggcctacacacaggtcatcttcctggccagg
 G  E  S  L  E  V  L  E  R  G  A  Y  T  Q  V  I  F  L  A  R
aataacacgatcgtgaatgagctggtacgtgtgaccagtgagggagctggcctgcagctg
 N  N  T  I  V  N  E  L  V  R  V  T  S  E  A  G  L  Q  L
cagaaggtgactgtcctgggcgtggccacggcgcccagcaggtcctctccaacggtgtc
 Q  K  V  T  V  L  G  V  A  T  A  P  Q  Q  V  L  S  N  G  V
cctgtctccaacttcacctacagccccgacaccaaggtcctggacatctgtgtctcgctg
 P  V  S  N  F  T  Y  S  P  D  T  K  V  L  D  I  C  V  S  L
ttgatgggagagcagtttctcgtcagctggtgttgactcgag
 L  M  G  E  Q  F  L  V  S  W  C  -
```

Figure 3C

Melanotransferrin signal sequence is italicized. Linker peptide is underlined.

FIGURE 4. Nucleotide (SEQ ID NO:8) and protein (SEQ ID NO:9) sequences of the RAP-IDU fusion

```
aagcttaccgccatgcggggtccgagcggggctctgtggctgctcctggctctgcgcacc
              M  R  G  P  S  G  A  L  W  L  L  A  L  R  T
gtgctcggatcctactcgcgggagaagaaccagcccaagccgtccccgaaacgcgagtcc
 V  L  G  S  Y  S  R  E  K  N  Q  P  K  P  S  P  K  R  E  S
ggagaggagttccgcatggagaagttgaaccagctgtgggagaaggcccagcgactgcat
 G  E  E  F  R  M  E  K  L  N  Q  L  W  E  K  A  Q  R  L  H
cttcctcccgtgaggctggccgagctccacgctgatctgaagatacaggagagggacgaa
 L  P  P  V  R  L  A  E  L  H  A  D  L  K  I  Q  E  R  D  E
ctcgcctggaagaaactaaagcttgacggcttggacgaagatggggagaaggaagcgaga
 L  A  W  K  K  L  K  L  D  G  L  D  E  D  G  E  K  E  A  R
ctcatacgcaacctcaatgtcatcttggccaagtatggtctggacggaaagaaggacgct
 L  I  R  N  L  N  V  I  L  A  K  Y  G  L  D  G  K  K  D  A
cggcaggtgaccagcaactccctcagtggcacccaggaagacgggctggatccccagg
 R  Q  V  T  S  N  S  L  S  G  T  Q  E  D  G  L  D  D  P  R
ctggaaaagctgtggcacaaggcgaagacctctgggaaattctccggcgaagaactggac
 L  E  K  L  W  H  K  A  K  T  S  G  K  F  S  G  E  E  L  D
aagctctggcgggagttcctgcatcacaaagagaaagttcacgagtacaacgtcctgctg
 K  L  W  R  E  F  L  H  H  K  E  K  V  H  E  Y  N  V  L  L
gagaccctgagcaggaccgaagaaatccacgagaacgtcattagcccctcggacctgagc
 E  T  L  S  R  T  E  E  I  H  E  N  V  I  S  P  S  D  L  S
gacatcaagggcagcgtcctgcacagcaggcacacggagctgaaggagaagctgcgcagc
 D  I  K  G  S  V  L  H  S  R  H  T  E  L  K  E  K  L  R  S
atcaaccagggcctggaccgcctgcgcagggtcagccaccagggctacagcactgaggct
 I  N  Q  G  L  D  R  L  R  R  V  S  H  Q  G  Y  S  T  E  A
gagttcgaggagcccagggtgattgacctgtgggacctggcgcagtccgccaacctcacg
 E  F  E  E  P  R  V  I  D  L  W  D  L  A  Q  S  A  N  L  T
gacaaggagctggaggcgttccgggaggagctcaagcacttcgaagccaaaatcgagaag
 D  K  E  L  E  A  F  R  E  E  L  K  H  F  E  A  K  I  E  K
cacaaccactaccagaagcagctggagattgcgcacgagaagctgaggcacgcagagagc
 H  N  H  Y  Q  K  Q  L  E  I  A  H  E  K  L  R  H  A  E  S
gtgggcgacggcgagcgtgtgagccgcagccgcgagaagcacgccctgctggaggggcgg
 V  G  D  G  E  R  V  S  R  S  R  E  K  H  A  L  L  E  G  R
accaaggagctgggctacacggtgaagaagcatctgcaggacctgtccggcaggatctcc
 T  K  E  L  G  Y  T  V  K  K  H  L  Q  D  L  S  G  R  I  S
agagctcgcgccgaggcagaaaccggtgaggccccgcacctggtgcatgtggacgcggcc
 R  A  R  A  E  A  E  T  G  E  A  P  H  L  V  H  V  D  A  A
cgcgcgctgtggcccctgcggcgcttctggaggagcacaggcttctgcccccgctgcca
 R  A  L  W  P  L  R  R  F  W  R  S  T  G  F  C  P  P  L  P
cacagccaggctgaccagtacgtcctcagctgggaccagcagctcaacctcgcctatgtg
 H  S  Q  A  D  Q  Y  V  L  S  W  D  Q  Q  L  N  L  A  Y  V
ggcgccgtccctcaccgcggcatcaagcaggtccggacccactggctgctggagcttgtc
 G  A  V  P  H  R  G  I  K  Q  V  R  T  H  W  L  L  E  L  V
accaccagggggtccactggacggggcctgagctacaacttcacccacctggacgggtac
 T  T  R  G  S  T  G  R  G  L  S  Y  N  F  T  H  L  D  G  Y
ttggaccttctcagggagaaccagctcctcccagggtttgagctgatgggcagcgcctcg
 L  D  L  L  R  E  N  Q  L  L  P  G  F  E  L  M  G  S  A  S
ggccacttcactgactttgaggacaagcagcaggtgtttgagtggaaggacttggtctcc
 G  H  F  T  D  F  E  D  K  Q  Q  V  F  E  W  K  D  L  V  S
agcctggccaggagatacatcggtaggtacggactggcgcatgtttccaagtggaacttc
 S  L  A  R  R  Y  I  G  R  Y  G  L  A  H  V  S  K  W  N  F
```

Figure 4A

```
gagacgtggaatgagccagaccaccacgactttgacaacgtctccatgaccatgcaaggc
 E  T  W  N  E  P  D  H  H  D  F  D  N  V  S  M  T  M  Q  G
ttcctgaactactacgatgcctgctcggagggtctgcgcgccgccagccccgccctgcgg
 F  L  N  Y  Y  D  A  C  S  E  G  L  R  A  A  S  P  A  L  R
ctgggaggccccggcgactccttccacaccccaccgcgatccccgctgagctggggcctc
 L  G  G  P  G  D  S  F  H  T  P  P  R  S  P  L  S  W  G  L
ctgcgccactgccacgacggtaccaacttcttcactggggaggcgggcgtgcggctggac
 L  R  H  C  H  D  G  T  N  F  F  T  G  E  A  G  V  R  L  D
tacatctccctccacaggaaggggtgcgcgcagctccatctccatcctggagcaggagaag
 Y  I  S  L  H  R  K  G  A  R  S  S  I  S  I  L  E  Q  E  K
gtcgtcgcgcagcagatccggcagctcttccccaagttcgcggacacccccatttacaac
 V  V  A  Q  Q  I  R  Q  L  F  P  K  F  A  D  T  P  I  Y  N
gacgaggcggacccgctggtgggctggtccctgccacagccgtggagggcggacgtgacc
 D  E  A  D  P  L  V  G  W  S  L  P  Q  P  W  R  A  D  V  T
tacgcggccatggtggtgaaggtcatcgcgcagcatcagaacctgctactggccaacacc
 Y  A  A  M  V  V  K  V  I  A  Q  H  Q  N  L  L  L  A  N  T
acctccgccttcccctacgcgctcctgagcaacgacaatgccttcctgagctaccacccg
 T  S  A  F  P  Y  A  L  L  S  N  D  N  A  F  L  S  Y  H  P
caccccttcgcgcagcgcacgctcaccgcgcgcttccaggtcaacaacacccgcccgccg
 H  P  F  A  Q  R  T  L  T  A  R  F  Q  V  N  N  T  R  P  P
cacgtgcagctgttgcgcaagccggtgctcacggccatgggctgctggcgctgctggat
 H  V  Q  L  L  R  K  P  V  L  T  A  M  G  L  L  A  L  L  D
gaggagcagctctgggccgaagtgtcgcaggccgggaccgtcctggacagcaaccacacg
 E  E  Q  L  W  A  E  V  S  Q  A  G  T  V  L  D  S  N  H  T
gtgggcgtcctggccagcgcccaccgcccccagggcccggccgacgcctggcgcgccgcg
 V  G  V  L  A  S  A  H  R  P  Q  G  P  A  D  A  W  R  A  A
gtgctgatctacgcgagcgacgacacccgcgcccaccccaaccgcagcgtcgcggtgacc
 V  L  I  Y  A  S  D  D  T  R  A  H  P  N  R  S  V  A  V  T
ctgcggctgcgcggggtgccccccggcccgggcctggtctacgtcacgcgctacctggac
 L  R  L  R  G  V  P  P  G  P  G  L  V  Y  V  T  R  Y  L  D
aacgggctctgcagccccgacggcgagtggcggcgcctgggccggcccgtcttccccacg
 N  G  L  C  S  P  D  G  E  W  R  R  L  G  R  P  V  F  P  T
gcagagcagttccggcgcatgcgcgcggctgaggacccggtggccgcggcgccccgcccc
 A  E  Q  F  R  R  M  R  A  A  E  D  P  V  A  A  A  P  R  P
ttacccgccggcggccgcctgaccctgcgccccgcgctgcggctgccgtcgcttttgctg
 L  P  A  G  G  R  L  T  L  R  P  A  L  R  L  P  S  L  L  L
gtgcacgtgtgtgcgcgccccgagaagccgcccgggcaggtcacgcggctccgcgccctg
 V  H  V  C  A  R  P  E  K  P  P  G  Q  V  T  R  L  R  A  L
cccctgacccaagggcagctggttctggtctggtcggatgaacacgtgggctccaagtgc
 P  L  T  Q  G  Q  L  V  L  V  W  S  D  E  H  V  G  S  K  C
ctgtggacatacgagatccagttctctcaggacggtaaggcgtacaccccggtcagcagg
 L  W  T  Y  E  I  Q  F  S  Q  D  G  K  A  Y  T  P  V  S  R
aagccatcgaccttcaacctctttgtgttcagcccagacacaggtgctgtctctggctcc
 K  P  S  T  F  N  L  F  V  F  S  P  D  T  G  A  V  S  G  S
taccgagttcgagccctggactactgggcccgaccaggccccttctcggaccctgtgccg
 Y  R  V  R  A  L  D  Y  W  A  R  P  G  P  F  S  D  P  V  P
tacctggaggtccctgtgccaagagggccccatccccgggcaatccatgactcgag
 Y  L  E  V  P  V  P  R  G  P  P  S  P  G  N  P  -
```

Figure 4B

Melanotransferrin signal sequence is italicized. Linker peptide is underlined.

FIGURE 5. Nucleotide (SEQ ID NO:10) and protein (SEQ ID NO:11) sequences of the RAP-GDNF fusion

```
atgggggggttcttactcgcgggagaagaaccagcccaagccgtccccgaaacgcgagtcc
 M  G  G  S  Y  S  R  E  K  N  Q  P  K  P  S  P  K  R  E  S
ggagaggagttccgcatggagaagttgaaccagctgtgggagaaggcccagcgactgcat
 G  E  E  F  R  M  E  K  L  N  Q  L  W  E  K  A  Q  R  L  H
cttcctcccgtgaggctggccgagctccacgctgatctgaagatacaggagagggacgaa
 L  P  P  V  R  L  A  E  L  H  A  D  L  K  I  Q  E  R  D  E
ctcgcctggaagaaactaaagcttgacggcttggacgaagatggggagaaggaagcgaga
 L  A  W  K  K  L  K  L  D  G  L  D  E  D  G  E  K  E  A  R
ctcatacgcaacctcaatgtcatcttggccaagtatggtctggacggaaagaaggacgct
 L  I  R  N  L  N  V  I  L  A  K  Y  G  L  D  G  K  K  D  A
cggcaggtgaccagcaactccctcagtggcacccaggaagacgggctggatgacccccagg
 R  Q  V  T  S  N  S  L  S  G  T  Q  E  D  G  L  D  D  P  R
ctggaaaagctgtggcacaaggcgaagacctctgggaaattctccggcgaagaactggac
 L  E  K  L  W  H  K  A  K  T  S  G  K  F  S  G  E  E  L  D
aagctctggcgggagttcctgcatcacaaagagaaagttcacgagtacaacgtcctgctg
 K  L  W  R  E  F  L  H  H  K  E  K  V  H  E  Y  N  V  L  L
gagaccctgagcaggaccgaagaaatccacgagaacgtcattagcccctcggacctgagc
 E  T  L  S  R  T  E  E  I  H  E  N  V  I  S  P  S  D  L  S
gacatcaagggcagcgtcctgcacagcaggcacacggagctgaaggagaagctgcgcagc
 D  I  K  G  S  V  L  H  S  R  H  T  E  L  K  E  K  L  R  S
atcaaccagggcctggaccgcctgcgcagggtcagccaccagggctacagcactgaggct
 I  N  Q  G  L  D  R  L  R  R  V  S  H  Q  G  Y  S  T  E  A
gagttcgaggagcccagggtgattgacctgtgggacctggcgcagtccgccaacctcacg
 E  F  E  E  P  R  V  I  D  L  W  D  L  A  Q  S  A  N  L  T
gacaaggagctggaggcgttccgggaggagctcaagcacttcgaagccaaaatcgagaag
 D  K  E  L  E  A  F  R  E  E  L  K  H  F  E  A  K  I  E  K
cacaaccactaccagaagcagctggagattgcgcacgagaagctgaggcacgcagagagc
 H  N  H  Y  Q  K  Q  L  E  I  A  H  E  K  L  R  H  A  E  S
gtgggcgacggcgagcgtgtgagccgcagccgcgagaagcacgccctgctggaggggcgg
 V  G  D  G  E  R  V  S  R  S  R  E  K  H  A  L  L  E  G  R
accaaggagctgggctacacggtgaagaagcatctgcaggacctgtccggcaggatctcc
 T  K  E  L  G  Y  T  V  K  K  H  L  Q  D  L  S  G  R  I  S
agagctcgggccgaggcagaaaccggttcaccagataaacaaatggcagtgcttcctaga
 R  A  R  <u>A  E  A  E  T  G  S  P  D  K  Q  M  A  V  L  P  R</u>
agagagcggaatcggcaggctgcagctgccaacccagagaattccagaggaaaaggtcgg
 R  E  R  N  R  Q  A  A  A  A  N  P  E  N  S  R  G  K  G  R
agaggccagaggggcaaaaaccggggttgtgtcttaactgcaatacatttaaatgtcact
 R  G  Q  R  G  K  N  R  G  C  V  L  T  A  I  H  L  N  V  T
gacttgggtctgggctatgaaaccaaggaggaactgatttttaggtactgcagcggctct
 D  L  G  L  G  Y  E  T  K  E  E  L  I  F  R  Y  C  S  G  S
tgcgatgcagctgagacaacgtacgacaaaatattgaaaaacttatccagaaatagaagg
 C  D  A  A  E  T  T  Y  D  K  I  L  K  N  L  S  R  N  R  R
ctggtgagtgacaaagtagggcaggcatgttgcagacccatcgcctttgatgatgacctg
 L  V  S  D  K  V  G  Q  A  C  C  R  P  I  A  F  D  D  D  L
tcgttttagatgataacctggtttaccatattctaagaaagcattccgctaaaaggtgt
 S  F  L  D  D  N  L  V  Y  H  I  L  R  K  H  S  A  K  R  C
ggatgtatctgatctaga
 G  C  I  -
```

Linker peptide is underlined.

Digestion of RAP-GAA with Endo H

1. SDS-PAGE
2. Anti-Iduronidase Western

Figure 10

|           | None | RAP | RAP-Idu (Purified) | RAP-Idu (Medium) |
|-----------|------|-----|--------------------|------------------|
| Anti-RAP  |      | ●   | ●                  | ●                |
| Anti-Idu  |      |     | ●                  | ●                |

Corrected $V_d$ vs. Perfusion time.

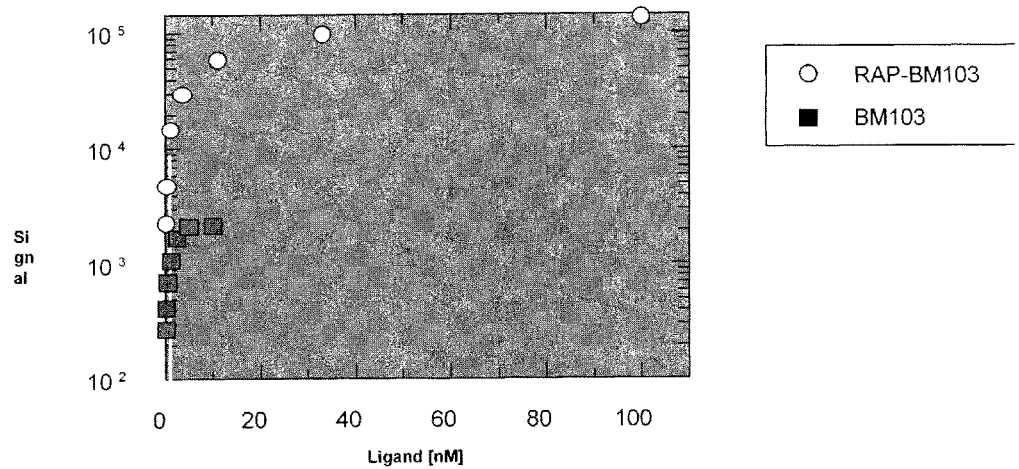
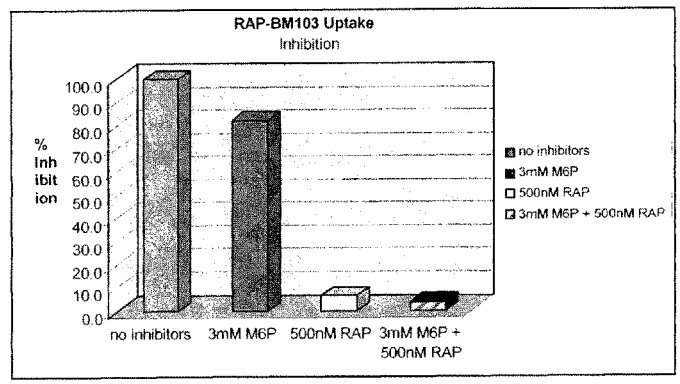
FIGURE 13

FIGURE 14. Multiple alignment of amino acid sequences of RAP from different species.

```
human       1   ------------------------MAPRRVRSFLRGLPALLLLLFLGPWPAASHGGKYSREK
mouse       1   MGGPTRPSPVSLLALQRKMAPRRERVSTLPRLQLLVLLLIPLMLVPQPIAGHGGKYSREK
rat         1   --------------------LRDRVSTLPRLQLLVLLLIPLLLVPQPIAGHGGKYSREK
chicken     1   ------------------------------MGATRTIVAVMAAFLAVSTRASKYTREA
zebrafish   1   ------------------------------------------------MAGKYSKEM
fruit fly   1   ---------------------MVRSALVVAAIALSVIIALQGVDADKKQSKKYSKEA
mosquito    1   -------------ELCPIARRKRGIKHTLTMPLFTRLCVIVFTVLVCNHVVQSEKAHSKY
flatworm    1   ----------------------------------------------MRNHFSFLL
consensus   1                                   t          1 11 1m1      hggkysre human       40  ---------NQPKPSPKRESGEEFRMEKLNQLWEKAQRLHIPPVRLAELHADLKIQERDE
mouse       61  ---------NEPEMAAKRESGEEFRMEKLNQLWEKAKRLHLSPVRLAELHSDLKIQERDE
rat         40  ---------NEPEMAAKRESGEEFRMEKLNQLWEKAKRLHLSPVRLAELHSDLKIQERDE
chicken     29  ---------NEGLADAKRREAGEFRVVRLNQVWEKAQRLQLSAVLAELHSDLKIQEKDE
zebrafish   10  ---------NEKNASDKSNNQVEFRIAKLNQVWEKAIRMQLAPVRLELHSDLKIQEKDE
fruit fly   37  NDPHFQQVKQEKYDPDFKSIQRPFRMAKLNLVWAKAQNR-LTEPKLKSLYMELKIHDKEE
mosquito    48  SKHANALPDSEIYEPDFRNIQRPFRMAKLNLVWTKAQHR-LTEPKLKSLYTELKHDKEE
flatworm    10  ---------FLLVIGSAHNKKTQYRTERINFIYEKALQHVTDRQNLARLEKELSGYDAIY
consensus   61           ne      kr  g efRmeklNqvweKAqrl lspvrLaeLhsdLkiqekde human       91  LAWKKLKLDGLDEDGEKEARLIRNLNVILAKYGLDCKKDARQVTSN-----SLSGTQE--
mouse       112 LNWKKLKVEGLDKDGEKEAKLIHNLNVILARYGLDCRKDAQMVHSN-----ALNEDTQ--
rat         91  LNWKKLKVEGLDGDGEKEAKLVHNLNVILARYGLDCRKDTQTVHSN-----ALNEDTQ--
chicken     80  LSWKKLKAEGLGEDGEKEAKLRRNINVIMTKYGVNGKKDSHLTDTN-----YIKDGTES-
zebrafish   61  LQWKKLKAEGMDEDGEREAKLRRNFNIILAKYGMDGKKDTRTLDSNR---LKDHEVKIG-
fruit fly   96  IAWKQLNSQHKDKDGLKADELRRKIIGIMSSVDLLEHFDDTQDTEKLKPYKKFHDAEER-
mosquito    107 ITYKQLK--EKDKDGLKEAELRNKLVSIMSIYGLLEHFDDTQDPEKYKLAKSSDGAPKKD
flatworm    61  LASKSNR--QGTQGTKEIDKIDDKLGKILEKYGLEKAVLAFKEKYKHKNLFQQTDDNEP-
consensus   121 l wKklk egld dgekeaklrrnlnvIlakYgldgkkd    v sn       l e  e human       144 -----DGLDDPRLEKLWHKAKTSGKFSGEELDKLWREFLHHKEKVHEYNVLLETLS----
mouse       165 -----DELGDPRLEKLWHKAKTSGKFSSEELDKLWREFLHYKEKIQEYNVLLDTLS----
rat         144 -----DELGDPRLEKLWHKAKTSGKFSSEELDKLWREFLHYKEKIHEYNVLLDTLS----
chicken     134 -----DTLDDPRLEKLWSKAKTSGKFSDEELDKLWREFKHHKEKIREYNILLETVS----
zebrafish   117 -----DTFDDPKLDKLWNKARTSGKFSDEELQTLHREFQHHKDKIHEYNIVMDTVS----
fruit fly   155 -HRNKSLFKDKKLNLWEKAEISG-FTABELKSLKQEFDHHQDKVDVYYSLIENIG----
mosquito    165 TYKNKSLFKDKKLNKLWDKAESAG-ETKEELDAIREEFDHHQAKIDVYYSLLERIGDDDD
flatworm    118 --LPSGKFTDQNLQKLWSQAQNGK-FSQKEINALHGELKEVEQKMRVYEDQLDDFK----
consensus   181        d   DprLekLW kAktsgkFs eELdkLwrEf hhkeKiheYnvlletls human       195 --------RTEEIHENVISPSDLS-----------DIKGSVLHSRHTELKEKL
mouse       216 --------RAEEGYENLLSPSDMA-----------HIKSDTLISKHSELKDRL
rat         195 --------RAEEGYENLLSPSDMT-----------HIKSDTLASKHSELKDRL
chicken     185 --------RTEDIHKKVINPSEEN-----------PVKEEVLHNKHRELKEKL
zebrafish   168 --------RTEEIHKNVISELEG-----------DVKENVLHQKHTDLKQRM
fruit fly   209 --------TVDTDKHENAINTEDLDTYNLISNDVNENDIKTHAQNVKSFENDLNTLRGHH
mosquito    224 GGAAGQGSRRDDDALLNAVNDEEHDRYNEVDRAEETDRSQPGANKQHAYLHKSNQLREKH
flatworm    171 --------K--VPHENSIQHDIES-----------IG----DKTKKLKAAN
consensus   241          r ee henvispsdl                 ik   l   khteLkekl
```

Figure 14A

```
human      229 RSINQGLDRLRRVSHQGYSTEAEFEEPRVIDLWDLAQSA-NLTDKELEAFREELKHFEAK
mouse      250 RSINQGLDRLRKVSHQGYGSTTEFEEPRVIDLWDLAQSA-NFTEKELESFREELKHFEAK
rat        229 RSINQGLDRLRKVSHQGYGPATEFEEPRVIDLWDLAQSA-NFTEKELESFREELKHFEAK
chicken    219 RSINQGFERLRKVSHQGYDATSEFEEPRVIDLWDMAKSA-NFTEKELESFREELKHFEAK
zebrafish  201 RDINQGFERLRKITHEGYTDDSEFREPRVIELWEMAKRS-NLSEDELDSLKEELRHFETK
fruit fly  261 TGIKDHYDRLERLVSSGPHSQ-DFIEPKVQGLWRVAQAS-NFTVKELESIKTELHHFESR
mosquito   284 REIRDNFDRLDRIASKGPKSQ-DFVEPKVQGLWRVALAS-DFSADELASLKVELLH ESR
flatworm   197 REINDHLDEVHRKVTSEEFSP--FNEPRVKRLWKLAQENEKLTPHELSVLKDELSHFESQ
consensus  301 rsinqgldrlrrvshqgy s teFeEPrVidLWdlAqsa nftekELesfreELkHfEak human      288 IEKHNHYQKQLEIAHEKLRHAES-----VGDGERVSRSREKHALLEGRTKELGYTVKKHL
mouse      309 IEKHNHYQKQLEISHQKLKHVES-----IGDPEHISRNKEKYVLLEEKTKELGYKVKKHL
rat        288 IEKHNHYQKQLEISHQKLKHVES-----IGDPEHISRNKEKYVLLEEKTKELGYKVKKHL
chicken    278 IEKHHHYQKQLEISHEKLKHIEG-----TGDKEHLNRNREKYAMLEEKTKELGYKVKKHL
zebrafish  260 VEKHQHYQEQLELSHQKLKHVEA-----LGDEDHIMRNKEKYNTLAEKAREMGYKVKKHL
fruit fly  319 LLKLRHLHAEHALQKEKYKGEK------------VKDKSSRFEEMEDQLKKQTRKVEKLQ
mosquito   342 LLKLRHMHAEHAISLEKHKHS-------------DAKADTHKLMEDNIKKQTRKVEKMQ
flatworm   255 LKKIEFHKVFFFVANSCPKRGKNEEVSRLQEDAEERGKDKSQVYENLELSIKHEKLNRKA
consensus  361 ieKhnhyqkqleisheklkhve      vgd ehv rnreky lleektkelgykvkkhl human      343 QDLSGRISR--ARHNEL
mouse      364 QDLSSRVSR--ARHNEL
rat        343 QDLSSRVSR--ARHNEL
chicken    333 QDLSSRISQG-LQHNEL
zebrafish  315 QDLTNKLSKNGLQHNEL
fruit fly  367 ENIEKTIFK----HTEL
mosquito   388 EEVERRIFK----HSEL
flatworm   315 RKLEKYIEEKIIIHREL
consensus  421 qdls risr    HnEL
```

Figure 14B

Figure 15: SEQ ID NO: 1:

TyrSerArgGluLysAsnGlnProLysProSerProLysArgGluSer
GlyGluGluPheArgMetGluLysLeuAsnGlnLeuTrpGluLysAla
GlnArgLeuHisLeuProProValArgLeuAlaGluLeuHisAlaAsp
LeuLysIleGlnGluArgAspGluLeuAl aTrpLysLysLeuLysLeu
AspGlyLeuAspGluAspGlyGluLysGluAlaArgLeuIleArgAsn
LeuAsnValIleLeuAlaLysTyrGlyLeuAspGlyLysLysAspAla
ArgGlnValThrSerAsnSerLeuSerGlyThrGlnGluAspGly Leu
AspAspProArgLeuGluLysLeuTrpHisLysAlaLysThrSerGly
LysPheSerG lyGluGluLeuAspLysLeuTrpArgGluPheLeuHis
HisLysGluLysValHisGluTyrAsnValLeuLeuGluThrLeuSer
ArgThrGluGluIleHisGluAsnValIleSerProSerAspLeuSer
AspIleLysGlySerValLeuHisSe rArgHisThrGluLeuLysGlu
LysLeuArgSerIleAsnGlnGlyLeuAspArgLeuArgArgValSer
HisGlnGlyTyrSerThrGluAlaGluPheGluGluProArgValIle
AspLeuTrpAspLeuAlaGlnSerAlaAsnLeuThrAspLysGluLeu
GluAlaPheArgGluGluLeuLysHisPheGluAlaLysIleGluLys
HisAsnH isTyrGlnLysGlnLeuGluIleAlaHisGluLysLeuArg
HisAlaGluSerValGlyAspGlyGluArgValSerArgSerArgGlu
LysHisAlaLeuLeuGluGlyArgThrLysGluLeuGlyTyrThrVal
LysLysHisLeuGlnAspLeuSerGlyArgIleSe rArgAlaArgHis
AsnGluLeu

Figure 16: SEQ ID NO: 2:

ProArgLeuGluLysLeuTrpHisLysAlaLysThrSerGlyLysPhe
SerGlyGluGluLeuAspLysLeuTrpArgGluPheLeu HisHisLys
GluLysValHisGluTyrAsnValLeuLeuGluThrLeuSerArgThr
GluG luIleHisGluAsnValIleSerProSerAspLeuSerAspIle
LysGlySerValLeuHisSerArgHisThrGluLeuLysGluLysLeu
ArgSerIleAsnGlnGlyLeuAspArgLeuArgArgValSerHisGln
GlyTyrSerThrGluAlaGl uPheGluGluProArgValIleAspLeu
TrpAspLeuAlaGlnSerAlaAsnLeuThrAspLysGluLeuGluAla
PheArgGluGluLeuLysHisPheGluAlaLysIleGluLysHisAsn
HisTyrGlnLysGlnLeuGluIleAlaHisGluLysLeuArgHisAla
GluSerValGlyAspGlyGluArgValSerArgSerArgGluLysHis
A laLeuLeuGluGlyArgThrLysGluLeuGlyTyrThrValLysLys
HisLeuGlnAspLeuSerGlyArgIleSerArgAlaArgHisAsnGlu
Leu

Figure 17
Transport assays in BBCEC monolayers
A. Transcytosis
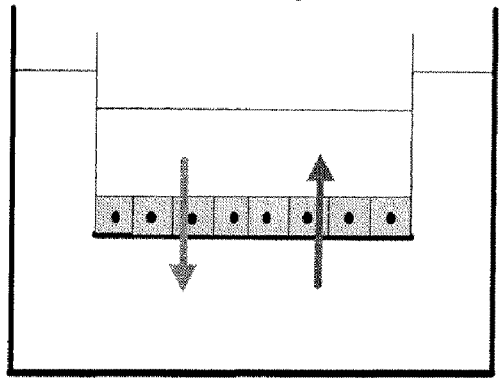
B. Uptake
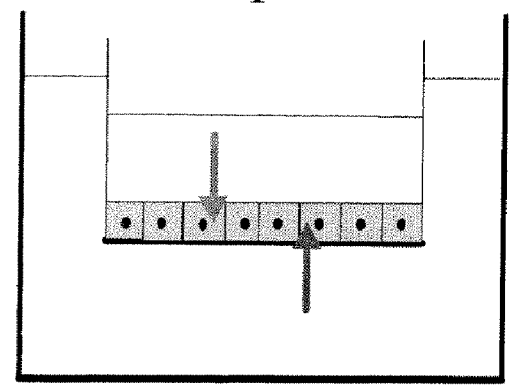

SEQUENCE LISTING

```
<160> NUMBER OF SEQ ID NOS: 29

<210> SEQ ID NO 1
<211> LENGTH: 323
<212> TYPE: PRT
<213> ORGANISM: Homo sapiens

<400> SEQUENCE: 1

Tyr Ser Arg Glu Lys Asn Gln Pro Lys Pro Ser Pro Lys Arg Glu Ser
1               5                   10                  15

Gly Glu Glu Phe Arg Met Glu Lys Leu Asn Gln Leu Trp Glu Lys Ala
```

-continued

```
                20                  25                  30
Gln Arg Leu His Leu Pro Pro Val Arg Leu Ala Glu Leu His Ala Asp
         35                  40                  45

Leu Lys Ile Gln Glu Arg Asp Glu Leu Ala Trp Lys Lys Leu Lys Leu
 50                  55                  60

Asp Gly Leu Asp Glu Asp Gly Glu Lys Glu Ala Arg Leu Ile Arg Asn
 65                  70                  75                  80

Leu Asn Val Ile Leu Ala Lys Tyr Gly Leu Asp Gly Lys Lys Asp Ala
                 85                  90                  95

Arg Gln Val Thr Ser Asn Ser Leu Ser Gly Thr Gln Glu Asp Gly Leu
                100                 105                 110

Asp Asp Pro Arg Leu Glu Lys Leu Trp His Lys Ala Lys Thr Ser Gly
                115                 120                 125

Lys Phe Ser Gly Glu Glu Leu Asp Lys Leu Trp Arg Glu Phe Leu His
                130                 135                 140

His Lys Glu Lys Val His Glu Tyr Asn Val Leu Leu Glu Thr Leu Ser
145                 150                 155                 160

Arg Thr Glu Glu Ile His Glu Asn Val Ile Ser Pro Ser Asp Leu Ser
                165                 170                 175

Asp Ile Lys Gly Ser Val Leu His Ser Arg His Thr Glu Leu Lys Glu
                180                 185                 190

Lys Leu Arg Ser Ile Asn Gln Gly Leu Asp Arg Leu Arg Arg Val Ser
                195                 200                 205

His Gln Gly Tyr Ser Thr Glu Ala Glu Phe Glu Glu Pro Arg Val Ile
                210                 215                 220

Asp Leu Trp Asp Leu Ala Gln Ser Ala Asn Leu Thr Asp Lys Glu Leu
225                 230                 235                 240

Glu Ala Phe Arg Glu Glu Leu Lys His Phe Glu Ala Lys Ile Glu Lys
                245                 250                 255

His Asn His Tyr Gln Lys Gln Leu Glu Ile Ala His Glu Lys Leu Arg
                260                 265                 270

His Ala Glu Ser Val Gly Asp Gly Glu Arg Val Ser Arg Ser Arg Glu
                275                 280                 285

Lys His Ala Leu Leu Glu Gly Arg Thr Lys Glu Leu Gly Tyr Thr Val
                290                 295                 300

Lys Lys His Leu Gln Asp Leu Ser Gly Arg Ile Ser Arg Ala Arg His
305                 310                 315                 320

Asn Glu Leu

<210> SEQ ID NO 2
<211> LENGTH: 209
<212> TYPE: PRT
<213> ORGANISM: Homo sapiens

<400> SEQUENCE: 2

Pro Arg Leu Glu Lys Leu Trp His Lys Ala Lys Thr Ser Gly Lys Phe
 1               5                  10                  15

Ser Gly Glu Glu Leu Asp Lys Leu Trp Arg Glu Phe Leu His His Lys
                20                  25                  30

Glu Lys Val His Glu Tyr Asn Val Leu Leu Glu Thr Leu Ser Arg Thr
                35                  40                  45

Glu Glu Ile His Glu Asn Val Ile Ser Pro Ser Asp Leu Ser Asp Ile
 50                  55                  60

Lys Gly Ser Val Leu His Ser Arg His Thr Glu Leu Lys Glu Lys Leu
```

```
                65                  70                  75                  80
Arg Ser Ile Asn Gln Gly Leu Asp Arg Leu Arg Arg Val Ser His Gln
                    85                  90                  95
Gly Tyr Ser Thr Glu Ala Glu Phe Glu Glu Pro Arg Val Ile Asp Leu
                100                 105                 110
Trp Asp Leu Ala Gln Ser Ala Asn Leu Thr Asp Lys Glu Leu Glu Ala
                115                 120                 125
Phe Arg Glu Glu Leu Lys His Phe Glu Ala Lys Ile Glu Lys His Asn
            130                 135                 140
His Tyr Gln Lys Gln Leu Glu Ile Ala His Glu Lys Leu Arg His Ala
145                 150                 155                 160
Glu Ser Val Gly Asp Gly Glu Arg Val Ser Arg Ser Arg Glu Lys His
                165                 170                 175
Ala Leu Leu Glu Gly Arg Thr Lys Glu Leu Gly Tyr Thr Val Lys Lys
                180                 185                 190
His Leu Gln Asp Leu Ser Gly Arg Ile Ser Arg Ala Arg His Asn Glu
                195                 200                 205
Leu

<210> SEQ ID NO 3
<211> LENGTH: 33
<212> TYPE: DNA
<213> ORGANISM: Artificial sequence
<220> FEATURE:
<223> OTHER INFORMATION: Synthetic primer

<400> SEQUENCE: 3
ccgcgtggat cccccaggct ggaaaagctg tgg                            33

<210> SEQ ID NO 4
<211> LENGTH: 35
<212> TYPE: DNA
<213> ORGANISM: Artificial sequence
<220> FEATURE:
<223> OTHER INFORMATION: Synthetic primer

<400> SEQUENCE: 4
tcaatgaatt ctcagagttc gttgtgccga gctct                          35

<210> SEQ ID NO 5
<211> LENGTH: 205
<212> TYPE: PRT
<213> ORGANISM: Homo sapiens

<400> SEQUENCE: 5

Pro Arg Leu Glu Lys Leu Trp His Lys Ala Lys Thr Ser Gly Ile Ser
1               5                   10                  15
Val Arg Leu Thr Ser Cys Ala Arg Val Leu His Tyr Lys Glu Lys Ile
                20                  25                  30
His Glu Tyr Asn Val Leu Leu Asp Thr Leu Ser Arg Ala Glu Glu Gly
            35                  40                  45
Tyr Glu Asn Leu Leu Ser Pro Ser Asp Met Thr His Ile Lys Ser Asp
    50                  55                  60
Thr Leu Ala Ser Lys His Ser Glu Leu Lys Asp Arg Leu Arg Ser Ile
65                  70                  75                  80
Asn Gln Gly Leu Asp Arg Leu Arg Lys Val Ser His Gln Leu Arg Pro
                85                  90                  95
Ala Thr Glu Phe Glu Glu Pro Arg Val Ile Asp Leu Trp Asp Leu Ala
```

```
                100                 105                 110
Gln Ser Ala Asn Phe Thr Glu Lys Glu Leu Glu Ser Phe Arg Glu Glu
            115                 120                 125

Leu Lys His Phe Glu Ala Lys Ile Glu Lys His Asn His Tyr Gln Lys
        130                 135                 140

Gln Leu Glu Ile Ser His Gln Lys Leu Lys His Val Glu Ser Ile Gly
145                 150                 155                 160

Asp Pro Glu His Ile Ser Arg Asn Lys Glu Lys Tyr Val Leu Leu Glu
                165                 170                 175

Glu Lys Thr Lys Glu Leu Gly Tyr Lys Val Lys His Leu Gln Asp
            180                 185                 190

Leu Ser Ser Arg Val Ser Arg Ala Arg His Asn Glu Leu
        195                 200                 205

<210> SEQ ID NO 6
<211> LENGTH: 3702
<212> TYPE: DNA
<213> ORGANISM: Artificial sequence
<220> FEATURE:
<223> OTHER INFORMATION: RAP-GAA fusion sequence

<400> SEQUENCE: 6
```

| | | | | | |
|---|---|---|---|---|---|
| cttaccgcca | tgcggggtcc | gagcggggct | ctgtggctgc | tcctggctct | gcgcaccgtg | 60 |
| ctcggatcct | actcgcggga | gaagaaccag | cccaagccgt | ccccgaaacg | cgagtccgga | 120 |
| gaggagttcc | gcatggagaa | gttgaaccag | ctgtgggaga | aggcccagcg | actgcatctt | 180 |
| cctcccgtga | ggctggccga | gctccacgct | gatctgaaga | tacaggagag | ggacgaactc | 240 |
| gcctggaaga | aactaaagct | tgacggcttg | gacgaagatg | gggagaagga | agcgagactc | 300 |
| atacgcaacc | tcaatgtcat | cttggccaag | tatggtctgg | acggaaagaa | ggacgctcgg | 360 |
| caggtgacca | gcaactccct | cagtggcacc | caggaagacg | ggctggatga | ccccaggctg | 420 |
| gaaaagctgt | ggcacaaggc | gaagacctct | gggaaattct | ccggcgaaga | actggacaag | 480 |
| ctctggcggg | agttcctgca | tcacaaagag | aaagttcacg | agtacaacgt | cctgctggag | 540 |
| accctgagca | ggaccgaaga | aatccacgag | aacgtcatta | gccctcgga | cctgagcgac | 600 |
| atcaagggca | gcgtcctgca | cagcaggcac | acggagctga | aggagaagct | gcgcagcatc | 660 |
| aaccagggcc | tggaccgcct | cgcagggtc | agccaccagg | gctacagcac | tgaggctgag | 720 |
| ttcgaggagc | ccagggtgat | tgacctgtgg | gacctggcgc | agtccgccaa | cctcacggac | 780 |
| aaggagctgg | aggcgttccg | ggaggagctc | aagcacttcg | aagccaaaat | cgagaagcac | 840 |
| aaccactacc | agaagcagct | ggagattgcg | cacgagaagc | tgaggcacgc | agagagcgtg | 900 |
| ggcgacggcg | agcgtgtgag | ccgcagccgc | gagaagcacg | ccctgctgga | ggggcggacc | 960 |
| aaggagctgg | gctacacggt | gaagaagcat | ctgcaggacc | tgtccggcag | gatctccaga | 1020 |
| gctcgcgccg | aggcagaaac | cggtgcacac | cccggccgtc | ccagagcagt | gcccacacag | 1080 |
| tgcgacgtcc | ccccaacag | ccgcttcgat | tgcgcccctg | acaaggccat | cacccaggaa | 1140 |
| cagtgcgagg | cccgcggctg | ctgctacatc | cctgcaaagc | aggggctgca | gggagcccag | 1200 |
| atggggcagc | cctggtgctt | cttcccaccc | agctaccca | gctacaagct | ggagaacctg | 1260 |
| agctcctctg | aaatgggcta | cacgccacc | ctgacccgta | ccaccccac | cttcttcccc | 1320 |
| aaggacatcc | tgaccctgcg | gctggacgtg | atgatggaga | ctgagaaccg | cctccacttc | 1380 |
| acgatcaaag | atccagctaa | caggcgctac | gaggtgccct | tggagacccc | gcgtgtccac | 1440 |
| agccgggcac | cgtcccact | ctacagcgtg | gagttctccg | aggagcccct | tcggggtgatc | 1500 |

```
gtgcaccggc agctggacgg ccgcgtgctg ctgaacacga cggtggcgcc cctgttcttt    1560
gcggaccagt tccttcagct gtccacctcg ctgccctcgc agtatatcac aggcctcgcc    1620
gagcacctca gtcccctgat gctcagcacc agctggacca ggatcaccct gtggaaccgg    1680
gaccttgcgc ccacgcccgg tgcgaacctc tacgggtctc acccttttcta cctggcgctg    1740 gaggacggcg gtcggcaca cggggtgttc ctgctaaaca gcaatgccat ggatgtggtc    1800
ctgcagccga gccctgccct tagctggagg tcgacaggtg ggatcctgga tgtctacatc    1860
ttcctgggcc cagagcccaa gagcgtggtg cagcagtacc tggacgttgt gggatacccg    1920
ttcatgccgc catactgggg cctgggcttc cacctgtgcc gctggggcta ctcctccacc    1980
gctatcaccc gccaggtggt ggagaacatg accagggccc acttccccct ggacgtccaa    2040
tggaacgacc tggactacat ggactcccgg agggacttca cgttcaacaa ggatggcttc    2100
cgggacttcc cggccatggt gcaggagctg caccagggcg gccggcgcta catgatgatc    2160
gtggatcctg ccatcagcag ctcgggccct gccgggagct acaggcccta cgacgagggt    2220
ctgcggaggg gggttttcat caccaacgag accggccagc cgctgattgg gaaggtatgg    2280
cccgggtcca ctgccttccc cgacttcacc aaccccacag ccctggcctg gtgggaggac    2340
atggtggctg agttccatga ccaggtgccc ttcgacggct tgtggattga catgaacgag    2400
ccttccaact tcatcagagg ctctgaggac ggctgcccca caatgagct ggagaaccca    2460 ccctacgtgc ctgggtggt tgggggggacc ctccaggcgg ccaccatctg tgcctccagc    2520
caccagtttc tctccacaca ctacaacctg cacaacctct acggcctgac cgaagccatc    2580
gcctcccaca gggcgctggt gaaggctcgg gggacacgcc catttgtgat ctcccgctcg    2640
acctttgctg ccacggccg atacgccggc cactggacgg gggacgtgtg gagctcctgg    2700
gagcagctcg cctcctccgt gccagaaatc ctgcagttta acctgctggg ggtgcctctg    2760
gtcggggccg acgtctgcgg cttcctgggc aacacctcag aggagctgtg tgtgcgctgg    2820
acccagctgg gggccttcta cccccttcatg cggaaccaca acagcctgct cagtctgccc    2880
caggagccgt acagcttcag cgagccggcc cagcaggcca tgaggaaggc cctcacccctg    2940 cgctacgcac tcctcccccca cctctacaca ctgttccacc aggcccacgt cgcgggggag    3000
accgtggccc ggcccctctt cctggagttc cccaaggact ctagcacctg gactgtggac    3060
caccagctcc tgtgggggga ggccctgctc atcaccccag tgctccaggc cgggaaggcc    3120
gaagtgactg gctacttccc cttgggcaca tggtacgacc tgcagacggt gccaatagag    3180
gcccttggca gcctcccacc cccacctgca gctccccgtg agccagccat ccacagcgag    3240
gggcagtggg tgacgctgcc ggccccctg gacaccatca cgtccacct ccgggctggg    3300 tacatcatcc ccctgcaggg ccctggcctc acaaccacag agtcccgcca gcagcccatg    3360
gccctggctg tggccctaac caagggtgga gaggcccgag gggagctgtt ctgggacgat    3420
ggagagagcc tggaagtgct ggagcgaggg gcctacacac aggtcatctt cctggccagg    3480
aataacacga tcgtgaatga gctggtacgt gtgaccagtg agggagctgg cctgcagctg    3540
cagaaggtga ctgtcctggg cgtggccacg gcgccccagc aggtcctctc caacggtgtc    3600
cctgtctcca acttcaccta cagccccgac accaaggtcc tggacatctg tgtctcgctg    3660
ttgatgggag agcagtttct cgtcagctgg tgttgactcg ag                       3702

<210> SEQ ID NO 7
<211> LENGTH: 1228
<212> TYPE: PRT
```

<213> ORGANISM: Artificial sequence
<220> FEATURE:
<223> OTHER INFORMATION: RAP-GAA fusion sequence

<400> SEQUENCE: 7

```
Met Arg Gly Pro Ser Gly Ala Leu Trp Leu Leu Ala Leu Arg Thr
1               5                   10                  15

Val Leu Gly Ser Tyr Ser Arg Glu Lys Asn Gln Pro Lys Pro Ser Pro
            20                  25                  30

Lys Arg Glu Ser Gly Glu Glu Phe Arg Met Glu Lys Leu Asn Gln Leu
        35                  40                  45

Trp Glu Lys Ala Gln Arg Leu His Leu Pro Pro Val Arg Leu Ala Glu
    50                  55                  60

Leu His Ala Asp Leu Lys Ile Gln Glu Arg Asp Glu Leu Ala Trp Lys
65                  70                  75                  80

Lys Leu Lys Leu Asp Gly Leu Asp Glu Asp Gly Glu Lys Glu Ala Arg
                85                  90                  95

Leu Ile Arg Asn Leu Asn Val Ile Leu Ala Lys Tyr Gly Leu Asp Gly
            100                 105                 110

Lys Lys Asp Ala Arg Gln Val Thr Ser Asn Ser Leu Ser Gly Thr Gln
        115                 120                 125

Glu Asp Gly Leu Asp Asp Pro Arg Leu Glu Lys Leu Trp His Lys Ala
    130                 135                 140

Lys Thr Ser Gly Lys Phe Ser Gly Glu Glu Leu Asp Lys Leu Trp Arg
145                 150                 155                 160

Glu Phe Leu His His Lys Glu Lys Val His Glu Tyr Asn Val Leu Leu
                165                 170                 175

Glu Thr Leu Ser Arg Thr Glu Glu Ile His Glu Asn Val Ile Ser Pro
            180                 185                 190

Ser Asp Leu Ser Asp Ile Lys Gly Ser Val Leu His Ser Arg His Thr
        195                 200                 205

Glu Leu Lys Glu Lys Leu Arg Ser Ile Asn Gln Gly Leu Asp Arg Leu
    210                 215                 220

Arg Arg Val Ser His Gln Gly Tyr Ser Thr Glu Ala Glu Phe Glu Glu
225                 230                 235                 240

Pro Arg Val Ile Asp Leu Trp Asp Leu Ala Gln Ser Ala Asn Leu Thr
                245                 250                 255

Asp Lys Glu Leu Glu Ala Phe Arg Glu Glu Leu Lys His Phe Glu Ala
            260                 265                 270

Lys Ile Glu Lys His Asn His Tyr Gln Lys Gln Leu Glu Ile Ala His
        275                 280                 285

Glu Lys Leu Arg His Ala Glu Ser Val Gly Asp Gly Glu Arg Val Ser
    290                 295                 300

Arg Ser Arg Glu Lys His Ala Leu Leu Glu Gly Arg Thr Lys Glu Leu
305                 310                 315                 320

Gly Tyr Thr Val Lys Lys His Leu Gln Asp Leu Ser Gly Arg Ile Ser
                325                 330                 335

Arg Ala Arg Ala Glu Ala Glu Thr Gly Ala His Pro Gly Arg Pro Arg
            340                 345                 350

Ala Val Pro Thr Gln Cys Asp Val Pro Pro Asn Ser Arg Phe Asp Cys
        355                 360                 365

Ala Pro Asp Lys Ala Ile Thr Gln Glu Gln Cys Glu Ala Arg Gly Cys
    370                 375                 380

Cys Tyr Ile Pro Ala Lys Gln Gly Leu Gln Gly Ala Gln Met Gly Gln
```

-continued

```
            385                 390                 395                 400
Pro Trp Cys Phe Phe Pro Pro Ser Tyr Pro Ser Tyr Lys Leu Glu Asn
                405                 410                 415
Leu Ser Ser Ser Glu Met Gly Tyr Thr Ala Thr Leu Thr Arg Thr Thr
                420                 425                 430
Pro Thr Phe Phe Pro Lys Asp Ile Leu Thr Leu Arg Leu Asp Val Met
                435                 440                 445
Met Glu Thr Glu Asn Arg Leu His Phe Thr Ile Lys Asp Pro Ala Asn
            450                 455                 460
Arg Arg Tyr Glu Val Pro Leu Glu Thr Pro Arg Val His Ser Arg Ala
465                 470                 475                 480
Pro Ser Pro Leu Tyr Ser Val Glu Phe Ser Glu Pro Phe Gly Val
                485                 490                 495
Ile Val His Arg Gln Leu Asp Gly Arg Val Leu Leu Asn Thr Thr Val
                500                 505                 510
Ala Pro Leu Phe Phe Ala Asp Gln Phe Leu Gln Leu Ser Thr Ser Leu
                515                 520                 525
Pro Ser Gln Tyr Ile Thr Gly Leu Ala Glu His Leu Ser Pro Leu Met
                530                 535                 540
Leu Ser Thr Ser Trp Thr Arg Ile Thr Leu Trp Asn Arg Asp Leu Ala
545                 550                 555                 560
Pro Thr Pro Gly Ala Asn Leu Tyr Gly Ser His Pro Phe Tyr Leu Ala
                565                 570                 575
Leu Glu Asp Gly Gly Ser Ala His Gly Val Phe Leu Leu Asn Ser Asn
                580                 585                 590
Ala Met Asp Val Val Leu Gln Pro Ser Pro Ala Leu Ser Trp Arg Ser
                595                 600                 605
Thr Gly Gly Ile Leu Asp Val Tyr Ile Phe Leu Gly Pro Glu Pro Lys
                610                 615                 620
Ser Val Val Gln Gln Tyr Leu Asp Val Val Gly Tyr Pro Phe Met Pro
625                 630                 635                 640
Pro Tyr Trp Gly Leu Gly Phe His Leu Cys Arg Trp Gly Tyr Ser Ser
                645                 650                 655
Thr Ala Ile Thr Arg Gln Val Val Glu Asn Met Thr Arg Ala His Phe
                660                 665                 670
Pro Leu Asp Val Gln Trp Asn Asp Leu Asp Tyr Met Asp Ser Arg Arg
                675                 680                 685
Asp Phe Thr Phe Asn Lys Asp Gly Phe Arg Asp Phe Pro Ala Met Val
                690                 695                 700
Gln Glu Leu His Gln Gly Gly Arg Arg Tyr Met Met Ile Val Asp Pro
705                 710                 715                 720
Ala Ile Ser Ser Ser Gly Pro Ala Gly Ser Tyr Arg Pro Tyr Asp Glu
                725                 730                 735
Gly Leu Arg Arg Gly Val Phe Ile Thr Asn Glu Thr Gly Gln Pro Leu
                740                 745                 750
Ile Gly Lys Val Trp Pro Gly Ser Thr Ala Phe Pro Asp Phe Thr Asn
                755                 760                 765
Pro Thr Ala Leu Ala Trp Trp Glu Asp Met Val Ala Glu Phe His Asp
                770                 775                 780
Gln Val Pro Phe Asp Gly Leu Trp Ile Asp Met Asn Glu Pro Ser Asn
785                 790                 795                 800
Phe Ile Arg Gly Ser Glu Asp Gly Cys Pro Asn Asn Glu Leu Glu Asn
                805                 810                 815
```

-continued

```
Pro Pro Tyr Val Pro Gly Val Val Gly Gly Thr Leu Gln Ala Ala Thr
        820             825                 830

Ile Cys Ala Ser Ser His Gln Phe Leu Ser Thr His Tyr Asn Leu His
        835                 840                 845

Asn Leu Tyr Gly Leu Thr Glu Ala Ile Ala Ser His Arg Ala Leu Val
    850                 855                 860

Lys Ala Arg Gly Thr Arg Pro Phe Val Ile Ser Arg Ser Thr Phe Ala
865                 870                 875                 880

Gly His Gly Arg Tyr Ala Gly His Trp Thr Gly Asp Val Trp Ser Ser
                885                 890                 895

Trp Glu Gln Leu Ala Ser Ser Val Pro Glu Ile Leu Gln Phe Asn Leu
        900                 905                 910

Leu Gly Val Pro Leu Val Gly Ala Asp Val Cys Gly Phe Leu Gly Asn
            915                 920                 925

Thr Ser Glu Glu Leu Cys Val Arg Trp Thr Gln Leu Gly Ala Phe Tyr
    930                 935                 940

Pro Phe Met Arg Asn His Asn Ser Leu Leu Ser Leu Pro Gln Glu Pro
945                 950                 955                 960

Tyr Ser Phe Ser Glu Pro Ala Gln Gln Ala Met Arg Lys Ala Leu Thr
                965                 970                 975

Leu Arg Tyr Ala Leu Leu Pro His Leu Tyr Thr Leu Phe His Gln Ala
            980                 985                 990

His Val Ala Gly Glu Thr Val Ala Arg Pro Leu Phe Leu Glu Phe Pro
        995                 1000                 1005

Lys Asp Ser Ser Thr Trp Thr Val Asp His Gln Leu Leu Trp Gly
    1010                 1015                 1020

Glu Ala Leu Leu Ile Thr Pro Val Leu Gln Ala Gly Lys Ala Glu
    1025                 1030                 1035

Val Thr Gly Tyr Phe Pro Leu Gly Thr Trp Tyr Asp Leu Gln Thr
    1040                 1045                 1050

Val Pro Ile Glu Ala Leu Gly Ser Leu Pro Pro Pro Pro Ala Ala
    1055                 1060                 1065

Pro Arg Glu Pro Ala Ile His Ser Glu Gly Gln Trp Val Thr Leu
    1070                 1075                 1080

Pro Ala Pro Leu Asp Thr Ile Asn Val His Leu Arg Ala Gly Tyr
    1085                 1090                 1095

Ile Ile Pro Leu Gln Gly Pro Gly Leu Thr Thr Thr Glu Ser Arg
    1100                 1105                 1110

Gln Gln Pro Met Ala Leu Ala Val Ala Leu Thr Lys Gly Gly Glu
    1115                 1120                 1125

Ala Arg Gly Glu Leu Phe Trp Asp Asp Gly Glu Ser Leu Glu Val
    1130                 1135                 1140

Leu Glu Arg Gly Ala Tyr Thr Gln Val Ile Phe Leu Ala Arg Asn
    1145                 1150                 1155

Asn Thr Ile Val Asn Glu Leu Val Arg Val Thr Ser Glu Gly Ala
    1160                 1165                 1170

Gly Leu Gln Leu Gln Lys Val Thr Val Leu Gly Val Ala Thr Ala
    1175                 1180                 1185

Pro Gln Gln Val Leu Ser Asn Gly Val Pro Val Ser Asn Phe Thr
    1190                 1195                 1200

Tyr Ser Pro Asp Thr Lys Val Leu Asp Ile Cys Val Ser Leu Leu
    1205                 1210                 1215
```

```
Met Gly Glu Gln Phe Leu Val Ser Trp Cys
    1220            1225
```

```
<210> SEQ ID NO 8
<211> LENGTH: 2937
<212> TYPE: DNA
<213> ORGANISM: Artificial sequence
<220> FEATURE:
<223> OTHER INFORMATION: RAP-IDU fusion sequence

<400> SEQUENCE: 8
```

| | | | | |
|---|---|---|---|---|
| aagcttaccg | ccatgcgggg | tccgagcggg | gctctgtggc | tgctcctggc tctgcgcacc | 60 |
| gtgctcggat | cctactcgcg | ggagaagaac | cagcccaagc | cgtccccgaa acgcgagtcc | 120 |
| ggagaggagt | tccgcatgga | gaagttgaac | cagctgtggg | agaaggccca gcgactgcat | 180 |
| cttcctcccg | tgaggctggc | cgagctccac | gctgatctga | agatacagga gagggacgaa | 240 |
| ctcgcctgga | agaaactaaa | gcttgacggc | ttggacgaag | atggggagaa ggaagcgaga | 300 |
| ctcatacgca | acctcaatgt | catcttggcc | aagtatggtc | tggacggaaa gaaggacgct | 360 |
| cggcaggtga | ccagcaactc | cctcagtggc | acccaggaag | acgggctgga tgaccccagg | 420 |
| ctggaaaagc | tgtgcacaa | ggcgaagacc | tctgggaaat | tctccggcga agaactggac | 480 |
| aagctctggc | gggagttcct | gcatcacaaa | gagaaagttc | acgagtacaa cgtcctgctg | 540 |
| gagaccctga | gcaggaccga | gaaaatccac | gagaacgtca | ttagcccctc ggacctgagc | 600 |
| gacatcaagg | gcagcgtcct | gcacagcagg | cacgagc | tgaaggagaa gctgcgcagc | 660 |
| atcaaccagg | gcctggaccg | cctgcgcagg | gtcagccacc | agggctacag cactgaggct | 720 |
| gagttcgagg | agcccagggt | gattgacctg | tgggacctgg | cgcagtccgc caacctcacg | 780 |
| gacaaggagc | tggaggcgtt | ccgggaggag | ctcaagcact | cgaagccaa atcgagaag | 840 |
| cacaaccact | accagaagca | gctggagatt | gcgcacgaga | agctgaggca cgcagagagc | 900 |
| gtgggcgacg | cgagcgtgt | gagccgcagc | cgcgagaagc | acgccctgct ggaggggcgg | 960 |
| accaaggagc | tgggctacac | ggtgaagaag | catctgcagg | acctgtccgg caggatctcc | 1020 |
| agagctcgcg | ccgaggcaga | aaccggtgag | gccccgcacc | tggtgcatgt ggacgcggcc | 1080 |
| cgcgcgctgt | ggcccctgcg | gcgcttctgg | aggagcacag | gcttctgccc ccgctgcca | 1140 |
| cacagccagg | ctgaccagta | cgtcctcagc | tgggaccagc | agctcaacct cgcctatgtg | 1200 |
| ggcgccgtcc | ctcaccgcgg | catcaagcag | gtccggaccc | actggctgct ggagcttgtc | 1260 |
| accaccaggg | ggtccactgg | acggggcctg | agctacaact | tcacccacct ggacgggtac | 1320 |
| ttggaccttc | tcaggagaa | ccagctcctc | ccagggtttg | agctgatggg cagcgcctcg | 1380 |
| ggccacttca | ctgactttga | ggacaagcag | caggtgtttg | agtggaagga cttggtctcc | 1440 |
| agcctggcca | ggagatacat | cggtaggtac | ggactggcgc | atgtttccaa gtggaacttc | 1500 |
| gagacgtgga | atgagccaga | ccaccacgac | tttgacaacg | tctccatgac catgcaaggc | 1560 |
| ttcctgaact | actacgatgc | ctgctcggag | ggtctgcgcg | ccgccagccc cgccctgcgg | 1620 |
| ctgggaggcc | ccggcgactc | cttccacacc | ccaccgcgat | ccccgctgag ctggggcctc | 1680 |
| ctgcgccact | gccacgacgg | taccaacttc | ttcactgggg | aggcgggcgt gcggctggac | 1740 |
| tacatctccc | tccacaggaa | gggtgcgcgc | agctccatct | ccatcctgga gcaggagaag | 1800 |
| gtcgtcgcgc | agcagatccg | gcagctcttc | cccaagttcg | cggacacccc catttacaac | 1860 |
| gacgaggcgg | accgctggt | gggctggtcc | ctgccacagc | cgtggagggc ggacgtgacc | 1920 |
| tacgcggcca | tggtggtgaa | ggtcatcgcg | cagcatcaga | acctgctact ggccaacacc | 1980 |

-continued

```
acctccgcct tcccctacgc gctcctgagc aacgacaatg ccttcctgag ctaccacccg    2040
caccccttcg cgcagcgcac gctcaccgcg cgcttccagg tcaacaacac ccgcccgccg    2100
cacgtgcagc tgttgcgcaa gccggtgctc acggccatgg ggctgctggc gctgctggat    2160
gaggagcagc tctgggccga agtgtcgcag gccgggaccg tcctggacag caaccacacg    2220
gtgggcgtcc tggccagcgc ccaccgcccc cagggcccgg ccgacgcctg gcgcgccgcg    2280
gtgctgatct acgcgagcga cgacaccgcc cccaccccca accgcagcgt cgcggtgacc    2340
ctgcggctgc gcggggtgcc ccccggcccg ggcctggtct acgtcacgcg ctacctggac    2400
aacgggctct gcagccccga cggcgagtgg cggcgcctgg gccggcccgt cttccccacg    2460
gcagagcagt tccggcgcat gcgcgcggct gaggacccgg tggccgcggc gccccgcccc    2520
ttacccgccg gcggccgcct gaccctgcgc cccgcgctgc ggctgccgtc gcttttgctg    2580
gtgcacgtgt gtgcgcgccc cgagaagccg cccgggcagg tcacgcggct ccgcgccctg    2640
cccctgaccc aagggcagct ggttctggtc tggtcggatg aacacgtggg ctccaagtgc    2700
ctgtggacat acgagatcca gttctctcag gacggtaagg cgtacacccc ggtcagcagg    2760
aagccatcga ccttcaacct ctttgtgttc agcccagaca caggtgctgt ctctggctcc    2820
taccgagttc gagccctgga ctactgggcc cgaccaggcc ccttctcgga ccctgtgccg    2880
tacctggagg tccctgtgcc aagagggccc ccatccccgg gcaatccatg actcgag      2937
```

<210> SEQ ID NO 9
<211> LENGTH: 972
<212> TYPE: PRT
<213> ORGANISM: Artificial sequence
<220> FEATURE:
<223> OTHER INFORMATION: RAP-IDU fusion sequence

<400> SEQUENCE: 9

```
Met Arg Gly Pro Ser Gly Ala Leu Trp Leu Leu Leu Ala Leu Arg Thr
1               5                   10                  15

Val Leu Gly Ser Tyr Ser Arg Glu Lys Asn Gln Pro Lys Pro Ser Pro
            20                  25                  30

Lys Arg Glu Ser Gly Glu Glu Phe Arg Met Glu Lys Leu Asn Gln Leu
        35                  40                  45

Trp Glu Lys Ala Gln Arg Leu His Leu Pro Pro Val Arg Leu Ala Glu
    50                  55                  60

Leu His Ala Asp Leu Lys Ile Gln Glu Arg Asp Glu Leu Ala Trp Lys
65                  70                  75                  80

Lys Leu Lys Leu Asp Gly Leu Asp Glu Asp Gly Lys Glu Ala Arg
                85                  90                  95

Leu Ile Arg Asn Leu Asn Val Ile Leu Ala Lys Tyr Gly Leu Asp Gly
                100                 105                 110

Lys Lys Asp Ala Arg Gln Val Thr Ser Asn Ser Leu Ser Gly Thr Gln
            115                 120                 125

Glu Asp Gly Leu Asp Asp Pro Arg Leu Glu Lys Leu Trp His Lys Ala
        130                 135                 140

Lys Thr Ser Gly Lys Phe Ser Gly Glu Glu Leu Asp Lys Leu Trp Arg
145                 150                 155                 160

Glu Phe Leu His His Lys Glu Lys Val His Glu Tyr Asn Val Leu Leu
                165                 170                 175

Glu Thr Leu Ser Arg Thr Glu Glu Ile His Glu Asn Val Ile Ser Pro
            180                 185                 190

Ser Asp Leu Ser Asp Ile Lys Gly Ser Val Leu His Ser Arg His Thr
```

```
            195                 200                 205
Glu Leu Lys Glu Lys Leu Arg Ser Ile Asn Gln Gly Leu Asp Arg Leu
    210                 215                 220

Arg Arg Val Ser His Gln Gly Tyr Ser Thr Glu Ala Glu Phe Glu Glu
225                 230                 235                 240

Pro Arg Val Ile Asp Leu Trp Asp Leu Ala Gln Ser Ala Asn Leu Thr
                245                 250                 255

Asp Lys Glu Leu Glu Ala Phe Arg Glu Leu Lys His Phe Glu Ala
            260                 265                 270

Lys Ile Glu Lys His Asn His Tyr Gln Lys Gln Leu Glu Ile Ala His
        275                 280                 285

Glu Lys Leu Arg His Ala Glu Ser Val Gly Asp Gly Glu Arg Val Ser
    290                 295                 300

Arg Ser Arg Glu Lys His Ala Leu Leu Glu Gly Arg Thr Lys Glu Leu
305                 310                 315                 320

Gly Tyr Thr Val Lys Lys His Leu Gln Asp Leu Ser Gly Arg Ile Ser
                325                 330                 335

Arg Ala Arg Ala Glu Ala Glu Thr Gly Glu Ala Pro His Leu Val His
            340                 345                 350

Val Asp Ala Ala Arg Ala Leu Trp Pro Leu Arg Arg Phe Trp Arg Ser
        355                 360                 365

Thr Gly Phe Cys Pro Pro Leu Pro His Ser Gln Ala Asp Gln Tyr Val
    370                 375                 380

Leu Ser Trp Asp Gln Gln Leu Asn Leu Ala Tyr Val Gly Ala Val Pro
385                 390                 395                 400

His Arg Gly Ile Lys Gln Val Arg Thr His Trp Leu Leu Glu Leu Val
                405                 410                 415

Thr Thr Arg Gly Ser Thr Gly Arg Gly Leu Ser Tyr Asn Phe Thr His
            420                 425                 430

Leu Asp Gly Tyr Leu Asp Leu Leu Arg Glu Asn Gln Leu Leu Pro Gly
        435                 440                 445

Phe Glu Leu Met Gly Ser Ala Ser Gly His Phe Thr Asp Phe Glu Asp
    450                 455                 460

Lys Gln Gln Val Phe Glu Trp Lys Asp Leu Val Ser Ser Leu Ala Arg
465                 470                 475                 480

Arg Tyr Ile Gly Arg Tyr Gly Leu Ala His Val Ser Lys Trp Asn Phe
                485                 490                 495

Glu Thr Trp Asn Glu Pro Asp His His Asp Phe Asp Asn Val Ser Met
            500                 505                 510

Thr Met Gln Gly Phe Leu Asn Tyr Tyr Asp Ala Cys Ser Glu Gly Leu
        515                 520                 525

Arg Ala Ala Ser Pro Ala Leu Arg Leu Gly Gly Pro Gly Asp Ser Phe
    530                 535                 540

His Thr Pro Pro Arg Ser Pro Leu Ser Trp Gly Leu Leu Arg His Cys
545                 550                 555                 560

His Asp Gly Thr Asn Phe Phe Thr Gly Glu Ala Gly Val Arg Leu Asp
                565                 570                 575

Tyr Ile Ser Leu His Arg Lys Gly Ala Arg Ser Ser Ile Ser Ile Leu
            580                 585                 590

Glu Gln Glu Lys Val Val Ala Gln Gln Ile Arg Gln Leu Phe Pro Lys
        595                 600                 605

Phe Ala Asp Thr Pro Ile Tyr Asn Asp Glu Ala Asp Pro Leu Val Gly
    610                 615                 620
```

Trp Ser Leu Pro Gln Pro Trp Arg Ala Asp Val Thr Tyr Ala Ala Met
625                 630                 635                 640

Val Val Lys Val Ile Ala Gln His Gln Asn Leu Leu Ala Asn Thr
            645                 650                 655

Thr Ser Ala Phe Pro Tyr Ala Leu Leu Ser Asn Asp Asn Ala Phe Leu
                660                 665                 670

Ser Tyr His Pro His Pro Phe Ala Gln Arg Thr Leu Thr Ala Arg Phe
            675                 680                 685

Gln Val Asn Asn Thr Arg Pro Pro His Val Gln Leu Leu Arg Lys Pro
690                 695                 700

Val Leu Thr Ala Met Gly Leu Leu Ala Leu Leu Asp Glu Glu Gln Leu
705                 710                 715                 720

Trp Ala Glu Val Ser Gln Ala Gly Thr Val Leu Asp Ser Asn His Thr
                725                 730                 735

Val Gly Val Leu Ala Ser Ala His Arg Pro Gln Gly Pro Ala Asp Ala
                740                 745                 750

Trp Arg Ala Ala Val Leu Ile Tyr Ala Ser Asp Asp Thr Arg Ala His
                755                 760                 765

Pro Asn Arg Ser Val Ala Val Thr Leu Arg Leu Arg Gly Val Pro Pro
770                 775                 780

Gly Pro Gly Leu Val Tyr Val Thr Arg Tyr Leu Asp Asn Gly Leu Cys
785                 790                 795                 800

Ser Pro Asp Gly Glu Trp Arg Arg Leu Gly Arg Pro Val Phe Pro Thr
                805                 810                 815

Ala Glu Gln Phe Arg Arg Met Arg Ala Ala Glu Asp Pro Val Ala Ala
                820                 825                 830

Ala Pro Arg Pro Leu Pro Ala Gly Gly Arg Leu Thr Leu Arg Pro Ala
                835                 840                 845

Leu Arg Leu Pro Ser Leu Leu Leu Val His Val Cys Ala Arg Pro Glu
850                 855                 860

Lys Pro Pro Gly Gln Val Thr Arg Leu Arg Ala Leu Pro Leu Thr Gln
865                 870                 875                 880

Gly Gln Leu Val Leu Val Trp Ser Asp Glu His Val Gly Ser Lys Cys
                885                 890                 895

Leu Trp Thr Tyr Glu Ile Gln Phe Ser Gln Asp Gly Lys Ala Tyr Thr
                900                 905                 910

Pro Val Ser Arg Lys Pro Ser Thr Phe Asn Leu Phe Val Phe Ser Pro
                915                 920                 925

Asp Thr Gly Ala Val Ser Gly Ser Tyr Arg Val Arg Ala Leu Asp Tyr
930                 935                 940

Trp Ala Arg Pro Gly Pro Phe Ser Asp Pro Val Pro Tyr Leu Glu Val
945                 950                 955                 960

Pro Val Pro Arg Gly Pro Pro Ser Pro Gly Asn Pro
                965                 970

<210> SEQ ID NO 10
<211> LENGTH: 1398
<212> TYPE: DNA
<213> ORGANISM: Artificial sequence
<220> FEATURE:
<223> OTHER INFORMATION: RAP-GDNF fusion sequence

<400> SEQUENCE: 10 atgggggtt cttactcgcg ggagaagaac cagcccaagc cgtccccgaa acgcgagtcc    60

```
ggagaggagt tccgcatgga aagttgaac cagctgtggg agaaggccca gcgactgcat      120
cttcctcccg tgaggctggc cgagctccac gctgatctga agatacagga gagggacgaa      180
ctcgcctgga agaaactaaa gcttgacggc ttggacgaag atggggagaa ggaagcgaga      240
ctcatacgca acctcaatgt catcttggcc aagtatggtc tggacggaaa gaaggacgct      300
cggcaggtga ccagcaactc cctcagtggc acccaggaag acgggctgga tgacccagg       360 ctggaaaagc tgtggcacaa ggcgaagacc tctgggaaat tctccggcga agaactggac      420
aagctctggc gggagttcct gcatcacaaa gagaaagttc acgagtacaa cgtcctgctg      480
gagaccctga gcaggaccga agaaatccac gagaacgtca ttagcccctc ggacctgagc      540
gacatcaagg gcagcgtcct gcacagcagg cacacggagc tgaaggagaa gctgcgcagc      600
atcaaccagg gcctggaccg cctgcgcagg gtcagccacc agggctacag cactgaggct      660
gagttcgagg agcccagggt gattgacctg tgggacctgg cgcagtccgc caacctcacg      720
gacaaggagc tggaggcgtt ccgggaggag ctcaagcact tcgaagccaa aatcgagaag      780
cacaaccact accagaagca gctggagatt gcgcacgaga agctgaggca cgcagagagc      840
gtgggcgacg cgagcgtgt gagccgcagc cgcgagaagc acgccctgct ggaggggcgg      900
accaaggagc tgggctacac ggtgaagaag catctgcagg acctgtccgg caggatctcc      960
agagctcggg ccgaggcaga aaccggttca ccagataaac aaatggcagt gcttcctaga     1020
agagagcgga atcggcaggc tgcagctgcc aacccagaga attccagagg aaaaggtcgg     1080
agaggccaga ggggcaaaaa ccgggggttgt gtcttaactg caatacattt aaatgtcact     1140
gacttgggtc tgggctatga aaccaaggag gaactgattt taggtactg cagcggctct      1200 tgcgatgcag ctgagacaac gtacgacaaa atattgaaaa acttatccag aaatagaagg     1260
ctggtgagtg acaaagtagg gcaggcatgt tgcagaccca tcgcctttga tgatgacctg     1320
tcgtttttag atgataacct ggtttaccat attctaagaa agcattccgc taaaaggtgt     1380
ggatgtatct gatctaga                                                  1398
```

<210> SEQ ID NO 11
<211> LENGTH: 463
<212> TYPE: PRT
<213> ORGANISM: Artificial sequence
<220> FEATURE:
<223> OTHER INFORMATION: RAP-GDNF fusion sequence

<400> SEQUENCE: 11

Met Gly Gly Ser Tyr Ser Arg Glu Lys Asn Gln Pro Lys Pro Ser Pro
1               5                   10                  15

Lys Arg Glu Ser Gly Glu Glu Phe Arg Met Glu Lys Leu Asn Gln Leu
                20                  25                  30

Trp Glu Lys Ala Gln Arg Leu His Leu Pro Pro Val Arg Leu Ala Glu
            35                  40                  45

Leu His Ala Asp Leu Lys Ile Gln Glu Arg Asp Glu Leu Ala Trp Lys
        50                  55                  60

Lys Leu Lys Leu Asp Gly Leu Asp Glu Asp Gly Glu Lys Glu Ala Arg
65                  70                  75                  80

Leu Ile Arg Asn Leu Asn Val Ile Leu Ala Lys Tyr Gly Leu Asp Gly
                85                  90                  95

Lys Lys Asp Ala Arg Gln Val Thr Ser Asn Ser Leu Ser Gly Thr Gln
            100                 105                 110

Glu Asp Gly Leu Asp Asp Pro Arg Leu Glu Lys Leu Trp His Lys Ala
        115                 120                 125

```
Lys Thr Ser Gly Lys Phe Ser Gly Glu Glu Leu Asp Lys Leu Trp Arg
    130                 135                 140

Glu Phe Leu His His Lys Glu Lys Val His Glu Tyr Asn Val Leu Leu
145                 150                 155                 160

Glu Thr Leu Ser Arg Thr Glu Ile His Glu Asn Val Ile Ser Pro
                165                 170                 175

Ser Asp Leu Ser Asp Ile Lys Gly Ser Val Leu His Ser Arg His Thr
            180                 185                 190

Glu Leu Lys Glu Lys Leu Arg Ser Ile Asn Gln Gly Leu Asp Arg Leu
        195                 200                 205

Arg Arg Val Ser His Gln Gly Tyr Ser Thr Glu Ala Glu Phe Glu Glu
210                 215                 220

Pro Arg Val Ile Asp Leu Trp Asp Leu Ala Gln Ser Ala Asn Leu Thr
225                 230                 235                 240

Asp Lys Glu Leu Glu Ala Phe Arg Glu Glu Leu Lys His Phe Glu Ala
                245                 250                 255

Lys Ile Glu Lys His Asn His Tyr Gln Lys Gln Leu Glu Ile Ala His
            260                 265                 270

Glu Lys Leu Arg His Ala Glu Ser Val Gly Asp Gly Glu Arg Val Ser
        275                 280                 285

Arg Ser Arg Glu Lys His Ala Leu Leu Glu Gly Arg Thr Lys Glu Leu
290                 295                 300

Gly Tyr Thr Val Lys Lys His Leu Gln Asp Leu Ser Gly Arg Ile Ser
305                 310                 315                 320

Arg Ala Arg Ala Glu Ala Glu Thr Gly Ser Pro Asp Lys Gln Met Ala
                325                 330                 335

Val Leu Pro Arg Arg Glu Arg Asn Arg Gln Ala Ala Ala Asn Pro
            340                 345                 350

Glu Asn Ser Arg Gly Lys Gly Arg Arg Gly Gln Arg Gly Lys Asn Arg
        355                 360                 365

Gly Cys Val Leu Thr Ala Ile His Leu Asn Val Thr Asp Leu Gly Leu
370                 375                 380

Gly Tyr Glu Thr Lys Glu Glu Leu Ile Phe Arg Tyr Cys Ser Gly Ser
385                 390                 395                 400

Cys Asp Ala Ala Glu Thr Thr Tyr Asp Lys Ile Leu Lys Asn Leu Ser
                405                 410                 415

Arg Asn Arg Arg Leu Val Ser Asp Lys Val Gly Gln Ala Cys Cys Arg
            420                 425                 430

Pro Ile Ala Phe Asp Asp Leu Ser Phe Leu Asp Asp Asn Leu Val
        435                 440                 445

Tyr His Ile Leu Arg Lys His Ser Ala Lys Arg Cys Gly Cys Ile
    450                 455                 460

<210> SEQ ID NO 12
<211> LENGTH: 49
<212> TYPE: DNA
<213> ORGANISM: Artificial sequence
<220> FEATURE:
<223> OTHER INFORMATION: Synthetic primer

<400> SEQUENCE: 12
gcgataggat cctactcgcg ggagaagaac cagcccaagc cgtccccga                49

<210> SEQ ID NO 13
<211> LENGTH: 57
```

<212> TYPE: DNA
<213> ORGANISM: Artificial sequence
<220> FEATURE:
<223> OTHER INFORMATION: Synthetic primer

<400> SEQUENCE: 13
gcgataaacc ggtttctgcc tcggcgcgag ctctggagat cctgccggac aggtcct    57

<210> SEQ ID NO 14
<211> LENGTH: 39
<212> TYPE: DNA
<213> ORGANISM: Artificial sequence
<220> FEATURE:
<223> OTHER INFORMATION: Synthetic primer

<400> SEQUENCE: 14
gcgataaccg gtgcacaccc cggccgtccc agagcagtg    39

<210> SEQ ID NO 15
<211> LENGTH: 37
<212> TYPE: DNA
<213> ORGANISM: Artificial sequence
<220> FEATURE:
<223> OTHER INFORMATION: Synthetic primer

<400> SEQUENCE: 15
gcgatactcg agtcaacacc agctgacgag aaactgc    37

<210> SEQ ID NO 16
<211> LENGTH: 46
<212> TYPE: DNA
<213> ORGANISM: Artificial sequence
<220> FEATURE:
<223> OTHER INFORMATION: Synthetic primer

<400> SEQUENCE: 16
gcgataaccg gtgaggcccc ccgcacctgg tgcatgtgga cgcggc    46

<210> SEQ ID NO 17
<211> LENGTH: 45
<212> TYPE: DNA
<213> ORGANISM: Artificial sequence
<220> FEATURE:
<223> OTHER INFORMATION: Synthetic primer

<400> SEQUENCE: 17
gcgatactcg agtcatggat tgcccgggga tggggggccct cttgg    45

<210> SEQ ID NO 18
<211> LENGTH: 33
<212> TYPE: DNA
<213> ORGANISM: Artificial sequence
<220> FEATURE:
<223> OTHER INFORMATION: Synthetic primer

<400> SEQUENCE: 18
acagtgaccg gttcaccaga taaacaaatg gca    33

<210> SEQ ID NO 19
<211> LENGTH: 38
<212> TYPE: DNA
<213> ORGANISM: Artificial sequence
<220> FEATURE:
<223> OTHER INFORMATION: Synthetic primer

<400> SEQUENCE: 19

-continued acagtgctcg agtctagatc agatacatcc acaccttt    38

<210> SEQ ID NO 20
<211> LENGTH: 51
<212> TYPE: DNA
<213> ORGANISM: Artificial sequence
<220> FEATURE:
<223> OTHER INFORMATION: Synthetic primer

<400> SEQUENCE: 20
acagtggcca tgggggttc ttactcgcgg gagaagaacc agcccaagcc g    51

<210> SEQ ID NO 21
<211> LENGTH: 357
<212> TYPE: PRT
<213> ORGANISM: Homo sapiens

<400> SEQUENCE: 21

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
            20                  25                  30

Gly Lys Tyr Ser Arg Glu Lys Asn Gln Pro Lys Pro Ser Pro Lys Arg
        35                  40                  45

Glu Ser Gly Glu Glu Phe Arg Met Glu Lys Leu Asn Gln Leu Trp Glu
    50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
    130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
        195                 200                 205

Leu Ser Asp Ile Lys Gly Ser Val Leu His Ser Arg His Thr Glu Leu
    210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
                245                 250                 255

Val Ile Asp Leu Trp Asp Leu Ala Gln Ser Ala Asn Leu Thr Asp Lys
            260                 265                 270

Glu Leu Glu Ala Phe Arg Glu Glu Leu Lys His Phe Glu Ala Lys Ile
        275                 280                 285

Glu Lys His Asn His Tyr Gln Lys Gln Leu Glu Ile Ala His Glu Lys
    290                 295                 300

```
Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
            325                 330                 335

Thr Val Lys Lys His Leu Gln Asp Leu Ser Gly Arg Ile Ser Arg Ala
            340                 345                 350

Arg His Asn Glu Leu
        355

<210> SEQ ID NO 22
<211> LENGTH: 378
<212> TYPE: PRT
<213> ORGANISM: Mus musculus

<400> SEQUENCE: 22

Met Gly Gly Pro Thr Arg Pro Ser Pro Val Ser Leu Leu Ala Leu Gln
1               5                   10                  15

Arg Lys Met Ala Pro Arg Arg Glu Arg Val Ser Thr Leu Pro Arg Leu
            20                  25                  30

Gln Leu Leu Val Leu Leu Leu Leu Pro Leu Met Leu Val Pro Gln Pro
        35                  40                  45

Ile Ala Gly His Gly Gly Lys Tyr Ser Arg Glu Lys Asn Glu Pro Glu
    50                  55                  60

Met Ala Ala Lys Arg Glu Ser Gly Glu Glu Phe Arg Met Glu Lys Leu
65                  70                  75                  80

Asn Gln Leu Trp Glu Lys Ala Lys Arg Leu His Leu Ser Pro Val Arg
                85                  90                  95

Leu Ala Glu Leu His Ser Asp Leu Lys Ile Gln Glu Arg Asp Glu Leu
            100                 105                 110

Asn Trp Lys Lys Leu Lys Val Glu Gly Leu Asp Lys Asp Gly Glu Lys
        115                 120                 125

Glu Ala Lys Leu Ile His Asn Leu Asn Val Ile Leu Ala Arg Tyr Gly
    130                 135                 140

Leu Asp Gly Arg Lys Asp Ala Gln Met Val His Ser Asn Ala Leu Asn
145                 150                 155                 160

Glu Asp Thr Gln Asp Glu Leu Gly Asp Pro Arg Leu Glu Lys Leu Trp
                165                 170                 175

His Lys Ala Lys Thr Ser Gly Lys Phe Ser Ser Glu Glu Leu Asp Lys
            180                 185                 190

Leu Trp Arg Glu Phe Leu His Tyr Lys Glu Lys Ile Gln Glu Tyr Asn
        195                 200                 205

Val Leu Leu Asp Thr Leu Ser Arg Ala Glu Glu Gly Tyr Glu Asn Leu
    210                 215                 220

Leu Ser Pro Ser Asp Met Ala His Ile Lys Ser Asp Thr Leu Ile Ser
225                 230                 235                 240

Lys His Ser Glu Leu Lys Asp Arg Leu Arg Ser Ile Asn Gln Gly Leu
                245                 250                 255

Asp Arg Leu Arg Lys Val Ser His Gln Gly Tyr Gly Ser Thr Thr Glu
            260                 265                 270

Phe Glu Glu Pro Arg Val Ile Asp Leu Trp Asp Leu Ala Gln Ser Ala
        275                 280                 285

Asn Phe Thr Glu Lys Glu Leu Glu Ser Phe Arg Glu Glu Leu Lys His
    290                 295                 300

Phe Glu Ala Lys Ile Glu Lys His Asn His Tyr Gln Lys Gln Leu Glu
305                 310                 315                 320
```

```
Ile Ser His Gln Lys Leu Lys His Val Glu Ser Ile Gly Asp Pro Glu
            325                 330                 335

His Ile Ser Arg Asn Lys Glu Lys Tyr Val Leu Leu Glu Glu Lys Thr
        340                 345                 350

Lys Glu Leu Gly Tyr Lys Val Lys Lys His Leu Gln Asp Leu Ser Ser
        355                 360                 365

Arg Val Ser Arg Ala Arg His Asn Glu Leu
        370                 375

<210> SEQ ID NO 23
<211> LENGTH: 357
<212> TYPE: PRT
<213> ORGANISM: Rat

<400> SEQUENCE: 23

Leu Arg Asp Arg Val Ser Thr Leu Pro Arg Leu Gln Leu Leu Val Leu
1               5                   10                  15

Leu Leu Leu Pro Leu Leu Val Pro Gln Pro Ile Ala Gly His Gly
            20                  25                  30

Gly Lys Tyr Ser Arg Glu Lys Asn Glu Pro Glu Met Ala Ala Lys Arg
        35                  40                  45

Glu Ser Gly Glu Glu Phe Arg Met Glu Lys Leu Asn Gln Leu Trp Glu
50                  55                  60

Lys Ala Lys Arg Leu His Leu Ser Pro Val Arg Leu Ala Glu Leu His
65                  70                  75                  80

Ser Asp Leu Lys Ile Gln Glu Arg Asp Glu Leu Asn Trp Lys Lys Leu
                85                  90                  95

Lys Val Glu Gly Leu Asp Gly Asp Gly Glu Lys Glu Ala Lys Leu Val
            100                 105                 110

His Asn Leu Asn Val Ile Leu Ala Arg Tyr Gly Leu Asp Gly Arg Lys
        115                 120                 125

Asp Thr Gln Thr Val His Ser Asn Ala Leu Asn Glu Asp Thr Gln Asp
        130                 135                 140

Glu Leu Gly Asp Pro Arg Leu Glu Lys Leu Trp His Lys Ala Lys Thr
145                 150                 155                 160

Ser Gly Lys Phe Ser Ser Glu Glu Leu Asp Lys Leu Trp Arg Glu Phe
                165                 170                 175

Leu His Tyr Lys Glu Lys Ile His Glu Tyr Asn Val Leu Leu Asp Thr
            180                 185                 190

Leu Ser Arg Ala Glu Glu Gly Tyr Glu Asn Leu Leu Ser Pro Ser Asp
        195                 200                 205

Met Thr His Ile Lys Ser Asp Thr Leu Ala Ser Lys His Ser Glu Leu
        210                 215                 220

Lys Asp Arg Leu Arg Ser Ile Asn Gln Gly Leu Asp Arg Leu Arg Lys
225                 230                 235                 240

Val Ser His Gln Gly Tyr Gly Pro Ala Thr Glu Phe Glu Glu Pro Arg
                245                 250                 255

Val Ile Asp Leu Trp Asp Leu Ala Gln Ser Ala Asn Phe Thr Glu Lys
            260                 265                 270

Glu Leu Glu Ser Phe Arg Glu Glu Leu Lys His Phe Glu Ala Lys Ile
        275                 280                 285

Glu Lys His Asn His Tyr Gln Lys Gln Leu Glu Ile Ser His Gln Lys
        290                 295                 300

Leu Lys His Val Glu Ser Ile Gly Asp Pro Glu His Ile Ser Arg Asn
```

```
305             310             315             320
Lys Glu Lys Tyr Val Leu Leu Glu Glu Lys Thr Lys Glu Leu Gly Tyr
                325                 330                 335

Lys Val Lys Lys His Leu Gln Asp Leu Ser Ser Arg Val Ser Arg Ala
            340                 345                 350

Arg His Asn Glu Leu
        355

<210> SEQ ID NO 24
<211> LENGTH: 348
<212> TYPE: PRT
<213> ORGANISM: Chicken

<400> SEQUENCE: 24

Met Gly Ala Thr Arg Thr Leu Val Ala Val Met Ala Ala Phe Leu Ala
1               5                   10                  15

Val Ser Thr Arg Ala Ser Lys Tyr Thr Arg Glu Ala Asn Glu Gly Leu
            20                  25                  30

Ala Asp Ala Lys Arg Arg Glu Ala Gly Glu Phe Arg Val Val Arg Leu
        35                  40                  45

Asn Gln Val Trp Glu Lys Ala Gln Arg Leu Gln Leu Ser Ala Val Lys
    50                  55                  60

Leu Ala Glu Leu His Ser Asp Leu Lys Ile Gln Glu Lys Asp Glu Leu
65                  70                  75                  80

Ser Trp Lys Lys Leu Lys Ala Glu Gly Leu Gly Glu Asp Gly Glu Lys
                85                  90                  95

Glu Ala Lys Leu Arg Arg Asn Ile Asn Val Ile Met Thr Lys Tyr Gly
            100                 105                 110

Met Asn Gly Lys Lys Asp Ser His Leu Thr Asp Thr Asn Tyr Ile Lys
        115                 120                 125

Asp Gly Thr Glu Ser Asp Thr Leu Asp Asp Pro Arg Leu Glu Lys Leu
    130                 135                 140

Trp Ser Lys Ala Lys Thr Ser Gly Lys Phe Ser Asp Glu Glu Leu Asp
145                 150                 155                 160

Lys Leu Trp Arg Glu Phe Lys His His Lys Glu Lys Ile Arg Glu Tyr
                165                 170                 175

Asn Ile Leu Leu Glu Thr Val Ser Arg Thr Glu Asp Ile His Lys Lys
            180                 185                 190

Val Ile Asn Pro Ser Glu Glu Asn Pro Val Lys Glu Glu Val Leu His
        195                 200                 205

Asn Lys His Arg Glu Leu Lys Glu Lys Leu Arg Ser Ile Asn Gln Gly
    210                 215                 220

Phe Glu Arg Leu Arg Lys Val Ser His Gln Gly Tyr Asp Ala Thr Ser
225                 230                 235                 240

Glu Phe Glu Glu Pro Arg Val Ile Asp Leu Trp Asp Met Ala Lys Ser
                245                 250                 255

Ala Asn Phe Thr Glu Lys Glu Leu Glu Ser Phe Arg Glu Glu Leu Lys
            260                 265                 270

His Phe Glu Ala Lys Ile Glu Lys His His Tyr Gln Lys Gln Leu
        275                 280                 285

Glu Ile Ser His Glu Lys Leu Lys His Ile Glu Gly Thr Gly Asp Lys
    290                 295                 300

Glu His Leu Asn Arg Asn Arg Glu Lys Tyr Ala Met Leu Glu Glu Lys
305                 310                 315                 320
```

```
Thr Lys Glu Leu Gly Tyr Lys Val Lys His Leu Gln Asp Leu Ser
                325                 330                 335

Ser Arg Ile Ser Gln Gly Leu Gln His Asn Glu Leu
            340                 345

<210> SEQ ID NO 25
<211> LENGTH: 331
<212> TYPE: PRT
<213> ORGANISM: Zebrafish

<400> SEQUENCE: 25

Met Ala Gly Lys Tyr Ser Lys Glu Met Asn Glu Lys Asn Ala Ser Asp
1               5                   10                  15

Lys Ser Asn Asn Gln Val Glu Phe Arg Ile Ala Lys Leu Asn Gln Val
            20                  25                  30

Trp Glu Lys Ala Ile Arg Met Gln Leu Ala Pro Val Arg Leu Ser Glu
        35                  40                  45

Leu His Ser Asp Leu Lys Ile Gln Glu Lys Asp Glu Leu Gln Trp Lys
    50                  55                  60

Lys Leu Lys Ala Glu Gly Met Asp Glu Asp Gly Glu Arg Glu Ala Lys
65                  70                  75                  80

Leu Arg Arg Asn Phe Asn Ile Ile Leu Ala Lys Tyr Gly Met Asp Gly
                85                  90                  95

Lys Lys Asp Thr Arg Thr Leu Asp Ser Asn Arg Leu Lys Asp His Glu
            100                 105                 110

Val Lys Ile Gly Asp Thr Phe Asp Asp Pro Lys Leu Asp Lys Leu Trp
        115                 120                 125

Asn Lys Ala Arg Thr Ser Gly Lys Phe Ser Asp Glu Glu Leu Gln Thr
130                 135                 140

Leu His Arg Glu Phe Gln His His Lys Asp Lys Ile His Glu Tyr Asn
145                 150                 155                 160

Ile Val Met Asp Thr Val Ser Arg Thr Glu Ile His Lys Asn Val
                165                 170                 175

Ile Ser Pro Leu Glu Gly Asp Val Lys Glu Asn Val Leu His Gln Lys
            180                 185                 190

His Thr Asp Leu Lys Gln Arg Met Arg Asp Leu Asn Gln Gly Phe Glu
        195                 200                 205

Arg Leu Arg Lys Ile Thr His Glu Gly Tyr Thr Asp Asp Ser Glu Phe
    210                 215                 220

Arg Glu Pro Arg Val Ile Glu Leu Trp Glu Met Ala Lys Arg Ser Asn
225                 230                 235                 240

Leu Ser Glu Asp Glu Leu Asp Ser Leu Lys Glu Glu Leu Arg His Phe
                245                 250                 255

Glu Thr Lys Val Glu Lys His Gln His Tyr Gln Glu Gln Leu Glu Leu
            260                 265                 270

Ser His Gln Lys Leu Lys His Val Glu Ala Leu Gly Asp Glu Asp His
        275                 280                 285

Ile Met Arg Asn Lys Glu Lys Tyr Asn Thr Leu Ala Glu Lys Ala Arg
    290                 295                 300

Glu Met Gly Tyr Lys Met Lys Lys His Leu Gln Asp Leu Thr Asn Lys
305                 310                 315                 320

Leu Ser Lys Asn Gly Leu Gln His Asn Glu Leu
                325                 330

<210> SEQ ID NO 26
```

<211> LENGTH: 379
<212> TYPE: PRT
<213> ORGANISM: Fruit fly

<400> SEQUENCE: 26

```
Met Val Arg Ser Ala Leu Val Val Ala Ala Ile Ala Leu Ser Val Leu
1               5                   10                  15

Ile Ala Leu Gln Gly Val Asp Ala Asp Lys Lys Gln Ser Lys Lys Tyr
            20                  25                  30

Ser Lys Glu Ala Asn Asp Pro His Phe Gln Gln Val Lys Gln Glu Lys
        35                  40                  45

Tyr Asp Pro Asp Phe Lys Ser Ile Gln Arg Pro Phe Arg Met Ala Lys
    50                  55                  60

Leu Asn Leu Val Trp Ala Lys Ala Gln Asn Arg Leu Thr Glu Pro Lys
65                  70                  75                  80

Leu Lys Ser Leu Tyr Met Glu Leu Lys Ile His Asp Lys Glu Ile
                85                  90                  95

Ala Trp Lys Gln Leu Asn Ser Gln His Lys Asp Lys Asp Gly Leu Lys
            100                 105                 110

Ala Asp Glu Leu Arg Arg Lys Leu Ile Gly Ile Met Ser Ser Tyr Asp
            115                 120                 125

Leu Leu Glu His Phe Asp Asp Thr Gln Asp Thr Glu Lys Leu Lys Pro
130                 135                 140

Tyr Lys Lys Phe His Asp Ala Glu Glu Arg His Arg Asn Lys Ser Leu
145                 150                 155                 160

Phe Lys Asp Lys Lys Leu Asn Arg Leu Trp Glu Lys Ala Glu Ile Ser
                165                 170                 175

Gly Phe Thr Ala Glu Glu Leu Lys Ser Leu Lys Gln Glu Phe Asp His
            180                 185                 190

His Gln Asp Lys Val Asp Val Tyr Tyr Ser Leu Leu Glu Asn Ile Gly
            195                 200                 205

Thr Val Asp Thr Asp Lys His Glu Asn Ala Ile Asn Thr Glu Asp Leu
            210                 215                 220

Asp Thr Tyr Asn Leu Ile Ser Asn Asp Val Asn Glu Asn Asp Ile Lys
225                 230                 235                 240

Thr His Ala Gln Asn Val Lys Ser Phe Glu Asn Asp Leu Asn Thr Leu
                245                 250                 255

Arg Gly His His Thr Gly Ile Lys Asp His Tyr Asp Arg Leu Glu Arg
            260                 265                 270

Leu Val Ser Ser Gly Pro His Ser Gln Asp Phe Ile Glu Pro Lys Val
            275                 280                 285

Gln Gly Leu Trp Arg Val Ala Gln Ala Ser Asn Phe Thr Val Lys Glu
            290                 295                 300

Leu Glu Ser Ile Lys Thr Glu Leu His His Phe Glu Ser Arg Leu Leu
305                 310                 315                 320

Lys Leu Arg His Leu His Ala Glu His Ala Leu Gln Lys Glu Lys Tyr
                325                 330                 335

Lys Gly Glu Lys Val Lys Asp Lys Ser Ser Arg Phe Glu Glu Met Glu
            340                 345                 350

Asp Gln Leu Lys Lys Gln Thr Arg Lys Val Glu Lys Leu Gln Glu Asn
            355                 360                 365

Ile Glu Lys Thr Ile Phe Lys His Thr Glu Leu
            370                 375
```

```
<210> SEQ ID NO 27
<211> LENGTH: 400
<212> TYPE: PRT
<213> ORGANISM: Mosquito

<400> SEQUENCE: 27

Glu Leu Cys Pro Ile Ala Arg Arg Lys Arg Gly Ile Lys His Thr Leu
1               5                   10                  15

Thr Met Pro Leu Phe Thr Arg Leu Cys Val Ile Val Phe Thr Val Leu
            20                  25                  30

Val Cys Asn His Val Val Gln Ser Glu Lys Ala His Ser Lys Tyr Ser
        35                  40                  45

Lys His Ala Asn Ala Leu Pro Asp Ser Glu Ile Tyr Glu Pro Asp Phe
    50                  55                  60

Arg Asn Ile Gln Arg Pro Phe Arg Met Ala Lys Leu Asn Leu Val Trp
65                  70                  75                  80

Thr Lys Ala Gln His Arg Leu Thr Glu Pro Lys Leu Lys Ser Leu Tyr
                85                  90                  95

Thr Glu Leu Lys Leu His Asp Lys Glu Glu Leu Thr Tyr Lys Gln Leu
            100                 105                 110

Lys Glu Lys Asp Lys Asp Gly Leu Lys Glu Ala Glu Leu Arg Asn Lys
        115                 120                 125

Leu Val Ser Ile Met Ser Thr Tyr Gly Leu Leu Glu His Phe Asp Asp
    130                 135                 140

Thr Gln Asp Pro Glu Lys Tyr Lys Leu Ala Lys Ser Ser Asp Gly Ala
145                 150                 155                 160

Pro Lys Lys Asp Thr Tyr Lys Asn Lys Ser Leu Phe Lys Asp Lys Lys
                165                 170                 175

Leu Asn Lys Leu Trp Asp Lys Ala Glu Ser Ala Gly Phe Thr Lys Glu
            180                 185                 190

Glu Leu Asp Ala Leu Arg Glu Glu Phe Asp His His Gln Ala Lys Ile
        195                 200                 205

Asp Val Tyr Tyr Ser Leu Leu Glu Arg Leu Gly Asp Asp Asp Asp Gly
    210                 215                 220

Gly Ala Ala Gly Gln Gly Ser Arg Arg Asp Asp Asp Ala Leu Leu Asn
225                 230                 235                 240

Ala Val Asn Asp Glu Glu His Asp Arg Tyr Asn Glu Val Asp Arg Ala
                245                 250                 255

Glu Glu Thr Asp Arg Ser Gln Pro Gly Ala Asn Lys Gln His Ala Tyr
            260                 265                 270

Leu His Lys Ser Asn Gln Leu Arg Glu Lys His Arg Glu Ile Arg Asp
        275                 280                 285

Asn Phe Asp Arg Leu Asp Arg Ile Ala Ser Lys Gly Pro Lys Ser Gln
    290                 295                 300

Asp Phe Val Glu Pro Lys Val Gln Gly Leu Trp Arg Val Ala Leu Ala
305                 310                 315                 320

Ser Asp Phe Ser Ala Asp Glu Leu Ala Ser Leu Lys Val Glu Leu Leu
                325                 330                 335

His Tyr Glu Ser Arg Leu Leu Lys Leu Arg His Met His Ala Glu His
            340                 345                 350

Ala Leu Ser Leu Glu Lys His Lys His Ser Asp Ala Lys Ala Asp Thr
        355                 360                 365

His Lys Leu Met Glu Asp Asn Ile Lys Lys Gln Thr Arg Lys Val Glu
    370                 375                 380
```

```
Lys Met Gln Glu Glu Val Arg Arg Ile Phe Lys His Ser Glu Leu
385                 390                 395                 400

<210> SEQ ID NO 28
<211> LENGTH: 331
<212> TYPE: PRT
<213> ORGANISM: Flatworm

<400> SEQUENCE: 28

Met Arg Asn His Phe Ser Phe Leu Leu Phe Leu Val Ile Gly Ser
1               5                   10                  15

Ala His Asn Lys Lys Thr Gln Tyr Arg Thr Glu Arg Ile Asn Phe Ile
        20                  25                  30

Tyr Glu Lys Ala Leu Gln His Val Thr Asp Arg Gln Asn Leu Ala Arg
            35                  40                  45

Leu Glu Lys Glu Leu Ser Gly Tyr Asp Ala Ile Tyr Leu Ala Ser Lys
    50                  55                  60

Ser Asn Arg Gln Gly Thr Gln Gly Thr Lys Glu Ile Asp Lys Ile Asp
65                  70                  75                  80

Asp Lys Leu Gly Lys Ile Leu Glu Lys Tyr Gly Leu Glu Lys Ala Val
                85                  90                  95

Leu Ala Phe Lys Glu Lys Tyr Lys His Lys Asn Leu Phe Gln Gln Thr
            100                 105                 110

Asp Asp Asn Glu Pro Leu Pro Ser Gly Lys Phe Thr Asp Gln Asn Leu
        115                 120                 125

Gln Lys Leu Trp Ser Gln Ala Gln Asn Gly Lys Phe Ser Gln Lys Glu
    130                 135                 140

Leu Asn Ala Leu His Gly Glu Leu Lys Glu Val Glu Gln Lys Met Arg
145                 150                 155                 160

Val Tyr Glu Asp Gln Leu Asp Asp Phe Lys Lys Val Pro His Glu Asn
                165                 170                 175

Ser Ile Gln His Asp Ile Glu Ser Ile Gly Asp Lys Thr Lys Lys Leu
            180                 185                 190

Lys Ala Ala Asn Arg Glu Leu Asn Asp His Leu Asp Glu Val His Arg
        195                 200                 205

Lys Val Thr Ser Glu Glu Phe Ser Pro Phe Asn Glu Pro Arg Val Lys
    210                 215                 220

Arg Leu Trp Lys Leu Ala Gln Glu Asn Glu Lys Leu Thr Pro His Glu
225                 230                 235                 240

Leu Ser Val Leu Lys Asp Glu Leu Ser His Phe Glu Ser Gln Leu Lys
                245                 250                 255

Lys Ile Glu Phe His Lys Val Phe Phe Phe Val Ala Asn Ser Cys Pro
            260                 265                 270

Lys Arg Gly Lys Asn Glu Glu Val Ser Arg Leu Gln Glu Asp Ala Glu
        275                 280                 285

Glu Arg Gly Lys Asp Lys Ser Gln Val Tyr Glu Asn Leu Glu Leu Ser
    290                 295                 300

Ile Lys His Glu Lys Leu Asn Arg Lys Ala Arg Lys Leu Glu Lys Tyr
305                 310                 315                 320

Ile Glu Glu Lys Ile Ile Ile His Arg Glu Leu
                325                 330

<210> SEQ ID NO 29
<211> LENGTH: 6
<212> TYPE: PRT
<213> ORGANISM: Artificial sequence
```

```
-continued

<220> FEATURE:
<223> OTHER INFORMATION: Synthetic peptide

<400> SEQUENCE: 29

Ala Glu Ala Glu Thr Gly
1               5
```

RECEPTOR ASSOCIATED PROTEIN (RAP) CONJUGATES

CROSS-REFERENCE TO RELATED APPLICATIONS

This application is a continuation-in-part of U.S. patent application Ser. No. 10/600,862, filed on Jun. 20, 2003. The contents of this prior U.S. application and all other U.S. patents cited herein are each hereby incorporated by reference in their entirety.

BACKGROUND

1. Field of the Invention

The present invention is generally directed to compositions for and methods for achieving the delivery of therapeutic and/or diagnostic/investigational agents.

2. Background of the Related Art

The brain is shielded against potentially harmful substances by the blood-brain barrier (BBB). The microvascular barrier between blood and brain is made up of a capillary endothelial layer surrounded by a basement membrane and tightly associated accessory cells (pericytes, astrocytes). The brain capillary endothelium is much less permeable to low-molecular weight solutes than other capillary endothelia due to an apical band of tight association between the membranes of adjoining cells, referred to as tight junctions. In addition to diminished passive diffusion, brain capillary endothelia also exhibit less fluid-phase pinocytosis than other endothelial cells. Brain capillaries possess few fenestrae and few endocytic vesicles, compared to the capillaries of other organs (see Pardridge, J. Neurovirol. 5: 556-569, 1999). There is little transit across the BBB of large, hydrophilic molecules aside from some specific proteins such as transferrin, lactoferrin and low-density lipoproteins, which are taken up by receptor-mediated endocytosis (see Pardridge, J. Neurovirol. 5: 556-569, 1999); Tsuji and Tamai, Adv. Drug Deliv. Rev. 36: 277-290 (1999); Kusuhara and Sugiyama, Drug Discov. Today 6:150-156 (2001); Dehouck et al. J. Cell. Biol. 138: 877-889 (1997); Fillebeen et al. J. Biol. Chem. 274: 7011-7017, 1999).

The blood-brain barrier (BBB) also impedes access of beneficial active agents (e.g., therapeutic drugs and diagnostic agents) to central nervous system (CNS) tissues, necessitating the use of carriers for their transit. Blood-brain barrier permeability is frequently a rate-limiting factor for the penetration of drugs or peptides into the CNS (see Pardridge, J. Neurovirol. 5: 556-569, 1999); Bickel et al., Adv. Drug Deliv. Rev. 46: 247-279, 2001). For example, management of the neurological manifestations of lysosomal storage diseases (LSDs) is significantly impeded by the inability of therapeutic enzymes to gain access to brain cell lysosomes. LSDs are characterized by the absence or reduced activity of specific enzymes within cellular lysosomes, resulting in the accumulation of undegraded "storage material" within the intracellular lysosome, swelling and malfunction of the lysosomes, and ultimately cellular and tissue damage. Intravenous enzyme replacement therapy (ERT) is beneficial for LSDs (e.g. MPS I, MPS II). However, the BBB blocks the free transfer of many agents from blood to brain, and LSDs that present with significant neurological sequelae (e.g. MPS III, MLD, and GM1) are not expected to be as responsive to intravenous ERT. For such diseases, a method of delivering the replacement enzyme across the BBB and into the lysosomes of the affected cells would be highly desirable.

Three ways of circumventing the BBB to enhance brain delivery of an administered active agent include direct intracranial injection, transient permeabilization of the BBB, and modification of the active agent to alter tissue distribution. Direct injection of an active agent into brain tissue bypasses the vasculature completely, but suffers primarily from the risk of complications (infection, tissue damage) incurred by intracranial injections and poor diffusion of the active agent from the site of administration. Permeabilization of the BBB entails non-specifically compromising the BBB concomitant with injection of intravenous active agent and is accomplished through loosening tight junctions by hyperosmotic shock (e.g. intravenous mannitol). High plasma osmolarity leads to dehydration of the capillary endothelium with partial collapse of tight junctions, little selectivity in the types of blood-borne substances that gain access to the brain under these conditions, and damage over the course of a life-long regimen of treatment.

The distribution of an active agent into the brain may also be increased by transcytosis, the active transport of certain proteins from the luminal space (blood-side) to the abluminal space (brain-side) of the BBB. Transcytosis pathways are distinct from other vesicular traffic within the capillary endothelial cell and transit can occur without alteration of the transported materials. Transcytosis is a cell-type specific process mediated by receptors on the BBB endothelial surface. Attachment of an active agent to a transcytosed protein (vector or carrier) is expected to increase distribution of the active substance to the brain. In transcytosis, the vector is presumed to have a dominant effect on the distribution of the joined pair. Vector proteins include antibodies directed at receptors on the brain capillary endothelium (Pardridge, J. Neurovirol. 5: 556-569, 1999) and ligands to such receptors (Fukuta et al., Pharm Res., 11(12):1681-8; 1994; Broadwell et al., Exp Neurol., 142(1):47-65 1996). Antibody vectors are transported through the capillary endothelium by a process of adsorptive endocytosis (non-specific, membrane-phase endocytosis) and are far less efficiently transported than actual receptor ligands, which cross the BBB by a saturable, energy-dependent mechanism (Broadwell et al., Exp Neurol., 142(1):47-65 1996).

The lipoprotein receptor-related protein (LRP) receptor family comprises a group of membrane-spanning, endocytic proteins with homology to the LDL receptor. Characterized as playing a key role in lipoprotein metabolism, LRP have subsequently been shown to bind a variety of ligands present in the blood. (Herz and Strickland, J Clin Invest., 108(6):779-84, 2001). LRP ligands include the lipoprotein-associated proteins ApoE, ApoJ and lipoprotein lipase; proteinases tPA, uPA, Factor 1x and MMP-9; proteinase inhibitors PAI-1, antithrombin III, alpha-2-macroglobulin and alpha-antitrypsin; the antibacterial protein lactoferrin; the chaperone receptor-associated protein (RAP), the hormone thyrotropin, the cofactor cobalamin and the lysosomal proteins saposin and sphingolipid activator protein. Four of these ligands, ApoJ (Zlokovic et al., Proc. Nat'l Acad. Sci., USA 93(9): 4229-34 1996; Zlokovic, Life Sci., 59(18):1483-97, 1996), thyrotropin (Marino et al., J. Biol. Chem., 275(10):7125-37 2000; Marino et al., J. Biol. Chem., 274(18):12898-904, 1999), lipoprotein lipase (Obunike et al. J. Biol. Chem., 276 (12):8934-41, 2001) and cobalamin (Ramanujam et al., Arch Biochem Biophys., 315(1):8-15, 1994) have been shown to be transcytosed across capillary endothelial cells in vitro and in vivo by LRP family members.

Taken together, the LRP receptor family comprises a pool of compositionally and functionally related receptors expressed at different levels in different tissues, including capillary endothelium, neurons and astrocytes. LRP family members are professional endocytic receptors that have also been shown to transcytose ligands across polarized epithelia.

A unique LRP ligand is the receptor-associated protein, RAP, a 39 kD chaperone localized to the endoplasmic reticulum and Golgi (Bu and Schwartz, Trends Cell. Biol. 8(7):272-6, 1998). RAP binds tightly to LRP in these compartments preventing premature association of the receptor with co-expressed ligands (Herz and Willnow, Atherosclerosis 118 Suppl:S37-41, 1995). RAP serves as an attractive targeting sequence for LRP due to its high affinity for all members of the LRP receptor family (~2 nM) and ability to out-compete all known LRP ligands. Since RAP is not secreted, endogenous levels in the blood are low. Endocytosis of RAP by LRP results in localization to the lysosome and complete degradation of the protein. Structure-function studies have been performed on RAP, providing some guidance on minimization of the sequence required to fulfill the targeting function (Melman, et al., J. Biol. Chem. 276(31): 29338-46, 2001). It is not known whether RAP is transcytosed, but Megalin-RAP complexes have been shown to remain intact as far as the late endosome (Czekay et al., Mol. Biol. Cell. 8(3):517-32, 1997). The integrity of the Megalin-RAP complex through the Compartment of Uncoupling Ligand from Receptor (CURL) and into this late endosomal compartment is in contrast to the observed instability of other LRP-ligand complexes in the early endosome. The LRP-RAP complex thus appears to have enhanced resistance to acid-dependent dissociation, a potential indicator of transcytotic competence. RAP could be engineered to be more specific for particular members of the LRP family. Such modifications would allow more selective targeting of RAP fusions to particular tissues, as dictated by the expression of different LRP family members on those tissues.

Furthermore, RAP may be a suitable substitute for the mannose 6-phosphate targeting signal on lysosomal enzymes. The LRP-RAP system shares many features with the mannose-6-phosphate receptor (MPR)-mannose 6-phosphate (M6P) system: Both receptor-ligand complexes, LRP-RAP and MPR-M6P, exhibit dissociation constants in the 1-2 nM range and are stable in the CURL. Both LRP and MPR are widely expressed on a variety of tissues and efficiently transport bound ligand to the lysosome. Both types of ligands are degraded upon reaching the lysosome. The advantage of RAP targeting over M6P targeting is that it depends on a protein sequence rather than a modified carbohydrate. Biosynthetic throughput and quality control are much higher for an amino acid sequence than for a modified oligosaccharide, allowing for better drug yield, potency and safety. The LRP-RAP system may also provide a method of efficiently targeting other tissues. For example, the high density of the Very Low Density Lipoprotein Receptor (VLDLR), a member of the LRP family), as well as LRP1 on muscle cells implies that RAP fusions could be taken up to a significant extent by muscle through LRP receptor-dependent endocytosis (Takahashi et al., Proc. Natl. Acad. Sci. U.S.A. 89(19):9252-6, 1992).

However, there remains a need for novel compounds, pharmaceutical compositions, and methods of administration of such compounds and compositions that can more effectively deliver active agents to the brain and other biological compartments. In particular, there is a need for such novel compounds, pharmaceutical compositions, and methods of administration which deliver active agents to the brain and tissues or organs that are set off from the blood compartment by capillary endothelial cells that are closely sealed by tight junctions. In particular, there is a need for such novel compounds, pharmaceutical compositions, and methods of administration, which efficiently target the delivery of an active agent to a wide variety of tissues. In particular, there is a need for such novel compounds, pharmaceutical compositions, and methods of administration, which target the delivery of an active agent to the lysosomal compartment of a cell within those tissues. This invention provides such compounds, pharmaceutical compositions and methods for their use.

SUMMARY OF THE INVENTION

The present invention relates to the discovery that megalin ligands can be used as carriers or vectors for the delivery of active agents via transcytosis. An exemplary such ligand is RAP, which serves to increase the transport of therapeutic and/or diagnostic/investigational agents across the blood brain barrier and/or deliver agents to lysosomes of cells within and without the CNS.

In one aspect, the invention provides compounds comprising a megalin ligand or a megalin binding fragment of a megalin ligand conjugated to a therapeutic and/or diagnostic/investigational agent and pharmaceutical compositions of such compounds. In some embodiments, the megalin ligand or megalin binding fragment of such a ligand may be modified as desired to enhance its stability or pharmacokinetic properties (e.g., PEGylation of the RAP moiety of the conjugate, mutagenesis of the RAP moiety of the conjugate).

The present application specifically contemplates a compound comprising a megalin-binding moiety conjugated to an agent of interest. The agent typically may be selected from the group consisting of a therapeutic agent, a diagnostic agent, a marker of a disease of the central nervous system (CNS), a labeled monoclonal antibody which binds a marker of a CNS disorder. Therapeutic agents that are useful in the compounds contemplated herein include but are not limited to proteins, cytotoxic chemotherapeutic agents, protein nucleic acids, siRNA molecules, antisense molecule, and expression constructs that comprise a nucleic acid that encodes a therapeutic protein of interest. The megalin-binding moiety and the agent of interest may be directly linked to each other or alternatively may be linked through a linker, such as e.g., a peptide linker. Preferably, the megalin-binding moiety is a moiety that is transcytosed in vivo. Exemplary such moieties include but are not limited to RAP, thyroglobulin, lipoprotein lipase, lactoferrin, apolipoprotein J/clusterin, apolipoprotein B, apolipoprotein E, tissue type plasminogen activator, uPA, PAI-1, vitamin D-binding protein, vitamin A/retinol-binding protein, $\beta 2$-microglobin, $\alpha 1$-microglobulin, vitamin B12/cobalamin plasma carrier protein, transcobalamin (TC)-B12, PTH, insulin, EGF, prolactin, albumin, apo H, transthyretin, lysozyme, cytochrome-$\alpha,\alpha$-amylase, and Ca2+, and aprotinin. The compound may optionally exclude ApoJ.

The invention contemplates a chimeric molecule for transcytotic delivery into the brain across the blood-brain barrier, the chimeric molecule comprising a megalin ligand conjugated to an active agent to be delivered across the blood-brain barrier by transcytosis, wherein the megalin ligand facilitates transport of the chimeric molecule across the blood-brain barrier. Also contemplated is a chimeric molecule for delivery into the brain by transcytosis across the blood-brain barrier, the chimeric molecule comprising an LRP ligand conjugated to an active agent to be delivered across the blood-brain barrier by transcytosis, wherein the megalin ligand binds preferentially to megalin as compared to LRP1. Any of the compounds or chimeric molecules contemplated herein may be prepared as pharmaceutical compositions comprising the compound or chimeric molecule in a pharmaceutically acceptable carrier, diluent or excipient.

In particular embodiments, the agent is a bioactive protein or peptide covalently linked to the megalin ligand or megalin binding fragment thereof. Such conjugates or chimeric molecules may be formed by synthetic chemical reactions or joined by linker groups. In preferred embodiments, when the active agent is a protein or enzyme, the protein or enzyme is a human protein or enzyme, a fragment of the human protein or enzyme having a biological activity of a native protein or enzyme, or a polypeptide that has substantial amino acid sequence homology with the human protein or enzyme. In some embodiments, the agent is a protein of human or mammalian sequence, origin or derivation, in certain aspects, the protein forms a fusion protein with the megalin ligand or megalin binding fragment of such a ligand. The active agent polypeptide portion of the fusion protein may be a substance having therapeutic activity such as a growth factor, lymphokine or peptide drug. The agent may be an enzyme or other bioactive protein or polypeptide. In other embodiments, the agent is an enzyme or protein whose deficiency causes a human disease such as Pompe's disease (e.g. alpha-glucosidase). In other embodiments, the enzyme is selected for its beneficial effect. In other embodiments, the conjugate is formed by non-covalent bonds between the carrier and an antibody to which the active agent is attached.

The megalin ligand can also be of human or mammalian sequence origin or derivation. In preferred embodiments, the megalin ligand is selected from the group consisting of RAP, thyroglobulin, lipoprotein lipase, lactoferrin, apolipoprotein J/clusterin, apolipoprotein B, apolipoprotein E, tissue type plasminogen activator, uPA, PAI-1, vitamin D-binding protein, vitamin A/retinol-binding protein, β2-microglobin, a 1-microglobulin, vitamin B12/cobalamin plasma carrier protein, transcobalamin (TC)-B12, PTH, insulin, EGF, prolactin, albumin, apo H, transthyretin, lysozyme, cytochrome-c, α-amylase, and aprotinin.

In yet other embodiments of the invention, in each of its aspects, any of the above megalin ligands are identical to the amino acid sequence of the given ligand from a human or mammalian source. In other embodiments, the megalin ligand is the native protein from the human or mammal. In other embodiments, the RAP or RAP polypeptide is substantially homologous (i.e., at least 80%, 85%, 90%, 95%, 98%, or 99% identical in amino acid sequence) to the native protein over a length of at least 25, 50, 100, 150, or 200 amino acids, or the entire length of the megalin ligand.

In preferred embodiments, the megalin ligand is RAP or a megalin binding fragment of RAP. In other embodiments, the subject to which the conjugate is to be administered is human.

In a further aspect, the invention provides a method for delivering therapeutic and/or diagnostic/investigational agents to the central nervous system using the megalin ligand/megalin receptor carrier system to transport such agents across the BBB formed by the capillary endothelial cells which are closely sealed by tight junctions. The invention thereby provides a novel route of administering agents with a site of action within the central nervous system. In a further embodiment, a modulator of megalin is co-administered to modulate the therapeutic or adverse effects of such a conjugate.

The invention contemplates a method of delivering an agent into the central nervous system of an animal comprising administering the animal the agent conjugated to a megalin binding moiety, wherein the transport of the agent conjugated to the megalin-binding moiety across the blood brain barrier of the animal is greater than the transport of the agent in the absence of conjugation to the megalin binding moiety. Also contemplated are methods of increasing transcytosis of an agent, comprising conjugating the agent to a megalin-binding moiety, wherein transcytosis of the agent when conjugated to the megalin-binding moiety is greater than the transcytosis of the agent in the absence of the conjugation. The invention also contemplates treating a disorder in a mammal comprising administering to the animal a therapeutic agent conjugated to a megalin binding moiety. In the methods of the invention the megalin-binding moiety typically improves transcytosis of the therapeutic agent being delivered. Another method of the invention is for delivering a therapeutic enzyme to a lysosomal compartment in a cell expressing megalin, comprising contacting the cell with a composition comprising the therapeutic enzyme conjugated to a megalin-binding moiety, wherein the uptake of the therapeutic enzyme into the lysosomal compartment of the cell is mediated through megalin present on the surface of the cell.

In some embodiments, the conjugated chimeric molecules which comprise a megalin ligand and an active agent comprise more than one therapeutic active agent useful in treating the same condition or disorder linked to a single megalin ligand. In some embodiments, from about 1 to about 5 or from 2 to 10 molecules of the active agent are attached to one megalin ligand molecule to be administered to a patient having the disease, condition or disorder.

In another aspect, the invention provides methods for using the megalin receptor-based delivery in the treatment of diseases, disorders, or conditions. In one group of embodiments, the conjugates of active agents with a megalin ligand may be used to treat a CNS condition or disorder. In one group of particularly preferred embodiments to be treated, the CNS condition or disorder to be treated is a brain tumor or other neoplasia (e.g., a CNS tumor such as a glioblastoma). Such tumors or neoplasia may be primary tumors or may be metastases. In these embodiments, the compounds according to the invention may comprise a megalin ligand or a megalin binding fragment of such a ligand conjugated to a cancer chemotherapeutic agent. Preferred compounds have from about 1 to about 20 molecules of the chemotherapeutic agent covalently linked to each megalin ligand moiety. Such compounds are excellent vehicles for enhanced delivery of chemotherapeutic agents to brain tumors and other neoplasia localized in or around the brain, and for improved treatment of such tumors and neoplasia. In some embodiments, the cancer chemotherapeutic agents conjugated to a megalin ligand polypeptide may be the same or different. For instance, from 1 to 3 different chemotherapeutic agents may be attached in the same or a different moles megalin ligand polypeptide per mole active agent ratio (e.g., 1:1; 1:2; 1:3; 1:4; and 1:5 to 1:10) with respect to the megalin ligand or megalin binding fragment of such a chimeric compound.

Preferred chemotherapeutic agents for such conjugates are cytotoxic chemotherapeutic agents and include, but are not limited to adriamycin, cisplatin, 5-fluorouracil, camptothecin, and paclitaxel. In another embodiment, the present invention provides a method of treating a patient with a brain or CNS tumor or glioblastoma by administering to the patient a therapeutically effective amount of megalin ligand conjugated to the chemotherapeutic agent. In another embodiment, the present invention provides for a method for delivering a compound of interest through the blood-brain barrier of a subject into the brain parenchyma where the compound is a chemotherapeutic able to interfere with the division of the tumor cells and are toxic for dividing cells. These compounds are liberated in the lysosomes following degradation of the vector and can diffuse through the lysosomal membrane and enter the nucleus.

In another group of embodiments, the present invention provides compounds, pharmaceutical compositions, and methods for treating neurologic and psychiatric diseases and CNS diseases, disorders and conditions, including, but not limited to, Alzheimer's Disease, Parkinson's Disease, Multiple Sclerosis, and Amylotrophic Lateral Sclerosis. In some embodiments, the compounds of the invention comprise a megalin ligand polypeptide conjugated to a therapeutic agent for treating such diseases, disorders and conditions. In a preferred group of embodiments, the therapeutic agent is a peptide including, but not limited to, Nerve Growth Factor, other peptide hormones or growth factors, and peptide neurotransmitters. In another embodiment, the present invention provides for a method for delivering an active agent through the blood-brain barrier of a subject into the brain parenchyma where the active agent is a neurotrophic factors including, but not limited to, Nerve Growth Factor, Brain-Derived Neurotrophic Factor, Neurotrophin-3, Neurotrophin-4/5, aFGF, bFGF, CNTF, Leukaemia Inhibitory Factor, Cardiotrophin-1, TGFb, BMPs, GDFs, Neurturin, Artemin, Persephin, EGF, TGFa, Neuregulins, IGF-1, IGF-2, ADNF and PDGFs. Other factors such as caspase inhibitors can also be conjugated as the active agent member of the compound. In other embodiments, the active agent is a therapeutic antibody directed toward a constituent of the CNS. In other embodiments, the active agent is an antimicrobial agent for treating or preventing a CNS infection or an immunomodulator such as a lymphokine.

In some embodiments, the chimeric molecule that is a conjugate of a megalin ligand (or megalin binding fragment thereof) and an active agent is administered to treat a disease or condition selected from the group consisting of neurological diseases including, but not limited to, conditions such as Alzheimer's Disease, Parkinson's Disease, schizophrenia, and epilepsy; neurological cancers, such as primary brain tumors including glioma, meningioma, neurinoma, pituitary adenoma, medulloblastoma, craniopharyngioma, hemangioma, epidermoid, sarcoma and intracranial metastasis from other tumor sources, and neurological infections or neurological inflammatory conditions.

Other diseases of the brain also may be treated. Diseases of the brain fall into two general categories: (a) pathologic processes such as infections, trauma and neoplasm; and, (b) diseases unique to the nervous system which include diseases of myelin and degeneration of neurons. Brain-related degenerative diseases resulting from a decrease in neuronal survival include, for example, Alzheimer's disease, Parkinson's disease, Huntington's disease, ischemia-related disease and stroke, amyotrophic lateral sclerosis (ALS), spinal muscular atrophy, cerebellar degeneration. Demyelinating diseases include multiple sclerosis (MS) and its variants and perivenous encephalitis. Other diseases in which the principal pathologic change is primary demyelination, but which are usually classified in other categories include leukodystrophies such as metachromatic leukodystrophy due to deficiency of arylsulfatase A, Krabbe's disease due to deficiency of galactocerebroside beta-galactosidase, adrenoleukodystrophy and adrenomyeloneuropathy, and post-viral diseases such as progressive multifocal leukoencephalopathy, acute disseminated encephalomyelitis, acute necrotizing hemorrhagic leukoencephalitis. In addition there are mitochondrial encephalomyopathies. It is contemplated that the conjugates of the invention may be used in the treatment of such diseases.

In still other aspects, the megalin ligand conjugates of the invention can be used to treat non-CNS (i.e., non-BBB delimited diseases, such as cancers, diseases and conditions of non-CNS organs). For example, conjugated agents can be used to treat conditions affecting a patient's muscles.

In other aspects, the invention provides methods of treating tissues or organs having proportionately greater, preferably more than two-fold, amounts of megalin receptors on their cells than other tissues or organs. The selective biodistribution of megalin ligand-conjugated active agents can enhance the selective targeting of such conjugated agents to specific organs.

In a still further aspect, the invention provides a method for using the RAP/megalin carrier system in the diagnosis of diseases, disorders, or conditions. The present invention provides screening assays for identifying or selecting conjugates of megalin ligand with active agents that can prevent, ameliorate, or treat a CNS disease or disorder by measuring the transcytosis of such agents in in vitro models or by measuring the ability of such conjugates to reach or bind to the brain parenchyma in vivo. Transcytosis or delivery can be assessed by labeling the conjugate and then monitoring or detecting the location or transport of the label in the test chamber for an in vitro method or in a tissue compartment(s) in an in vivo method. In addition, a therapeutic effect or other biological effect of the conjugate can be used to monitor for passage of the conjugate into the parenchyma of the central nervous system. In preferred embodiments, the CNS condition is a brain tumor.

In another aspect, the invention provides a method of delivering a therapeutic enzyme to a lysosome in a brain cell of a subject, comprising: (i) administering a compound comprising megalin ligand (or megalin binding fragment thereof) conjugated to the therapeutic enzyme, (ii) transporting such compound across the capillary endothelium; (iii) contact of such compound with an megalin receptor on the cell, thereby facilitating entry of such compound into such cell by endocytosis; and (iv) delivery to lysosomes within the cell. In certain other aspects, the invention provides such compounds, compositions, and methods for delivering a therapeutic agent or diagnostic agent to the lysosome of a cell.

In yet another aspect, the invention provides a megalin ligand (or megalin binding fragment thereof) conjugated to a therapeutic enzyme, and method of treating lysosomal storage diseases by administering such a conjugate, wherein the ligand-enzyme complex binds to megalin receptor and is transported across the cell membrane, enters the cell and is delivered to the lysosomes within the cell. In some embodiments, the invention also provides a method of treating a lysosomal storage disease in a patient by administering a megalin ligand (or megalin binding fragment thereof) conjugated to a therapeutic agent which is a protein or enzyme deficient in the lysosomes of a subject having such a disease (e.g., enzyme replacement therapy). Such conjugates are particularly useful, for example, in the treatment of lysosomal storage diseases such as MPS I, MPS II, MPS III A, MPS III B, Metachromatic Leukodystrophy, Gaucher, Krabbe, Pompe, CLN2, Niemann-Pick and Tay-Sachs disease wherein a lysosomal protein deficiency contributes to the disease state. In yet other embodiments, the invention also provides a pharmaceutical composition comprising megalin ligand (e.g., RAP) covalently linked to a protein or enzyme deficient in a lysosomal storage disease.

Thus the invention contemplates methods of treating a lysosomal storage disease (LSD) in a subject comprising administering to the subject a composition comprising a megalin-binding moiety conjugated to a therapeutic agent used in the treatment of the LSD, in an amount effective to ameliorate the symptoms of the LSD. Typically, in such a method the composition is a pharmaceutical composition and is administered in an amount effective to decrease the amount of storage granules present in the brain tissue of the mammal. The administration may be intrathecal administration into the central nervous system of the mammal. Preferably, the composition is administered in an amount effective to decrease the amount of storage granules present in the meningeal tissue of the mammal. The symptoms of LSD are monitored using techniques known to those of skill in the art and are typically monitored through routine assessment of history, physical examination, echocardiography, electrocardiography, magnetic resonance imaging, polysomnography, skeletal survey, range of motion measurements, corneal photographs, and skin biopsy.

In some embodiments, the compounds, compositions, and methods of the invention can be used to treat such lysosomal storage diseases as Aspartylglucosaminuria, Cholesterol ester storage disease/Wolman disease, Cystinosis, Danon disease, Fabry disease, Farber Lipogranulomatosis/Farber disease, Fucosidosis, Galactosialidosis types I/II, Gaucher disease types I/II/III Gaucher disease, Globoid cell leukodystrophy/Krabbe disease, Glycogen storage disease II/Pompe disease, GM1-Gangliosidosis types I/II/III, GM2-Gangliosidosis type I/Tay-Sachs disease, GM2-Gangliosidosis type II Sandhoff disease, GM2-Gangliosidosis, alpha-Mannosidosis types I/II, alpha-Mannosidosis, Metachromatic leukodystrophy, Mucolipidosis type I/Sialidosis types I/II Mucolipidosis types II/III I-cell disease, Mucolipidosis type IIIC pseudo-Hurler polydystrophy, Mucopolysaccharidosis type I, Mucopolysaccharidosis type II Hunter syndrome, Mucopolysaccharidosis type IIIA Sanfilippo syndrome, Mucopolysaccharidosis type IIIB Sanfilippo syndrome, Mucopolysaccharidosis type IIIC Sanfilippo syndrome, Mucopolysaccharidosis type IIID Sanfilippo syndrome, Mucopolysaccharidosis type IVA Morquio syndrome, Mucopolysaccharidosis type IVB Morquio syndrome, Mucopolysaccharidosis type VI, Mucopolysaccharidosis type VII Sly syndrome, Mucopolysaccharidosis type IX, Multiple sulfatase deficiency, Pompe, Neuronal Ceroid Lipofuscinosis, CLN1 Batten disease, Neuronal Ceroid Lipofuscinosis, CLN2 Batten disease, Niemann-Pick disease types A/B Niemann-Pick disease, Niemann-Pick disease type C1 Niemann-Pick disease, Niemann-Pick disease type C2 Niemann-Pick disease, Pycnodysostosis, Schindler disease types III Schindler disease, and Sialic acid storage disease. In particularly preferred embodiments, the lysosomal storage disease is MPS III, MLD, or GM1.

In still another embodiment, the present invention provides for a method of enzyme replacement therapy by administering a therapeutically effective amount of a conjugate to a subject in need of the enzyme replacement therapy, wherein the conjugate comprises a megalin ligand (or megalin binding fragment thereof) linked to an enzyme via a linker, wherein the cells of the patient have lysosomes which contain insufficient amounts of the enzyme to prevent or reduce damage to the cells, whereby sufficient amounts of the enzyme enter the lysosomes to prevent or reduce damage to the cells. The cells may be within or without the CNS and may but need not be set off from the blood by capillary walls whose endothelial cells are closely sealed to diffusion of an active agent by tight junctions.

In some embodiments, the megalin ligand conjugates with an active agent comprise more than one active agent for treating a lysosomal storage disease linked to a single megalin ligand. In some embodiments, from about 1 to about 5 or from 2 to 10 molecules of the active agent of interest are bound to a single megalin ligand molecule.

In a particular embodiment, the invention provides compounds comprising a megalin ligand bound to an active agent having a biological activity which is reduced, deficient, or absent in the target lysosome of the subject to which the compound is administered. In preferred embodiments, the megalin ligand (or megalin binding fragment thereof) is covalently bound to the active agent. Preferred active agents include, but are not limited to aspartylglucosaminidase, acid lipase, cysteine transporter, Lamp-2, alpha-galactosidase A, acid ceramidase, alpha-L-fucosidase, beta-hexosaminidase A, GM2-activator deficiency, alpha-D-mannosidase, beta-D-mannosidase, arylsulfatase A, saposin B, neuraminidase, alpha-N-acetylglucosaminidase phosphotransferase, phosphotransferase γ-subunit, alpha-L-iduronidase, iduronate-2-sulfatase, heparan-N-sulfatase, alpha-N-acetylglucosaminidase, acetylCoA:N-acetyltransferase, N-acetylglucosamine 6-sulfatase, galactose 6-sulfatase, alpha-galactosidase, N-acetylgalactosamine 4-sulfatase, hyaluronoglucosaminidase, palmitoyl protein thioesterase, tripeptidyl peptidase I, acid sphingomyelinase, cholesterol trafficking, cathepsin K, beta-galactosidase B, α-glucosidase, and sialic acid transporter. In a preferred embodiment, alpha-L-iduronidase, α-glucosidase or N-acetylgalactosamine 4-sulfatase is the enzyme.

In specific embodiments, the disease being treated by the methods provided herein mucopolysaccharidosis, more particularly, mucopolysaccharidosis I. In specific embodiments, the mammal with the LSD demonstrates about 50% or less of a normal α-L-iduronidase activity. Typically, the pharmaceutical composition is administered at a dose of between about 0.001 mg/kg body weight and 0.5 mg/kg body weight of the human α-L-iduronidase administered weekly to a subject suffering from a deficiency thereof. These are merely exemplary and those of skill in the art may employ other doses to achieve therapeutically effective results. Further it should be understood that dosage form is cited herein as mg/kg body weight, however, those of skill in the art will be aware of other dosage measurements that may be used instead. In some embodiments, the pharmaceutical composition is administered at a dose of between about 0.01 mg/1 5 cc of CSF to about 5.0 mg/15 cc of CSF of the mammal of the human α-L-iduronidase is administered weekly to a subject suffering from a deficiency thereof. In the treatment of LSD, the administration of the megalin-binding moiety conjugated to a therapeutic agent preferably results in normalization of developmental delay and regression in the subject, reduction in high pressure hydrocephalus, reduction in spinal cord compression in the subject, and reduction in number and/or size of perivascular cysts around the brain vessels of the subject. Where the administration is intrathecal, such administration may comprise introducing the pharmaceutical composition into a cerebral ventricle. The methods may comprise intrathecal administration that introduces the pharmaceutical composition into the lumbar area or the cisterna magna. Intrathecal administration may be effected through the use of e.g., an infusion pump. It may be a continuous administration over a period of time. Typically, the period of time may be at least several days. Preferably, the mammal being treated is a human.

Also contemplated is a method of promoting the breakdown of glycosaminoglycan (GAG) in a brain cell of a subject having lysosomal storage disease, the method comprising administering to the subject a pharmaceutical composition comprising an enzyme deficient in the lysosomal storage disease conjugated to a megalin-binding moiety in an amount effective to reduce the amount of GAG present in the brain cell as compared to the amount of GAG present in the cell prior to the administration. Preferably, the brain cell is a neuron, glial cell, microglial cell, astrocyte, oligodendroglial cell, perivascular cell, perithelial cell, meningeal cell, ependymal cell, arachnoid granulation cell, arachnoid membrane, dura mater, pia mater and choroid plexus cell. In these methods, the subject may manifest a symptom of high pressure hydrocephalus and the administering reduces the amount of CSF fluid in the meningeal tissue of the subject. In other aspects, the number of lysosomal storage granules in the cell are reduced as compared to the number of lysosomal storage granules present in a similar cell in the absence of administration of the conjugate. In other embodiments, the number of lysosomal storage granules in the cell are reduced as compared to the number of lysosomal storage granules present in a similar cell treated with enzyme alone without conjugation to the megalin-binding moiety.

In another aspect, the invention provides screening assays for identifying megalin ligand (or megalin binding fragment thereof) conjugated to active agent that can prevent, ameliorate, or treat a lysosomal storage disease by contacting a cell containing a lysosome with the conjugate and determining whether the conjugate delivers the agent to the lysosome. The delivery can be assessed by labeling the conjugate and then monitoring or detecting the location of the label in the cell or by determining the effect of the conjugate on the amount of the storage material found in the lysosome. In a preferred embodiment, the agent is a protein or enzyme deficient in the lysosomal storage disease. In another embodiment, the cell is deficient in the agent conjugated to the megalin ligand.

In another embodiment, the present invention provides for a method for identifying an agent that can prevent, ameliorate or treat a lysosomal storage disease, by administering megalin ligand (or megalin binding fragment thereof) conjugated enzyme to a cell, wherein absence of the enzyme causes the lysosomal storage disease; and determining whether the agent reduces damage to the cell compared to damage to the cell if the conjugated agent was not administered to the cell. In certain embodiments, the method is a high throughput assay.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE FIGURES

The following drawings form part of the present specification and are included to further illustrate aspects of the present invention. The invention may be better understood by reference to the drawings in combination with the detailed description of the specific embodiments presented herein.

FIG. 2. Preparation of expression constructs encoding fusions between human RAP and human glucosidase (GAA), alpha-L-iduronidase (IDU) and glial-derived neurotrophic factor (GDNF). (RAPF primer: SEQ ID NO:12; RAPR primer SEQ ID NO:13; GAA forward primer SEQ ID NO:14; GAA reverse primer SEQ ID NO:15; IDU forward primer SEQ ID NO:16; IDU reverse primer SEQ ID NO:17; GDNF forward primer SEQ ID NO:18; GDNF reverse primer SEQ ID NO:19; RAPBACF primer SEQ ID NO:20.)

FIG. 3. Nucleotide and protein sequences of the RAP-GAA fusion (nucleotide sequence: SEQ ID NO:6; protein sequence: SEQ ID NO:7).

FIG. 4. Nucleotide and protein sequence of RAP-IDU fusion (nucleotide sequence: SEQ ID NO:8; protein sequence: SEQ ID NO:9).

FIG. 5. Nucleotide and protein sequence of RAP-GDNF fusion (nucleotide sequence: SEQ ID NO:10; protein sequence: SEQ ID NO:11).

FIG. 10. Binding of RAP and RAP-lysosomal enzyme fusion to LRP.

FIG. 13. RAP-alpha-glucosidase uptake by human Pompe fibroblasts.

FIG. 14. Multiple alignment of amino acid sequences of RAP from different species: human (SEQ ID NO:21); mouse (SEQ ID NO:22); rat (SEQ ID NO:23); chicken (SEQ ID NO:24); zebrafish (SEQ ID NO:25); fruit fly (SEQ ID NO:26); mosquito (SEQ ID NO:27); flatworm (SEQ ID NO:28).

FIG. 15. SEQ ID NO:1, amino acid sequence of human RAP.

FIG. 16. SEQ ID NO:2, amino acid sequence of the 28 kD RAP polypeptide.

FIG. 17. Transcytosis is bovine brain capillary endothelial cells.

FIG. 19A Gel and blot analysis of RAP fusions: RAP-IDU, A; RAP-GAA, B. Coomassie Blue staining, lane 1; anti-RAP antibody, lane 2; anti-IDU or anti-GAA antibody, lane 3. FIG. 19B. Kinetic analysis of rhIDU and RAP-IDU: Proteins (1 nM) were incubated at room temperature for 5 minutes in different concentrations of 4-MUI. Derived $V_{max}$ and $K_m$ values are listed in Table A. FIG. 19C. In vitro proteolysis of RAP fusions: Fusions were treated with a mixture of cathepsins, resolved on SDS-PAGE gels and stained with Coomassie Blue. Undigested RAP-GAA fusion, lane 1; proteolyzed RAP-GAA fusion, lane 2; rhGAA, lane 3; undigested RAP-IDU fusion, lane 4; proteolyzed RAP-IDU fusion, lane 5; rhIDU, lane 6; RAP, lane 7; molecular weight markers, lane 8.

FIG. 20A. Fluorophore-assisted carbohydrate electrophoresis (FACE) of rhGAA (A), RAP-GAA (A), rhIDU (B) and RAP-IDU (B): N-linked oligosaccharides were released, fluorescently labeled at the reducing terminus and electrophoresed. Fluorescent bands were analyzed on a FACE imager system. Band intensity is proportional to the molar amount of particular oligosaccharides present. Oligoglucose ladder calibrated in degree of polymerization (DP) units, lane 1; rhGAA (A) or rhIDU (B), lane 2; RAP-GAA (A) or RAP-IDU (B), lane 3. The prominent band near the bottom of lane 2 in both A and B marked by the arrow is Bis-7. FIG. 20B. Isoelectric focusing analysis of RAP-GAA for complex oligosaccharides: Proteins were treated with *Clostrium perfringens* neuraminidase, resolved on PhastGels and silver stained. Untreated rhIDU (positive control), lane 1; rhIDU treated with neuraminidase, lane 2; untreated RAP-GAA, lane 3; RAP-GAA treated with neuraminidase, lane 4; pI standards, lane 5. FIG. 20C. Endo H and N-glycanase digestion of proteolyzed RAP-GAA and RAP-IDU: Fusions were proteolyzed with a mixture of cathepsins, treated with Endo H or N-glycanase, resolved on SDS-PAGE gels and stained with Coomassie Blue. Molecular weight standards, lanes 1 and 10. RAP-GAA, lane 2; proteolyzed RAP-GAA, lane 3; proteolyzed, endo H digested RAP-GAA, lane 4; proteolyzed, N-glycanase digested RAP-GAA, lane 5; RAP-IDU, lane 6; proteolyzed RAP-IDU, lane 7; proteolyzed, endo H digested RAP-IDU, lane 8; proteolyzed, N-glycanase digested RAP-IDU, lane 9. Interpolated molecular weights are printed under each band.

FIG. 22A: Uptake of RAP-IDU and rhIDU into GM1391 fibroblasts: Different concentrations of proteins were incubated with fibroblasts for 2 hours. After washing, fibroblasts were lysed and uptake was measured by enzymatic assay. Curves were fitted and constants derived as described. Inset: Plot of rhIDU data alone. FIG. 22B: Uptake of RAP-GAA and rhGAA into GM244 fibroblasts: Different concentrations of proteins were incubated with fibroblasts for 2 hours. After washing, fibroblasts were lysed and uptake was measured by enzymatic assay. Curves were fitted and constants derived as described. Inset: Plot of rhGAA data alone. FIG. 22C: Inhibition of RAP-IDU uptake into GM1391 fibroblasts: RAP-IDU (3 nM) was incubated with fibroblasts in the presence of different concentrations of RAP for 2 hours. After washing, fibroblasts were lysed and uptake was measured by iduronidase enzymatic assay. FIG. 22D: Inhibition of RAP-GAA uptake into GM244 fibroblasts: RAP-GAA (5 nM) was incubated with fibroblasts in the presence of different inhibitors for 2 hours. After washing, fibroblasts were lysed and uptake was measured by enzymatic assay. FIG. 22E. Inhibition of RAP-GAA (gray) and rhGAA (black) uptake into C6 glioma cells: Proteins (5 nM) were incubated with C6 glioma cells in the presence of inhibitors for 2 hours. After washing, fibroblasts were lysed and uptake was measured by enzymatic assay. ND=not done. FIG. 22F Inhibition of RAP-GAA uptake (gray) and rhGAA uptake (black) into C2C12 myoblasts: RAP-GAA and rhGAA, both at 5 nM, were incubated with cells in the presence of inhibitors for 2 hours. After washing, fibroblasts were lysed and uptake was measured by enzymatic assay.

FIG. 25A. Clearance of stored glycosaminoglycan in Hurler fibroblasts by rhIDU and RAP-IDU: Cells were labeled in triplicate with $^{35}$S-sulfate in the presence of rhIDU or RAP-IDU for 48 hours. Labeled cells were then washed, lysed and assayed for radioactivity and total protein. FIG. 25B: SDS-PAGE analysis of proteins used for experiment, stained with Coomassie Blue. RAP-IDU, lane 1; rhIDU, lane 2.

DESCRIPTION OF THE PREFERRED EMBODIMENTS

Figure 1:
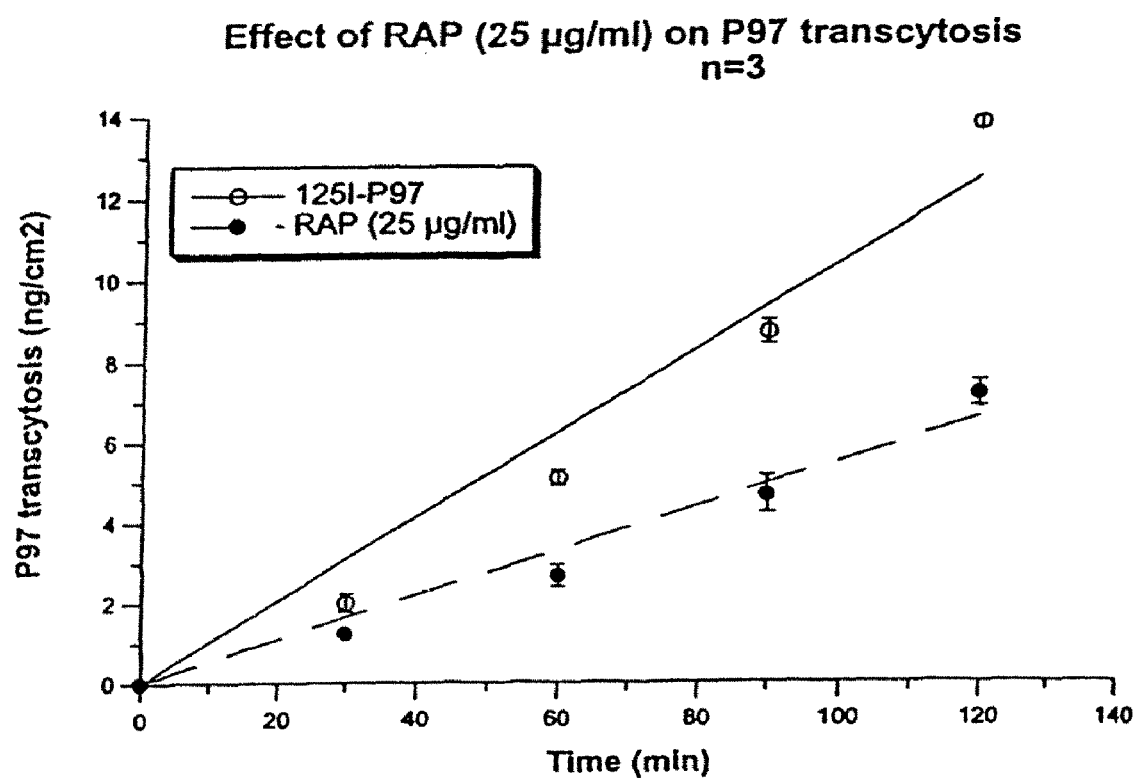
FIG. 1. Effect of RAP on [$^{125}$I]-p97 transcytosis across BBCEC monolayers.

Despite the fact that there have been significant advances made in the design and delivery of therapeutic agent across the blood brain barrier, there remains a need for new agents that may produce additional compounds that can mediate the transcytosis of therapeutic agents.

The present invention relates to the discovery that RAP and RAP polypeptides selectively bind to megalin receptors. RAP is a particularly effective megalin ligand for delivering active agents conjugated to it across the blood brain barrier, to the lysosomes within a cell, and to the intracellular compartment of cells bearing megalin receptors. Other megalin ligands also are exemplified herein as being useful in mediating such delivery. Compounds comprising megalin ligand (or megalin binding fragment thereof) conjugated to an active agent are useful in the diagnosis and treatment of a variety of CNS and non-CNS diseases, conditions, and disorders, including but not limited to, in particular, cancer and lysosomal storage diseases. Methods and compositions for exploiting these findings are described in further detail below.

1. DEFINITIONS

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

"Brain tumors and other neoplasia in or around the brain" as used herein includes both primary tumors and/or metastases that develop in or around the brain. It may also mean metastases of brain tumors that migrate elsewhere in the body, but remain responsive to RAP or RAP polypeptide conjugates with chemotherapeutic agents. Many types of such tumors and neoplasia are known. Primary brain tumors include glioma, meningioma, neurinoma, pituitary adenoma, medulloblastoma, craniopharyngioma, hemangioma, epidermoid, sarcoma and others. Fifty percent of all intracranial tumors are intracranial metastasis. As used herein, tumors and neoplasia may be associated with the brain and neural tissue, or they may be associated with the meninges, skull, vasculature or any other tissue of the head or neck. Such tumors are generally solid tumors, or they are diffuse tumors with accumulations localized to the head. Tumors or neoplasia for treatment according to the invention may be malignant or benign, and may have been treated previously with chemotherapy, radiation and/or other treatments.

The term "effective amount" means a dosage sufficient to produce a desired result on a health condition, pathology, and disease of a subject or for a diagnostic purpose. The desired result may comprise a subjective or objective improvement in the recipient of the dosage. "Therapeutically effective amount" refers to that amount of an agent effective to produce the intended beneficial effect on health.

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

A "subject" of diagnosis or treatment is a human or non-human animal, including a mammal or a primate.

"Treatment" refers to prophylactic treatment or therapeutic treatment or diagnostic treatment.

A "prophylactic" treatment is a treatment administered to a subject who does not exhibit signs of a disease or exhibits only early signs for the purpose of decreasing the risk of developing pathology. The conjugate compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective. The conjugate compounds of the invention may be given as a therapeutic treatment or for diagnosis.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a pharmacologically effective amount of a RAP polypeptide conjugated to an active agent and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a conjugate compound of the present invention and a pharmaceutically acceptable carrier.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use including, e.g., metal salts (sodium, potassium, magnesium, calcium, etc.) and salts of ammonia or organic amines.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular conjugate employed and the effect to be achieved, and the pharmacodynamics associated with each compound in the host.

"Modulate," as used herein, refers to the ability to alter, by increase or decrease (e.g., to act as an antagonist or agonist).

"Increasing relative delivery" as used herein refers to the effect whereby the accumulation at the intended delivery site (e.g., brain, lysosome) of a RAP-conjugated active agent is increased relative to the accumulation of the unconjugated active agent.

"Therapeutic index" refers to the dose range (amount and/or timing) above the minimum therapeutic amount and below an unacceptably toxic amount.

"Equivalent dose" refers to a dose, which contains the same amount of active agent.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A first sequence is an "antisense sequence" with respect to a second sequence if a polynucleotide whose sequence is the first sequence specifically hybridizes with a polynucleotide whose sequence is the second sequence.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially homologous" or "substantially identical" in the context of two nucleic acids or polypeptides, generally refers to two or more sequences or subsequences that have at least 40%, 60%, 80%, 90%, 95%, 98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of either or both comparison biopolymers.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman, Adv. Appl. Math. 2:482 (1981), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle, J. Mol. Evol. 35:351-360 (1987). The method used is similar to the method described by Higgins and Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another algorithm that is useful for generating multiple alignments of sequences is Clustal W (Thompson et al. Nucleic Acids Research 22: 4673-4680, 1994).

Another example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues;

always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, Proc. Natl. Acad. Sci. USA 89:10915, 1989).

In addition to calculating percent sequence identity, the BLAST algorithm also performs a statistical analysis of the similarity between two sequences (see, e.g., Karlin and Altschul, Proc. Nat'l. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described herein.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the conjugates of the invention are substantially pure or isolated. In some embodiments, the conjugates of the invention are substantially pure or isolated with respect to the macromolecular starting materials used in their synthesis. In some embodiments, the pharmaceutical composition of the invention comprises a substantially purified or isolated conjugate of a RAP polypeptide and the active agent admixed with one or more pharmaceutically acceptable excipient.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., PD. Fahrlander and A. Klausner, Bio/Technology (1988) 6:1165.) Quantitation of the signal is achieved by, e.g., scintillation counting, densitometry, or flow cytometry.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

II. MEGALIN

Megalin, also referred to as LRP2 is a large (600 kDa), is a member of the LRP family of receptors (Hussain et al. Annu Rev Nutr., 19:141-72 1999; Christensen and Birn Am. J. Physiol. Renal. Physiol., 280:F562-573, 2001). Like all members of the LRP family, megalin binds RAP with high affinity (Czekay et al., Mol. Biol. Cell. 8(3):517-32, 1997). Unique among the LRP family, however, megalin is expressed only on the apical surface of a restricted set of epithelial cell layers, including those in the kidney proximal tubule, the thyroid, the epididymis, the alveolae and the ciliary body of the eye (Zheng et al. J Histochem Cytochem., 42(4):531-42, 1994). Megalin is also expressed on the luminal surface of the brain capillary endothelium, a classical squamous epithelial cell layer (Chun, et al. Exp Neurol., 157(1):194-201, 1999). Megalin on the brain capillary endothelium has been previously demonstrated to mediate transcytosis of one of its ligands, apoJ, across the blood-brain barrier in vitro (Zlokovic et al., Proc. Nat'l Acad. Sci., USA 93(9):

4229-34 1996; Zlokovic Life Sci., 59(18):1483-97, 1996). Apical-to-basolateral transcytosis of ligands by megalin has also been documented in the kidney and thyroid (Marino et al. J Am Soc Nephrol., 12(4):637-48, 2001; Marino et al., Thyroid, 11(1):47-56, 2001).

In the present application it is shown that megalin mediates the transcytosis of RAP across tight MDCK cell layers. This application for the first time shows that it is megalin rather than LRP1 that mediates the transcytosis of RAP and other ligands across such cell layers. Given this finding, it is contemplated that the use of any and all megalin ligands will be excellent candidates for mediating the delivery of active agents through targeted delivery in the kidney, thyroid, epididymis, eye and brain cells. Thus, in particular embodiments, while it is remains desirable to use other LRP family members to mediate transcytosis of an active agent across the BBB, in particularly preferred embodiments, such transcytosis is mediated through the conjugation of the active agent to a megalin ligand.

Thus, the present application contemplates that ligands with enhanced specificity for megalin over LRP1 will be particularly useful as vectors for the transport of proteins and small molecules from blood-to-brain. In certain embodiments, the ligands optionally exclude ApoJ. This advantage accrues from avoiding LRP1-mediated clearance in the liver, increasing serum residence time and, consequently, brain influx.

III. OTHER LRP RECEPTORS

While megalin is the preferred receptor through which active agent transcytosis is achieved, it is contemplated that other LRP receptors will nonetheless be useful for effecting such transcytosis. "LRP" refers to members of the low-density lipoprotein receptor family including the low-density lipoprotein receptor-related protein 1 (LRP1). LRP1 is a large protein of 4525 amino acids (600 kDa), which is cleaved by furin to produce two subunits of 515-(alpha) kD and 85-(B) kDa that remain non-covalently bound. LRP is expressed on most tissue types. Other members of the low-density lipoprotein (LDL) receptor family include LDL-R (132 kDa); LRP/LRP1 and LRP1B (600 kDa); Megalin ((LRP2), 600 kDa); VLDL-R (130 kDa); ER-2 (LRP-8, 130 kDa); Mosaic LDL-R (LR11, 250 KDa); and other members such as LRP3, LRP6, and LRP-7. Characteristic features of the family include cell-surface expression; extracellular ligand binding domain repeats (DxSDE); requirement of Ca++ for ligand binding; recognition of RAP and ApoE; EGF precursor homology domain repeats (YWTD); single membrane spanning region; internalization signals in the cytoplasmic domain (FDNPXY); and receptor mediated endocytosis of various ligands. Some members of the family, including LRP1 and VLDLR, participate in signal transduction pathways.

LRP ligands refer to a number of molecules that are known to bind LRP. These molecules include, for instance, lactoferrin, RAP, lipoprotein lipase, ApoE, Factor VIII, beta-amyloid precursor, alpha-2-macroglobulin, thrombospondin 2 MMP-2 (matrix metalloproteinase-2), MPP-9-TIMP-1 (tissue inhibitor of matrix metalloproteinase-1); uPA (urokinase plasminogen activator):PAI-I (plasminogen activator inhibitor-1):uPAR (uPA receptor); and tPA (tissue plasminogen activator):PAI-1:uPAR.

LRP1 is believed to be a multifunctional receptor with clustering of cysteine-rich type repeats. A binding repeat, resembling those found in the LDL receptor, is the molecular principle for the ability to bind a variety of ligands that were previously thought to be unrelated. These include the ligands described in the previous paragraph in addition to: pseudomonas exotoxin A, human rhinovirus, lactoferrin and the so-called receptor associated protein (RAP). See, Meilinger et al., FEBS Lett, 360:70-74 (1995). LRP1 is has the GenBank Accession No.: X 13916 and SwissProt Primary Accession No.: Q07954. Alternative names for the LRP1 gene/protein include: Low-density lipoprotein receptor-related protein 1 [precursor], LRP, Alpha-2-macroglobulin receptor, A2MR, Apolipoprotein E receptor, ApoER, CD91, LRP1 or A2MR.

Members of the LRP family are well expressed on capillary endothelium and on CNS cell types including neurons and astrocytes (e.g., LDL receptor, Megalin, LRP). LRP receptors endocytose bound ligand and have been demonstrated to transcytose ligands across polarized epithelial cells in the kidney, thyroid and across capillary endothelial cells in the brain. LRP therefore comprises a pool of compositionally and functionally related receptors expressed at different levels in different tissues. In some embodiments, this invention uses RAP, which binds and thereby targets members of this pool of related receptors (and particularly cells, tissues, and organs expressing a member of this pool). Examples include the VLDLR on muscle tissue, LRP1B on neuronal tissue, Megalin on both kidney and neuronal tissue and LRP1 on vascular smooth muscle tissue.

IV. RAP AND OTHER MEGALIN LIGANDS

In specific embodiments of the present invention chimeric molecules are made, which comprise first portion that is a megalin ligand or a megalin binding fragment thereof and a second portion that is an active agent whose delivery will be mediated through the binding of the megalin ligand (or fragment thereof) to megalin. In preferred embodiments, the ligand selected to form part of these chimeric molecules will be one which is transcytosed in vivo. "RAP" is a well-known protein of about 39 kDa and 323 amino acids and is a specialized chaperone for members of the LRP family. It is transcytosed in vivo. RAP inhibits the binding of ligand to members of the LDL-receptor family such as LRP (see Bu and Rennke, J. Biol. Chem. 271: 22218-2224 (1996); Willnow et al., J. Biol. Chem. 267: 26172-26180 (1992); Bu and Schwartz, Trends Cell Biol. 8: 272-276 (1998); and Herz and Strickland, J. Clin. Invest. 108: 779-784 (2001). See also, Bu and Schwartz, Trends Cell Biol. 8: 272-276 (1998). Further characterization of RAP, including the complete amino acid sequence of human RAP (FIG. 15), is found in U.S. Pat. No. 5,474,766 which is incorporated herein by reference in its entirety and also with particularity with respect to the RAP amino acid sequences and fragments disclosed therein. The 28 kDa human C-terminal fragment (FIG. 16) is an extremely active RAP polypeptide and in preferred embodiments of the invention, the conjugate comprises this fragment as the carrier for the active agent.

RAP polypeptides include, but are not limited to, RAP, soluble forms of RAP, cleaved RAP, RAP polypeptide fragments, homologues and analogs of RAP, and the like. RAP polypeptides that are functional equivalents of RAP with respect to modulation of LRP receptor binding, transcytosis, or endocytosis can be readily identified by screening for the ability of the RAP polypeptide to bind to LRP. In preferred embodiments, the RAP polypeptide is a homologue of RAP having, for instance, greater than 80%, 90% 95%, 98%, or 99% sequence identity with a naturally occurring, native or wild type mammalian RAP amino acid sequence of similar length or over a domain of at least 10 amino acids, 25 amino acids, 50 amino acids, 100 amino acids, or 200 amino acids, 300 amino acids, or the entire length of the RAP polypeptide.

RAP polypeptides include allelic variants of RAP, paralogs and orthologs in human, mouse, rat, chicken, zebrafish, pig, fruit fly, mosquito, and flatworm native RAP, and derivatives, portions, or fragments thereof (Genbank accession numbers: P30533 (human), XP132029 (mouse), Q99068 (rat), CAA05085 (chicken), AAH49517 (zebrafish), AAM90301 (pig), NP649950 (fruit fly), XP313261 (mosquito), NP506187 (flatworm). A multiple alignment of amino acid sequences from mouse, rat, chicken zebrafish, fruitfly, mosquito, and flatworm and the consensus sequence is shown in FIG. 14.

The RAP polypeptide can be in the form of acidic or basic salts, or in its neutral form. In addition, individual amino acid residues can be modified, such as by oxidation or reduction. Moreover, various substitutions, deletions, or additions can be made to the amino acid or nucleic acid sequences, the net effect of which is to retain or improve upon the desired biological activity of RAP. Further characterization of RAP, including the complete amino acid sequence of RAP, is found in U.S. Pat. No. 5,474,766 which is incorporated herein by reference in its entirety and also with particularity with respect to the amino acid sequences of the various RAP polypeptides disclosed therein. Due to code degeneracy, for example, one of ordinary skill in the art would know of considerable variations of the nucleotide sequences encoding the same amino acid sequence.

Preferred RAP polypeptides share substantial homology with the native amino acid sequence of a receptor associated protein (RAP), particularly the native human sequence (SEQ ID NO:1). In preferred embodiments, the RAP polypeptide is a homologue of RAP having, for instance, greater than 80%, 90% 95%, 98%, or 99% sequence identity with a native or wild type mammalian RAP amino acid sequence of similar length or over a domain or comparison window of at least 10, amino acids, 25 amino acids, 50 amino acids, 100 amino acids, or 200 amino acids, or 300 amino acids or more.

An especially preferred human or mammalian RAP is isolated RAP or a fragment thereof, such as a soluble polypeptide fragment of RAP, which contains at least one of the RAP binding sites for LRP. Substantial guidance exists in the art to which portions of RAP are important to its LRP binding and modulatory activity and which portions may be mutated, altered, or deleted without loss of binding activity (see, Nielsen et al. Proc. Nat. Acad. Sci. USA 94:7521 (1997); and Rall et al. J. Biol. Chem. 273(37):24152, 1998). For instance, RAP's LRP binding function has been mapped by performing direct binding studies on fusion proteins representing overlapping domains of RAP (see Willnow et al., J. Biol. Chem. 267(36):26172-80, 1992). The RAP binding motifs have also been characterized by use of truncated and site-directed RAP mutants (see Melman et al. J. Biol. Chem. 276(31):29338-29346, 2001). Particular RAP polypeptide fragments, suitable for use according to the invention, include fragments (defined from RAP N terminus amino acid to RAP C-terminus amino acid position) 1-323 (RAP); 1-319; 1-250; 1-110; 91-210; 191-323; 221-323; 1-190; 1-200; and 1-210. Preferred RAP polypeptides include fragments 1-323 (RAP); 1-319; 191-323; and 1-210. A modified RAP polypeptide having the C-terminal four amino acid sequence substituted by the sequence KDEL is also suitable. A modified RAP polypeptide in which the C-terminal-four amino acid sequence (HNEL) is deleted is also suitable. Also preferred are RAP polypeptides fragments that comprise the native sequence of RAP from amino acid 201 to 210.

Other preferred embodiments, comprise a human or mammalian RAP polypeptide in which the polypeptide comprises the native amino acid sequence of RAP over positions 282-289, 201-210, and 311-319. Mutated and N-terminus or C-terminus truncated variants of RAP which bind to the LRP receptor are disclosed in Melman et al. (J. Biol. Chem. 276 (31): 29338-46, 2001) which is incorporated herein by reference in its entirety and with particularity to these RAP mutated and truncated variants. Other preferred RAP polypeptides comprise a native sequence of RAP between amino acids 85-148 and 178-248. (see Farquhar et al., Proc. Nat. Acad. Sci. USA 91:3161-3162 (1994).

Thus, many references disclose the binding sites and structure activity relationships for binding of RAP and RAP fragments to the LRP receptor. The skilled artisan can readily adapt a variety of well known techniques in the art in order to obtain RAP polypeptides that contain a LRP binding site and are suitable for use as RAP polypeptides according to the invention. The preferred fragments of RAP are soluble under physiological conditions. The N-terminus or C-terminus of these polypeptides can be shortened as desired, provided that the binding capacity for the LRP particle remains intact. The preferred amino acid sequence of RAP corresponds to the human protein. Suitable sequences for a RAP polypeptide can also be derived from the amino acid sequences of RAP isolated from other mammals or members of the kingdom Animalia.

In order to generate fragments of RAP which contains the LRP binding site, isolated native protein may be converted by enzymatic and/or chemical cleavage to generate fragments of the whole protein, for example by reacting RAP with an enzyme such as papain or trypsin or a chemical such as cyanogen bromide. Proteolytically active enzymes or chemicals are preferably selected in order to release the extracellular receptor region. Fragments that contain the LRP binding site, especially fragments that are soluble under physiological conditions, can then be isolated using known methods.

Alternatively, RAP or a fragment of RAP may be expressed in a recombinant bacteria, as described, for example, in Williams et al., J. Biol. Chem. 267:9035-9040 (1992); Wurshawsky et al., J. Biol. Chem. 269:3325-3330 (1994); Melman et al. J. Biol. Chem. 276(31): 29338-46 (2001).

RAP can be in the form of acidic or basic salts, or in neutral forms. In addition, individual amino acid residues can be modified, such as by oxidation or reduction. Moreover, various substitutions, deletions, or additions can be made to the amino acid or nucleic acid sequences, the net effect of which is to retain or improve upon the desired biological activity of RAP. Due to code degeneracy, for example, there may be considerable variation in nucleotide sequences encoding the same amino acid sequence.

A RAP fragment as used herein includes, but not limited to, any portion of RAP or its biologically equivalent analogs that contains a sufficient portion of the ligand to enable it to bind to LRP and to be transcytosed, transported across the blood-brain barrier; or that otherwise retains or improves upon the desired LRP mediated carrier activities of the ligand. FIG. 15 shows the amino acid sequence of human RAP. FIG. 16 shows the amino acid sequence of the 28 kd RAP polypeptide.

In addition to RAP, other megalin ligands may be used to facilitate the transport of active agents through transcytosis. Megalin ligands other than RAP include, for example, include thyroglobulin (Zheng et al., Endocrinol., 139:1462-1465, 1998; for exemplary sequence see e.g., GenBank Acc. No. NP_003226 and Collins et al., J. Clin. Endocrinol. Metab. 88 (10), 5039-5042, 2003), lipoprotein lipase (Kounnas et al., J. Biol. Chem., 268:14176-14181, 1993; for exemplary sequence see e.g., GenBank Acc. No. AAP35372) lactoferrin (Willnow et al., J. Biol. Chem., 267: 26172-26180, 1992; for exemplary sequence see e.g., GenBank Acc. No.

AAN11304 from Velliyagounder et al., Infect. Immun. 71 (11), 6141-6147, 2003), apolipoprotein J/clusterin (Kounnas et al., J. Biol. Chem., 270:13070-13075, 1995; for exemplary sequence see e.g., GenBank Acc. No. NP_001822 and NP_976084 and Ota et al., Nat. Genet., Nat. Genet. 36 (1), 40-45 (2004); Ota et al., Int. J. Cancer 108 (1), 23-30, 2004), apolipoprotein B (Stefansson et al., J. Biol. Chem., 270: 19417-19421, 1995; for exemplary sequence see e.g., GenBank Acc. No. AAP72970), apolipoprotein E (Willnow et al., J. Biol. Chem., 267: 26172-26180, 1992; for exemplary sequence see e.g., GenBank Acc. No. NP_000032 and Hirono et al., J Neuropsychiatry Clin Neurosci 15 (3), 354-358, 2003), tissue type plasminogen activator (Willnow et al., J. Biol. Chem., 267: 26172-26180, 1992; for exemplary sequence see e.g., GenBank Acc. No. P00750 and Pennica et al., Nature 301 (5897), 214-221 (1983), uPA (Moestrup et al., J. Clin. Invest., 102:902-909, 1998; for exemplary sequence see e.g., GenBank Acc. No. NP_002649 and Tran et al., Mol. Cell. Biol. 23 (20), 7177-7188 (2003), PAI-1 (Stefansson et al., J. Cell. Sci., 108:2361-2368, 1995; for exemplary sequence see e.g., GenBank Acc. No. NP_000593 and He et al., Biochem. Biophys. Res. Commun. 310 (3), 878-883, 2003), vitamin D-binding protein (DBP; Nykjaer et al., Cell 96:507-515, 1999; for exemplary sequence see e.g., GenBank Acc. No. AAA19662 and also, Yang et al., Gene 54 (2-3), 285-290, 1987), vitamin A/retinol-binding protein (RBP; Christensen et al., J. Am. Soc. Nephrol., 10:685-695, 1999; for exemplary sequence see e.g., GenBank Acc. No. AAA59188), β2-microglobin (Orlando et al., J. Am. Soc. Nephrol., 9:1759-1766, 1998; AAA51811 and AAH64910), a1-microglobulin (Orlando et al., J. Am. Soc. Nephrol., 9:1759-1766, 1998; AAH41593 and CAA38585), vitamin B12/cobalamin plasma carrier protein, transcobalamin (TC)-B12, PTH, insulin (Orlando et al., J. Am. Soc. Nephrol., 9:1759-1766, 1998), EGF (Orlando et al., J. Am. Soc. Nephrol., 9:1759-1766, 1998), prolactin (Orlando et al., J. Am. Soc. Nephrol., 9:1759-1766, 1998), albumin, apo H (for exemplary sequence see e.g., GenBank Acc. No. see P02749 see also, Gene 108 (2), 293-298, 1991), transthyretin (for exemplary sequence see e.g., GenBank Acc. No. see NP_000362), lysozyme (Orlando et al., J. Am. Soc. Nephrol., 9:1759-1766, 1998; see e.g., CAA00878 and EP 0222366-A), cytochrome-c (Orlando et al., J. Am. Soc. Nephrol., 9:1759-1766, 1998), α-amylase, and Ca2+, and aprotinin. For a detailed review of the structure, function and expression patterns of megalin those skilled in the art are referred to Christensen and Birn (Am. J. Physiol. Renal. Physiol., 280:F562-573, 2001.) It should be noted that the GenBank Acc. No. provide exemplary sequences of these proteins known to those of skill in the art. There are numerous other such sequences that also are know to those of skill that may be used in the conjugates herein either as the wild-type sequences or as modified sequences (e.g., fragments, conservative variants and the like).

Any of the above megalin ligands will be used for the delivery of active agents via transcytosis. In such embodiment, the megalin ligand is conjugated to the active agent of interest using techniques known to those of skill in the art. In preferred embodiments, it is contemplated that such ligands may be further modified to increase their binding affinity to megalin. Such modified ligands will be particularly useful delivery vehicles for transcytosis across any cell which expresses a megalin receptor. In other preferred embodiments, it is contemplated that the megalin ligands may be modified such that the ligands have a greater binding affinity for megalin than for LRP1. Such ligands will be particularly useful as vectors for the transport of proteins and small molecules across the blood-to-brain barrier. This advantage accrues from avoiding LRP1-mediated clearance of the active agents in the in the liver mediated through the LRP1 receptor on liver cells, thereby increasing serum residence time and, consequently, brain influx of the active agent.

V. CONJUGATES OF MEGALIN-BINDING MOIETY AND ACTIVE AGENT

Throughout the specification, Applicants refer to a megalin-binding moiety. Typically, such a moiety is a natural megalin binding ligand such as the ligands described herein above. In other embodiments, the moiety is a modified such ligand. In still further embodiments, the megalin-binding moiety may be all or part of an antibody that is immunoreactive with megalin and therefore recognizes megalin. In the present invention, the megalin-binding moiety is conjugated to an agent that is to be delivered to a given target, e.g., to the brain. The instant specification refers to megalin ligand-active agent conjugate. It should be understood that the megalin ligand may include any of the aforementioned megalin-binding entities.

A "megalin ligand-conjugate", "ligand-polypeptide conjugate" "chimeric molecule comprising a megalin ligand conjugated to an active agent" each refers to a compound comprising a ligand of megalin, or a megalin-binding fragment thereof, attached to an active agent. As used herein, the term "conjugated" means that the therapeutic agent(s) and megalin polypeptide are physically linked by, for example, by covalent chemical bonds, physical forces such van der Waals or hydrophobic interactions, encapsulation, embedding, or combinations thereof. In preferred embodiments, the therapeutic agent(s) and the megalin ligand polypeptide are physically linked by covalent chemical bonds. As such, preferred chemotherapeutic agents contain a functional group such as an alcohol, acid, carbonyl, thiol or amine group to be used in the conjugation to megalin ligand or fragment thereof. In preferred embodiments, the megalin ligand is RAP or a RAP polypeptide. Adriamycin is in the amine class and there is also the possibility to link through the carbonyl as well. Paclitaxel is in the alcohol class. Chemotherapeutic agents without suitable conjugation groups may be further modified to add such a group. All these compounds are contemplated in this invention. In the case of multiple therapeutic agents, a combination of various conjugations can be used.

In some embodiments, a covalent chemical bond that may be either direct (no intervening atoms) or indirect (through a linker e.g., a chain of covalently linked atoms) joins the megalin ligand and the active agent. In preferred embodiments, the megalin ligand and the active agent moiety of the conjugate are directly linked by covalent bonds between an atom of the megalin ligand and an atom of the active agent. In some preferred embodiments, the megalin binding moiety is connected to the active agent moiety of the compound according to the invention by a linker that comprises a covalent bond or a peptide of virtually any amino acid sequence or any molecule or atoms capable of connecting the megalin ligand or megalin binding fragment thereof to the active agent.

In some embodiments, the linker comprises a chain of atoms from 1 to about 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms are selected from the group consisting of C, O, N, and S. Chain atoms and linkers may be selected according to their expected solubility (hydrophilicity) so as to provide a more soluble conjugate. In some embodiments, the linker provides a functional group that is subject to enzymatic attack in a lysosome. In some embodiments, the linker provides a functional group which is subject to attack by an enzyme found in the target tissue or organ and which upon attack or hydrolysis severs the link between the active agent and the megalin ligand. In some embodiments, the linker provides a functional group that is subject to hydrolysis under the conditions found at the target site (e.g., low pH of a lysosome). A linker may contain one or more such functional groups. In some embodiments, the length of the linker is long enough to reduce the potential for steric hindrance (when an active agent is large) between one or both of the megalin ligand binding site and the active agent active binding site.

If the linker is a covalent bond or a peptide and the active agent is a polypeptide, then the entire conjugate can be a fusion protein. Such fusion proteins may be produced by recombinant genetic engineering methods known to one of ordinary skill in the art. In some embodiments, the megalin ligand portion of the conjugate is formulated to rapidly degrade to release the active compound. In other embodiments, the linker is subject to cleavage under intracellular, or more preferably, lysosomal environmental conditions to release or separate the active agent portion from the megalin ligand polypeptide portion.

The conjugate can comprise one or more active agents linked to the same megalin ligand. For example, conjugation reactions may conjugate from 1 to 5, about 5, about 1 to 10, about 5 to 10, about 10 to 20, about 20 to 30, or 30 or more molecules of an active agent to the megalin ligand polypeptide. These formulations can be employed as mixtures, or they may be purified into specific stoichiometric formulations. Those skilled in the art are able to determine which format and which stoichiometric ratio is preferred. Further, more than one type of active agent may be linked to the megalin ligand polypeptide where delivery of more than one type of an agent to a target site or compartment is desired. A plurality of active agent species may be attached to the same megalin ligand polypeptide e.g., adriamycin-cisplatinum RAP polypeptide (or other megalin ligand) conjugates. Thus, the conjugates may consist of a range of stoichiometric ratios and incorporate more than one type of active agent. These, too, may be separated into purified mixtures or they may be employed in aggregate.

The megalin ligand or fragment thereof conjugate according to the invention may be modified as desired to enhance its stability or pharmacokinetic properties (e.g., PEGylation). Suitable linkers and their functional groups for conjugating megalin ligand polypeptides and an active agent, and the synthetic chemical methods readily adaptable for preparing such, are described in U.S. Patent Application No. 60/395, 762 which is assigned to the same assignee as the present application and herein incorporated by reference in its entirety.

The synthesis of these conjugates is efficient and convenient, producing high yields and drugs with enhanced aqueous solubility.

VI. ACTIVE AGENTS

Active agents according to the invention include agents that can affect a biological process. Particularly preferred active agents for use in the compounds compositions and methods of the invention are therapeutic agents, including drugs and diagnostic agents. The term "drug" or "therapeutic agent" refers to an active agent that has a pharmacological activity or benefits health when administered in a therapeutically effective amount. Particularly preferred agents are naturally occurring biological agents (e.g., enzymes, proteins, polynucleotides, antibodies, polypeptides). In some embodiments, the active agent conjugated to a megalin ligand or a megalin-binding fragment thereof (e.g., in certain preferred embodiments, a RAP or RAP polypeptide) is a molecule, as well as any binding portion or fragment thereof, that is capable of modulating a biological process in a living host. Examples of drugs or therapeutic agents include substances that are used in the prevention, diagnosis, alleviation, treatment or cure of a disease or condition. It is particularly contemplated that the agent is not an agent that causes a disease. Specifically, the agent is not amyloid β protein.

A. Protein Active Agents

The active agent can be a non-protein or a protein. The active agent can be a protein or enzyme or any fragment of such that still retains some, substantially all, or all of the therapeutic or biological activity of the protein or enzyme. In some embodiments, the protein or enzyme is one that, if not expressed or produced or if substantially reduced in expression or production, would give rise to a disease, including but not limited to, lysosomal storage diseases. Preferably, the protein or enzyme is derived or obtained from a human or mouse.

In preferred embodiments of the invention, when the active agent conjugated to RAP or RAP polypeptide is a protein or enzyme, or fragment thereof possessing a biological activity of the protein or enzyme, the active agent has an amino acid sequence identical to the amino acid sequence to the corresponding portion of the human or mammalian protein or enzyme. In other embodiments, the active agent moiety of the conjugate is a protein or enzyme native to the species of the human or mammal. In other embodiments, the protein or enzyme, or fragment thereof, is substantially homologous (i.e., at least 80%, 85%, 90%, 95%, more preferably 98%, or most preferably 99% identical in amino acid sequence over a length of at least 10, 25, 50, 100, 150, or 200 amino acids, or the entire length of the active agent) to a native sequence of the corresponding human or mammal protein or enzyme.

If the compound is a protein, the compound can be an enzyme, or any fragment of an enzyme that still retains some, substantially all, or all of the activity of the enzyme. Preferably, in the treatment of lysosomal storage diseases, the enzyme is an enzyme that is found in a cell that if not expressed or produced or is substantially reduced in expression or production would give rise to a lysosomal storage disease. Preferably, the enzyme is derived or obtained from a human or mouse. Preferably, the enzyme is a lysosomal storage enzyme, such as α-L-iduronidase, iduronate-2-sulfatase, heparan N-sulfatase, α-N-acetylglucosaminidase, arylsulfatase A, galactosylceramidase, acid-alpha-glucosidase, tripeptidyl peptidase, hexosaminidase alpha, acid sphingomyelinase, β-galactosidase, or any other lysosomal storage enzyme.

In some embodiments, therefore, in the treatment of human Lysosomal Storage Diseases (LSDs), the megalin ligand-active agent conjugate comprises an active agent protein or enzyme that is deficient in the lysosomes of a subject or patient to be treated. Such enzymes, include for example, alpha-L-iduronidase, iduronate-2-sulfatase, heparan N-sulfatase, alpha-N-acetylglucosaminidase, Arylsulfatase A, Galactosylceramidase, acid-alpha-glucosidase, thioesterase, hexosaminidase A, Acid Spingomyelinase, alpha-galactosidase, or any other lysosomal storage enzyme. A table of lysosomal storage diseases and the proteins deficient therein, which are useful as active agents, follows:

| Lysosomal Storage Disease | Protein deficiency |
|---|---|
| Mucopolysaccharidosis type I | L-Iduronidase |
| Mucopolysaccharidosis type II Hunter syndrome | Iduronate-2-sulfatase |
| Mucopolysaccharidosis type IIIA Sanfilippo syndrome | Heparan-N-sulfatase |
| Mucopolysaccharidosis type IIIB Sanfilippo syndrome | α-N-Acetylglucosaminidase |
| Mucopolysaccharidosis type IIIC Sanfilippo syndrome | AcetylCoA:N-acetyltransferase |
| Mucopolysaccharidosis type IIID Sanfilippo syndrome | N-Acetylglucosamine 6-sulfatase |
| Mucopolysaccharidosis type IVA Morquio syndrome | Galactose 6-sulfatase |
| Mucopolysaccharidosis type IVB Morquio syndrome | β-Galactosidase |
| Mucopolysaccharidosis type VI | N-Acetylgalactosamine 4-sulfatase |
| Mucopolysaccharidosis type VII Sly syndrome | β-Glucuronidase |
| Mucopolysaccharidosis type IX | hyaluronoglucosaminidase |
| Aspartylglucosaminuria | Aspartylglucosaminidase |
| Cholesterol ester storage disease/ Wolman disease | Acid lipase |
| Cystinosis | Cystine transporter |
| Danon disease | Lamp-2 |
| Fabry disease | α-Galactosidase A |
| Farber Lipogranulomatosis/Farber disease | Acid ceramidase |
| Fucosidosis | α-L-Fucosidase |
| Galactosialidosis types I/II | Protective protein |
| Gaucher disease types I/II/III Gaucher disease | Glucocerebrosidase (β-glucosidase) |
| Globoid cell leukodystrophy/Krabbe disease | Galactocerebrosidase |
| Glycogen storage disease II/Pompe disease | α-Glucosidase |
| GM1-Gangliosidosis types I/II/III | β-Galactosidase |
| GM2-Gangliosidosis type I/Tay Sachs disease | β-Hexosaminidase A |
| GM2-Gangliosidosis type II Sandhoff disease | β-Hexosaminidase A |
| GM2-Gangliosidosis | GM2-activator deficiency |
| α-Mannosidosis types I/II | α-D-Mannosidase |
| β-Mannosidosis | β-D-Mannosidase |
| Metachromatic leukodystrophy | Arylsulfatase A |
| Metachromatic leukodystrophy | Saposin B |
| Mucolipidosis type I/Sialidosis types I/II | Neuraminidase |
| Mucolipidosis types II/III I-cell disease | Phosphotransferase |
| Mucolipidosis type IIIC pseudo-Hurler polydystrophy | Phosphotransferase γ-subunit |
| Multiple sulfatase deficiency | Multiple sulfatases |
| Neuronal Ceroid Lipofuscinosis, CLN1 Batten disease | Palmitoyl protein thioesterase |
| Neuronal Ceroid Lipofuscinosis, CLN2 Batten disease | Tripeptidyl peptidase I |
| Niemann-Pick disease types A/B Niemann-Pick disease | Acid sphingomyelinase |
| Niemann-Pick disease type C1 Niemann-Pick disease | Cholesterol trafficking |
| Niemann-Pick disease type C2 Niemann-Pick disease | Cholesterol trafficking |
| Pycnodysostosis | Cathepsin K |
| Schindler disease types I/II Schindler disease | α-Galactosidase B |
| Sialic acid storage disease | sialic acid transporter |

Thus, the lysosomal storage diseases that can be treated or prevented using the methods of the present invention include, but are not limited to, Mucopolysaccharidosis I (MPS I), MPS II, MPS IIIA, MPS IIIB, Metachromatic Leukodystrophy (MLD), Krabbe, Pompe, Ceroid Lipofuscinosis, Tay-Sachs, Niemann-Pick A and B, and other lysosomal diseases.

Thus, per the above table, for each disease the conjugated agent would preferably comprise a specific active agent enzyme deficient in the disease. For instance, for methods involving MPS I, the preferred compound or enzyme is α-L-iduronidase. For methods involving MPS II, the preferred compound or enzyme is iduronate-2-sulfatase. For methods involving MPS IIIA, the preferred compound or enzyme is heparan N-sulfatase. For methods involving MPS IIIB, the preferred compound or enzyme is α-N-acetylglucosaminidase. For methods involving Metachromatic Leukodystropy (MLD), the preferred compound or enzyme is arylsulfatase A. For methods involving Krabbe, the preferred compound or enzyme is galactosylceramidase. For methods involving Pompe, the preferred compound or enzyme is acid α-glucosidase. For methods involving CLN, the preferred compound or enzyme is tripeptidyl peptidase. For methods involving Tay-Sachs, the preferred compound or enzyme is hexosaminidase alpha. For methods involving Niemann-Pick A and B the preferred compound or enzyme is acid sphingomyelinase.

The megalin ligand-active agent conjugate can comprise one or more active agent moieties (e.g., 1 to 10 or 1 to 4 or 2 to 3 moieties) linked to the megalin ligand or megalin-binding fragment thereof. For example, conjugation reactions may conjugate from 1 to 4 or more molecules of alpha-L-iduronidase to a single megalin ligand, such as a RAP polypeptide molecule. These formulations can be employed as mixtures, or they may be purified into specific megalin ligand polypeptide-agent stoichiometric formulations. Those skilled in the art are able to determine which format and which stoichiometric ratio is preferred. Further, one or more different active agents may be linked to any given molecule of a megalin ligand or a megalin-binding fragment of a megalin ligand to facilitate a more complete degradation of the stored substrates. These megalin ligand conjugated agents may consist of a range of stoichiometric ratios. These, too, may be separated into purified mixtures or they may be employed in aggregate. It may be the order of megalin-binding moiety and the LSD in the fusion is important for the ability of megalin binding moiety to bind to megalin. Therefore, in preferred embodiments, the megalin-binding moiety is located N-terminally to the LSD enzyme coding sequence. In specific embodiments, it is contemplated that the conjugates of the invention comprise a RAP encoding sequence located N-terminally to the LSD enzyme coding sequence.

The megalin ligand conjugated active agents can enter or be transported into or end up residing in the lysosomes of a cell within or without the CNS. The rate of passage of the conjugated agent can be modulated by any compound or protein that can modulate megalin binding activity. In preferred embodiments, the megalin binding affinity of the conjugate is higher than the LRP1 binding affinity. The cell can be from any tissue or organ system affected by the lysosomal storage disease. The cell can be, for instance, an endothelial, epithelial, muscle, heart, bone, lung, fat, kidney, or liver cell. In some embodiments, the cell is preferably a cell found within the BBB. In some embodiments, the cell is a neuron or a brain cell. In other embodiments, the cell is a cell of the periphery or one that is not isolated from the general circulation by an endothelium such as that of the BBB.

B. Drug Active Agents

Generally, the drug active agent may be of any size. Preferred drugs are small organic molecules that are capable of binding to the target of interest. A drug moiety of the conjugate, when a small molecule, generally has a molecular weight of at least about 50 D, usually at least about 100 D, where the molecular weight may be as high as 500 D or higher, but will usually not exceed about 2000 D.

The drug moiety is capable of interacting with a target in the host into which the conjugate is administered during practice of the subject methods. The target may be a number of different types of naturally occurring structures, where targets of interest include both intracellular and extracellular targets, where such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like.

In some embodiments, the active agent or drug has a hydroxyl or an amino group for reacting with the isocyanate reagent or the active agent is chemically modified to introduce a hydroxyl or an amino group for reacting with the isocyanate reagent.

In some embodiments, the active agent or drug comprises a region that may be modified and/or participate in covalent linkage, preferably, without loss of the desired biological activity of the active agent. The drug moieties often comprise cyclical carbon or heterocyclic structures and/or aromatic or polyaromatic structures substituted with one or more of the above functional groups. Also of interest as drug moieties are structures found among biomolecules, proteins, enzymes, polysaccharides, and polynucleic acids, including peptides, saccharides, fatty acids, steroids, purines, pyrimidines, derivatives, structural analogs or combinations thereof.

Suitable active agents include, but are not limited to, psychopharmacological agents, such as (1) central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g., central antitussives (opium alkaloids and their derivatives); pharmacodynamic agents, such as (1) peripheral nervous system drugs, e.g., local anesthetics (ester derivatives, amide derivatives), (2) drugs acting at synaptic or neuroeffector junctional sites, e.g., cholinergic agents, cholinergic blocking agents, neuromuscular blocking agents, adrenergic agents, antiadrenergic agents, (3) smooth muscle active drugs, e.g., spasmolytics (anticholinergics, musculotropic spasmolytics), vasodilators, smooth muscle stimulants, (4) histamines and antihistamines, e.g., histamine and derivative thereof (betazole), antihistamines (H1-antagonists, H2-antagonists), histamine metabolism drugs, (5) cardiovascular drugs, e.g., cardiotonics (plant extracts, butenolides, pentadienolids, alkaloids from erythrophleum species, ionophores, adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g., antianemia drugs, blood coagulation drugs (hemostatics, anticoagulants, antithrombotics, thrombolytics, blood proteins and their fractions), (7) gastrointestinal tract drugs, e.g., digestants (stomachics, choleretics), antiulcer drugs, antidiarrheal agents, (8) locally acting drugs; chemotherapeutic agents, such as (1) anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e., antineoplastic agents or cytotoxic drugs, such as alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g., Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like. Preferred chemotherapeutic agents are those, which in the free form, demonstrate unacceptable systemic toxicity at desired doses. The general systemic toxicity associated with therapeutic levels of such agents may be reduced by their linkage to RAP or a RAP polypeptide or other megalin ligand. Particularly preferred are cardiotoxic compounds that are useful therapeutics but are dose limited by cardiotoxicity. A classic example is adriamycin (also known as doxorubicin) and its analogs, such as daunorubicin. Linking RAP or a RAP polypeptide or another megalin ligand or a megalin-binding fragment of such a ligand to such drugs may prevent accumulation of the active agent at the heart and associated cardiotoxicity.

Suitable active agents include, but are not limited to: Antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; beta-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g., apicycline, chlortetracycline, clomocycline, etc.; synthetic antibacterial agents, such as 2,4-diaminopyrimidines, nitrofurans, quinolones and analogs thereof, sulfonamides, sulfones;

Suitable active agents include, but are not limited to: Antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, etc., thiocarbamates, e.g., tolciclate, triazoles, e.g., fluconazole, itraconazole, terconazole;

Suitable active agents include, but are not limited to: Antihelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

Suitable active agents include, but are not limited to: Antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

Suitable active agents include, but are not limited to: Antiprotozoan agents, such as: acranil, timidazole, ipronidazole, ethylstibamine, pentamidine, acetarsone, aminitrozole, anisomycin, nifuratel, timidazole, benzidazole, suramin, and the like.

Suitable drugs for use as active agents are also listed in: Goodman and Gilman's, The Pharmacological Basis of Therapeutics (9th Ed) (Goodman et al. eds) (McGraw-Hill) (1996); and 1999 Physician's Desk Reference (1998).

Suitable active agents include, but are not limited to: antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,996, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 4,684,747, 4,618,685, 4,611,066, 4,550,187, 4,550,186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psychopharmacological/psychotropic agents, as disclosed in U.S. Pat. Nos. 5,192,799, 5,036,070, 4,778,800, 4,753,951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620, 5,665,752, 5,656,661, 5,635,516, 5,631,283, 5,622,948, 5,618,835, 5,607,959, 5,593,980, 5,593,960, 5,580,888, 5,552,424, 5,552,422, 5,516,764, 5,510,361, 5,508,026, 5,500,417, 5,498,405, 5,494,927, 5,476,876, 5,472,973, 5,470,885, 5,470,842, 5,464,856, 5,464,849, 5,462,952, 5,459,151, 5,451,686, 5,444,043, 5,436,265, 5,432,181, RE034918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 5,006,542, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

immunomodulatory agents, as disclosed in U.S. Pat. Nos. 4,446,128, 4,524,147, 4,720,484, 4,722,899, 4,748,018, 4,877,619, 4,998,931, 5,049,387, 5,118,509, 5,152,980, 5,256,416, 5,468,729, 5,583,139, 5,604,234, 5,612,060, 5,612,350, 5,658,564, 5,672,605, 5,681,571, 5,708,002, 5,723,718, 5,736,143, 5,744,495, 5,753,687, 5,770,201, 5,869,057, 5,891,653, 5,939,455, 5,948,407, 6,006,752, 6,024,957, 6,030,624, 6,037,372, 6,037,373, 6,043,247, 6,060,049, 6,087,096, 6,096,315, 6,099,838, 6,103,235, 6,124,495, 6,153,203, 6,169,087, 6,255,278, 6,262,044, 6,290,950, 6,306,651, 6,322,796, 6,329,153, 6,344,476, 6,352,698, 6,365,163, 6,379,668, 6,391,303, 6,395,767, 6,403,555, 6,410,556, 6,412,492, 6,468,537, 6,489,330, 6,521,232, 6,525,035, 6,525,242, 6,558,663, 6,572,860;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514, 4,147,872, 4,133,819, 4,124,713, 4,117,012, 4,064,272, 4,022,836, 3,966,944;

cholinergic agents, as disclosed in U.S. Pat. Nos. 5,219,872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091,528, 5,091,528, 4,835,157, 5,708,015, 5,594,027, 5,580,892, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874,479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102; the disclosures of all the above of which are herein incorporated by reference.

The drug moiety of the conjugate may be the whole drug or a binding fragment or portion thereof that retains its affinity and specificity for the target of interest while having a linkage site for covalent bonding to the vector protein ligand or linker. The conjugates of such drugs may be used for the same disorders, diseases, and indications as the drugs themselves.

C. Preferred Cancer Chemotherapeutic Active Agents

Preferred cancer chemotherapeutic agents for use in the megalin ligand based conjugates of the invention include all drugs which may be useful for treating brain tumors or other neoplasia in or around the brain, either in the free form, or, if not so useful for such tumors in the free form, then useful when linked to the megalin ligand or megalin binding fragment thereof. Such chemotherapeutic agents are preferably cytotoxic chemotherapeutic agents including but not limited to adriamycin (also known as doxorubicin), cisplatin, paclitaxel, analogs thereof, and other chemotherapeutic agents demonstrate activity against tumours ex vivo and in vivo. Such chemotherapeutic agents also include alkylating agents, antimetabolites, natural products (such as vinca alkaloids, epidophyllotoxins, antibiotics, enzymes and biological response modifiers), topoisomerase inhibitors, microtubule inhibitors, spindle poisons, hormones and antagonists, and miscellaneous agents such as platinum coordination complexes, anthracendiones, substituted ureas, etc. hose of skill in the art will know of other chemotherapeutic agents.

Preferred chemotherapeutic agents are those, which in the free form, demonstrate unacceptable systemic toxicity at desired doses. The general systemic toxicity associated with therapeutic levels of such agents is reduced by their linkage to a megalin ligand or a megalin binding fragment of a megalin ligand. Particularly preferred are cardiotoxic compounds that are useful therapeutics but are dose limited by cardiotoxicity. A classic example is adriamycin (also known as doxorubicin) and its analogs, such as daunorubicin. Linking a megalin ligand or a megalin-binding fragment thereof to such drugs decreases accumulation and associated cardiotoxicity at the heart.

VII. METHODS FOR MAKING CONJUGATES

The present invention generally provides methods and compositions comprising megalin ligands or megalin-binding fragments thereof linked to an active agent.

In general, ligand-active agent conjugates can be prepared using techniques known in the art. There are numerous approaches for the conjugation or chemical crosslinking of compounds to proteins and one skilled in the art can determine which method is appropriate for the active agent to be conjugated. The method employed must be capable of joining the active agent to the megalin ligand or megalin-binding fragment thereof without interfering with the ability of the megalin ligand/fragment to bind to megalin, preferably without altering the desired activity of the compound once delivered. Preferred methods of conjugating the ligand to various compounds are set out in the example section, below. Particularly preferred for linking complex molecules to a megalin ligand, such as RAP, is the SATA/sulfo-SMCC cross-linking reaction (Pierce, Rockford, Ill.). For linking metals to megalin ligand, preferred reactions include, but are not limited to, binding to tyrosine residues through Chloramine T methods, or use of Iodo beads (Pierce) for iodination reactions.

Methods for conjugating the megalin ligand with the representative labels set forth above may be readily accomplished by one of ordinary skill in the art (see, Trichothecene Antibody Conjugate, U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, Methods In Enzymology, Vol. 34, Affinity Techniques, Enzyme Purification: Part B, Jakoby and Wichek (eds.), Academic Press, New York, p. 30, 1974; see also Wilchek and Bayer, "The Avidin-Biotin Complex in Bioanalytical Applications," Anal. Biochem. 171:1-32, 1988; all incorporated herein by reference in their entirety for all purposes).

If the active agent is a protein or a peptide, there are many crosslinkers available in order to conjugate the active agent with the megalin ligand or megalin binding fragment thereof. (See for example, Chemistry of Protein Conjugation and Crosslinking. 1991, Shans Wong, CRC Press, Ann Arbor). The crosslinker is generally chosen based on the reactive functional groups available or inserted on the therapeutic compound. In addition, if there are no reactive groups a photoactivatible crosslinker can be used. In certain instances, it may be desirable to include a spacer between the megalin ligand and the active agent. In one example, megalin ligand and protein therapeutic compounds can be conjugated by the introduction of a sulfhydryl group on the megalin ligand and the introduction of a cross-linker containing a reactive thiol group on to the protein compound through carboxyl groups (see, Wawizynczak and Thorpe, in Immunoconjugates: Antibody Conjugates in Radioimaging and Therapy of Cancer, C. W. Vogel (Ed.) Oxford University Press, 1987, pp. 28-55.; and Blair and Ghose, J. Immunol. Methods 59:129, 1983).

Ligand-chemotherapeutic agents can comprise one or more compound moieties linked to the megalin ligand or megalin-binding fragment thereof. For example, conjugation reactions may conjugate from 1 to 10 or more molecules of adriamycin to a single megalin ligand molecule. Several atoms of gold or iodine can be conjugated to a single megalin ligand or megalin-binding fragment thereof. These formulations can be employed as mixtures, or they may be purified into specific megalin ligand-active compound stoichiometric formulations. Those skilled in the art are able to determine which format and which stoichiometric ratio is preferred. Further, mixtures of active compounds may be linked to the megalin ligand or megalin-binding fragment thereof, such as the RAP adriamycin-cisplatinum composition set out in the examples. These megalin ligand-active agent conjugates may consist of a range of stoichiometric ratios of ligand to an active agent (e.g., RAP:active agent ratios of 1:1 to 1:4; 1:5 to 1:10; or 1:10 to 1:20). Optionally, a plurality of different active agents (e.g. 2, 3, or 4 such agents) may be each conjugated to the megalin ligand or megalin-binding fragment thereof in its own stoichiometric ratio such that megalin ligand or megalin-binding fragment thereof to the total ratio of such additional active agents is not fewer than 1 megalin ligand or megalin-binding fragment thereof per 20 active agents. These, too, may be separated into purified mixtures or they may be employed in aggregate.

The linker is preferably an organic moiety constructed to contain an alkyl, aryl and/or amino acid backbone and which will contain an amide, ether, ester, hydrazone, disulphide linkage or any combination thereof. Linkages containing amino acid, ether and amide bound components will be stable under conditions of physiological pH, normally 7.4 in serum and 4-5 on uptake into cells (endosomes). Preferred linkages are linkages containing esters or hydrazones that are stable at serum pH but hydrolyse to release the drug when exposed to intracellular pH. Disulphide linkages are preferred because they are sensitive to reductive cleavage; amino acid linkers can be designed to be sensitive to cleavage by specific enzymes in the desired target organ. Exemplary linkers are set out in Blattler et al. Biochem. 24:1517-1524, 1985; King et al. Biochem. 25:5774-5779, 1986; Srinivasachar and Nevill, Biochem. 28:2501-2509, 1989.

Drug-Linker intermediates are similar to what has been described above but with either an active ester to react with free amine groups on the megalin ligand or megalin-binding fragment thereof or a maleimide to react with the free thiols that have been created on the megalin ligand or megalin-binding fragment thereof through other groups where persons skilled in the art can attach them to megalin ligand or megalin-binding fragment thereof.

Methods of crosslinking proteins and peptides are well known to those of skill in the art. Several hundred crosslinkers are available for conjugating a compound of interest with a polypeptide such as a megalin ligand or megalin-binding fragment thereof or with a substance which binds such as a ligand (see, e.g., Chemistry of Protein Conjugation and Crosslinking, Shans Wong, CRC Press, Ann Arbor (1991) and U.S. Pat. No. 5,981,194 and PCT Patent Publication Nos. WO 02/13843 and WO 01/59459 which are incorporated herein by reference in their entirety). Many reagents and cross-linkers can be used to prepare conjugates of an active agent and a megalin ligand such as a RAP molecule, for instance, Hermanson et al. Bioconjugate Techniques, Academic Press, (1996). The crosslinker is generally chosen based on the reactive functional groups available or inserted on the therapeutic agent. In addition, if there are no reactive groups, a photoactivatible crosslinker can be used. In certain instances, it may be desirable to include a spacer between megalin ligand and the agent. In one embodiment, megalin ligand and the protein therapeutic agents may be conjugated by the introduction of a sulfhydryl group on megalin ligand and by the introduction of a crosslinker containing a reactive thiol group on to the protein compound through carboxyl groups (Wawizynczak and Thorpe in Immunoconjugates: Antibody Conjugates in Radioimaging and Therapy of Cancer, Vogel (Ed.) Oxford University Press, pp. 28-55 (1987); and Blair and Ghose (1983) J. Immunol. Methods 59:129). In some embodiments, the linker is vulnerable to hydrolysis at the acidic pH of the lysosome so as to free the agent from the and/or linker.

When a linker is used, the linker is preferably an organic moiety constructed to contain an alkyl, aryl and/or amino acid backbone, and containing an amide, ether, ester, hydrazone, disulphide linkage or any combination thereof. Linkages containing amino acid, ether and amide bound components are stable under conditions of physiological pH, normally 7.4 in serum. Preferred linkages are those containing esters or hydrazones that are stable at serum pH, but that hydrolyze to release the drug when exposed to lysosomal pH. Disulphide linkages are preferred because they are sensitive to reductive cleavage. In addition, amino acid linkers may be designed to be sensitive to cleavage by specific enzymes in the desired target organ or more preferably, the lysosome itself. Exemplary linkers are described in Blattler et al. (1985) Biochem. 24:1517-1524; King et al. (1986) Biochem. 25:5774-5779; Srinivasachar and Nevill (1989) Biochem. 28:2501-2509.

In some embodiments, the linker is a polyethylene glycol or polypropylene glycol. In other embodiments, the linker is from 4 to 20 atoms long. In other embodiments, the linker is from 1 to 30 atoms long with carbon chain atoms that may be substituted by heteroatoms independently selected from the group consisting of O, N. or S. In some embodiments, from 1 to 4 or up to one-third of the C atoms are substituted with a heteroatom independently selected from O, N, S. In other embodiments, the linker contains a moiety subject to hydrolysis upon delivery to the lysosomal environment (e.g., susceptible to hydrolysis at the lysosomal pH or upon contact to a lysosomal enzyme). In some embodiments, the linker group is preferably hydrophilic to enhance the solubility of the conjugate in body fluids. In some embodiments, the linker contains or is attached to the megalin ligand molecule or the protein agent by a functional group subject to attack by other lysosomal enzymes (e.g., enzymes not deficient in the target lysosome or a lysosomal enzyme not conjugated to the megalin ligand carrier). In some embodiments, the megalin ligand and agent are joined by a linker comprising amino acids or peptides, lipids, or sugar residues. In some embodiments, the megalin ligand and agent are joined at groups introduced synthetically or by post-translational modifications.

In some embodiments, agent-linker intermediates are similar to what has been described previously, but comprise, for example, either an active ester that can react with free amine groups on megalin ligand or a maleimide that can react with the free thiols created on megalin ligand via a SATA reaction or through other groups to which the active agent may be attached.

A. Methods for Conjugating a Megalin Ligand Polypeptide to a Protein or Enzyme.

One of ordinary skill in the art would know how to conjugate an active agent to a protein or peptide. Methods of conjugating active agents and labels to proteins are well known in the art. See, for instance, U.S. Pat. No. 5,981,194. Many reagents and cross linkers can be used to prepare bioconjugates of an active agent and a biopolymer. See, for instance, Hermanson et al. Bioconjugate Techniques, Academic Press, (1996).

In some embodiments of the present invention, the megalin ligand and the active agent are both polypeptides and the megalin ligand-active agent conjugate is a fusion protein. Fusion proteins may be prepared using standard techniques known in the art. Typically, a DNA molecule encoding the megalin ligand or a portion thereof is linked to a DNA molecule encoding the protein compound. The chimeric DNA construct, along with suitable regulatory elements can be cloned into an expression vector and expressed in a suitable host. The resultant fusion proteins contain megalin ligand or a portion thereof used to the selected protein compound. Megalin ligand-LSD enzyme proteins are particularly contemplated, and exemplary such conjugates include the RAP-human alpha glucosidase and RAP-iduronidase conjugates/fusion proteins described in Example VII and FIGS. 3 and 4. These fusion proteins were prepared using standard techniques known in the art.

The chimeric protein of the present invention can be produced using host cells expressing a single nucleic acid encoding the entire chimeric protein or more than one nucleic acid sequence, each encoding a domain of the chimeric protein and, optionally, an amino acid or amino acids which will serve to link the domains. The chimeric proteins can also be produced by chemical synthesis.

Host Cells

Host cells used to produce chimeric proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types. Host cells can include mutants of CHO cells that do not express LRP such as CHO13-5-1 (FitzGerald et al., J. Biol. Chem., 129(6):1533-41, 1995).

Cells that contain and express DNA or RNA encoding the chimeric protein are referred to herein as genetically modified cells. Mammalian cells that contain and express DNA or RNA encoding the chimeric protein are referred to as genetically modified mammalian cells. Introduction of the DNA or RNA into cells is by a known transfection method, such as electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the DNA or RNA can be introduced by infection with a viral vector. Methods of producing cells, including mammalian cells, which express DNA or RNA encoding a chimeric protein are described in co-pending patent applications U.S. Ser. No. 08/334,797, entitled "In Vivo Protein Production and Delivery System for Gene Therapy", by Richard F Selden, Douglas A. Treco and Michael W. Heartlein (filed Nov. 4, 1994); U.S. Ser. No. 08/334,455, entitled "In Vivo Production and Delivery of Erythropoietin or Insulinotropin for Gene Therapy", by Richard F Selden, Douglas A. Treco and Michael W. Heartlein (filed Nov. 4, 1994) and U.S. Ser. No. 08/231,439, entitled "Targeted Introduction of DNA Into Primary or Secondary Cells and Their Use for Gene Therapy", by Douglas A. Treco, Michael W. Heartlein and Richard F Selden (filed Apr. 20, 1994). The teachings of each of these applications are expressly incorporated herein by reference in their entirety.

Nucleic Acid Constructs

A nucleic acid construct used to express the chimeric protein can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to chimeric protein-encoding sequences, sequences sufficient for expression of the protein in the cells and, optionally, for replication of the construct. It typically includes a promoter, chimeric protein-encoding DNA and a polyadenylation site. The DNA encoding the chimeric protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it need include only the chimeric protein-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

Cell Culture Methods

Mammalian cells containing the chimeric protein-encoding DNA or RNA are cultured under conditions appropriate for growth of the cells and expression of the DNA or RNA. Those cells which express the chimeric protein can be identified, using known methods and methods described herein, and the chimeric protein isolated and purified, using known methods and methods also described herein; either with or without amplification of chimeric protein production. Identification can be carried out, for example, through screening genetically modified mammalian cells displaying a phenotype indicative of the presence of DNA or RNA encoding the chimeric protein, such as PCR screening, screening by Southern blot analysis, or screening for the expression of the chimeric protein. Selection of cells having incorporated chimeric protein-encoding DNA may be accomplished by including a selectable marker in the DNA construct and culturing transfected or infected cells containing a selectable marker gene under conditions appropriate for survival of only those cells that express the selectable marker gene. Further amplification of the introduced DNA construct can be affected by culturing genetically modified mammalian cells under conditions appropriate for amplification (e.g., culturing genetically modified mammalian cells containing an amplifiable marker gene in the presence of a concentration of a drug at which only cells containing multiple copies of the amplifiable marker gene can survive).

Genetically modified mammalian cells expressing the chimeric protein can be identified, as described herein, by detection of the expression product. For example, mammalian cells expressing chimeric protein in which the carrier is a megalin ligand can be identified by a sandwich enzyme immunoassay. The antibodies can be directed toward the megalin-binding portion or the active agent portion of the conjugate.

VIII. LABELS

In some embodiments, the megalin ligand based active agent conjugate is labeled to facilitate its detection. A "label" or a "detectable moiety" is a composition detectable by spectroscopic, photochemical, biochemical, immunochemical, chemical, or other physical means. For example, labels suitable for use in the present invention include, for example, radioactive labels (e.g., 32P), fluorophores (e.g., fluorescein), electron dense reagents, enzymes (e.g., as commonly used in an ELISA), biotin, digoxigenin, or haptens and proteins which can be made detectable, e.g., by incorporating a radiolabel into the hapten or peptide, or used to detect antibodies specifically reactive with the hapten or peptide.

As noted above, depending on the screening assay employed, the active agent, the linker or the megalin ligand polypeptide portion of a conjugate may be labeled. The particular label or detectable group used is not a critical aspect of the invention, as long as it does not significantly interfere with the biological activity of the conjugate. The detectable group can be any material having a detectable physical or chemical property. Thus, a label is any composition detectable by spectroscopic, photochemical, biochemical, immunochemical, electrical, optical or chemical means.

Examples of labels suitable for use in the present invention include, but are not limited to, fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugating an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The conjugates can also be conjugated directly to signal generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands may be used in the diagnosis of a disease or health condition.

The present invention provides a screening assay for megalin ligand polypeptide-active agent conjugates, wherein the conjugates are tested for their ability to influence a measurable activity of the megalin receptor which can be situated in a whole cell, a cell extract, semi-purified, purified or any other format that allows for measurement of its activity. The activity can be any activity in the expression, function or degradation of megalin including, for example, the amount or timing of such activities. Such activities include, for example, transcription, transcript processing, translation or transcript stability of the megalin gene sequence or mRNA transcript. Such activities include, for example, the synthesis of new LRP, the sub-cellular localization of megalin and activation of megalin biological activity. Such activities include, for example, the ability of megalin to bind substances, adopt conformations, catalyze reactions, bind known ligands and the like. Such activities include, for example, the amount or stability of megalin, the processing and removal or degradation of megalin and the like. In preferred embodiments, the megalin ligand used is one which has been modified or naturally has a higher binding affinity for megalin than for any other LRP receptor, and particularly a higher binding affinity for megalin than for LRP1. Screening assays similar to those discussed above for megalin may be set up for any other LRP receptors to yield a comparison of the relative binding affinities of the megalin ligand for megalin as compared to other LRP receptors.

The invention contemplates a variety of different screening formats. Some designs are considered low throughput and test only one or a few compounds in series or in parallel. High throughput screening assays are suitable for screening tens of thousands or hundreds of thousands of compounds in a matter of weeks or months. "In silico" screening formats employ computer-aided rational design techniques to identify potential modulators of megalin biological activity.

A. Modulating Uptake of Megalin Ligand-Conjugated Active Agents by Modulating Megalin Receptor Activity Those skilled in the art will appreciate that increasing megalin ligand-active agent conjugate uptake and delivery to targets including, but not limited to, the brain or lysosomes is useful and desirable in situations such as, but not limited to, where the conjugate is being used to treat a neurological condition and/or a LSD and increased amounts of delivery would provide therapeutic benefit. Those skilled in the art will appreciate that decreasing conjugate uptake and delivery across the blood-brain barrier is useful and desirable for a variety of reasons including, but not limited to, where the conjugate is being used for its potential cardio-protective effect or used in other (non-CNS) organs and side-effects of brain uptake are to be avoided.

Suitable megalin ligands, megalin-binding fragment thereof, active agent conjugates of megalin ligands or megalin-binding fragment thereof, and modulators of megalin and/or other LRP activity and modulators of megalin ligand conjugate delivery can also be readily identified using a modification of the Transwell apparatus set out in EXAMPLE 1 below. In the modified form, a compound (e.g., megalin ligand, a conjugate of a megalin ligand with an active agent or a modulator) is added to the luminal surface of the cells in the Transwell apparatus. The compound is then scored according to how well it is able to traverse across the BBCECs to the abluminal side or as to how well (if a modulator) it increases or decreases the transport of a megalin ligand or a megalin biding fragment of a megalin ligand or another LRP ligand across the BBCECs to the abluminal side. A library of compounds can be readily screened or tested to identify pharmacologically superior modulators.

An exemplary ligand used herein is RAP. Other known ligands of the megalin receptor may be screened for use as modulators of the delivery of the conjugate, or as models for designing such modulators. These ligands include, but are not limited to, ApoE, Chylomicron remnants, β-VLDL, activated α2-macroglobulin, tPA, Tissue factor inhibitor, Pro-uPA, PAI-1, Saposin, Gentamycin, Thyroglobulin, Polymixin B, Seminal Vesicle Secretory Protein A, Thrombospondin-1, Lactoferrin, and β-APP. These ligands may be modified to increase their binding affinity to megalin. Those ligands with a greater binding affinity to megalin as compared to LRP1 are particularly preferred.

IX. METHODS OF USING, PHARMACEUTICAL COMPOSITIONS, AND THEIR ADMINISTRATION

The conjugates and modulators may be administered by a variety of routes. For oral preparations, the conjugates can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The conjugates and modulators can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The conjugates, modulators, and LRP ligands can be utilized in aerosol formulation to be administered via inhalation. The compounds of the present invention can be formulated into pressurized acceptable propellants such as dichlorodifluoromethane, propane, nitrogen and the like.

Furthermore, the conjugates and modulators can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms of the conjugate, modulator, and LRP ligand for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the conjugate in a composition as a solution in sterile water, normal saline or another pharmaceutically acceptable carrier.

In practical use, the conjugate, modulator, and LRP ligand according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

With respect to transdermal routes of administration, methods for transdermal administration of drugs are disclosed in Remington's Pharmaceutical Sciences, 17th Edition, (Gennaro et al. Eds. Mack Publishing Co., 1985). Dermal or skin patches are a preferred means for transdermal delivery of the conjugates, modulators, and LRP ligands of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

In specific embodiments, it is contemplated that the therapeutic administering of the conjugates described herein will be administered intrathecally into the CSF. The intrathecal administration of the present invention may comprise introducing the pharmaceutical composition into a cerebral ventricle. Alternatively, the intrathecal administration may comprise introducing the pharmaceutical composition into the lumbar area. In yet another alternative, the intrathecal administration comprises introducing the pharmaceutical composition into the cisterna magna. Any such administration is preferably via a bolus injection. Depending on the severity of the symptoms and the responsiveness of the subject to the therapy, such a bolus injection may be administered once per week, once per month, once every 6 months or annually. In other embodiments, the intrathecal administration is achieved by use of an infusion pump. The pharmaceutical could of course be intrathecally administered continually over a period of at least several days or alternatively, the intrathecal administration is continually over a period of at least four weeks. Of course, where the administration is via continuous infusion, the rate of dose administration of the enzyme replacement therapy may be greatly reduced as compared to the bolus injection administration. In preferred embodiments, the active agent of the conjugate is iduronidase and it is delivered in an amount that comprises about 1 mg iduronidase/20 kg of body weight of the mammal being treated for MPS. In particular embodiments, the above dose is delivered to 15 cc CSF. At such a concentration it is contemplated that the enzyme concentration will be 18,000 units per ml of CSF. It should be understood that the aforementioned dosage is merely an exemplary dosage and those of skill in the art will understand that this dosage may be varied.

The methods and compositions of the invention may be combined with methods and compositions of inducing antigen specific tolerance prior to the enzyme replacement therapy. Such methods include inducing antigen specific tolerance comprises administration of an immunosuppressive agent, such as e.g., cyclosporine A and may further comprise administration of an antiproliferative agent, including but not limited to a nucleotide analog or an anti-metabolite. The antiproliferative agent may be azathioprine. Further methods are described in e.g., U.S. patent application Ser. No. 10/141,668, published as U.S. Publication No. 20030211113; and U.S. patent application Ser. No. 10/429,314 published as U.S. Publication No. 20040009906, each incorporated herein by reference.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

Those of skill will readily appreciate that dose levels can vary as a function of the specific compound, the severity of the symptoms and the susceptibility of the subject to side effects. Preferred dosages for a given compound are readily determinable by those of skill in the art by a variety of means, including, but not limited to dose response and pharmacokinetic assessments conducted in patients, test animals, and in vitro.

In each of these aspects, the compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The compositions may be conveniently presented in unit dosage form and prepared by any of the methods well-known in the art of pharmacy.

In practical use, the modulators or according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. The percentage of an active compound in these compositions may, of course, be varied and may conveniently be between about 2 percent to about 60 percent of the weight of the unit.

The conjugates, modulators, and ligands of the invention are useful for therapeutic, prophylactic and diagnostic intervention in animals, and in particular in humans. As described herein, the conjugates show preferential accumulation and/or release of the active agent in any target organ, compartment, or site depending upon the biopolymer used.

Compositions of the present invention may be administered encapsulated in or attached to viral envelopes or vesicles, or incorporated into cells. Vesicles are micellular particles which are usually spherical and which are frequently lipidic. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer compounds intracellularly and to deliver compounds to the target organs. Controlled release of a p97-composition of interest may also be achieved using encapsulation (see, e.g., U.S. Pat. No. 5,186,941).

Any route of administration that delivers the megalin ligand-based active agent conjugate or modulator composition into the blood stream, or preferably at least outside of the blood-brain barrier, may be used. Preferably, the composition is administered peripherally, most preferably intravenously or by cardiac catheter. Intrajugular and intracarotid injections are also useful. Compositions may be administered locally or regionally, such as intraperitoneally or subcutaneously on intramuscularly. In one aspect, compositions are administered with a suitable pharmaceutical diluent or carrier.

Dosages to be administered will depend on individual needs, on the desired effect, the active agent used, the biopolymer and on the chosen route of administration. Preferred dosages of a conjugate range from about 0.2 µmol kg to about 25 nmol kg, and particularly preferred dosages range from 2-250 µmol/kg; alternatively, preferred doses of the conjugate may be in the range of 0.02 to 2000 mg/kg. These dosages will be influenced by the number of active agent or drug moieties associated with the biopolymer. Alternatively, dosages may be calculated based on the active agent administered.

In preferred embodiments the conjugate comprises human RAP. For instance, doses of RAP-adriamycin comprising from 0.005 to 100 mg/kg of adriamycin are also useful in vivo. Particularly preferred is a dosage of RAP-adriamycin comprising from 0.05 mg/kg to 20 mg/kg of adriamycin. Those skilled in the art can determine suitable doses for compounds linked to a megalin ligand based in part on the recommended dosage used for the free form of the compound. Conjugation of the active agent to a megalin ligand such as RAP generally reduces the amount of drug needed to obtain the same effect.

The conjugates and modulators of the invention are useful for therapeutic, prophylactic and diagnostic intervention in animals, and in particular in humans. Megalin ligand compounds may show preferential accumulation in particular tissues. Preferred medical indications for diagnostic uses include, for example, any condition associated with a target organ of interest (e.g., lung, liver, kidney, spleen). In particularly preferred embodiments, the target organ of interest in the brain.

The subject methods find use in the treatment of a variety of different disease conditions. In certain embodiments, of particular interest is the use of the subject methods in disease conditions where an active agent or drug having desired activity has been previously identified, but in which the active agent or drug is not adequately delivered to the target site, area or compartment to produce a fully satisfactory therapeutic result. With such active agents or drugs, the subject methods of conjugating the active agent to a megalin ligand or a megalin binding fragment thereof can be used to enhance the therapeutic efficacy and therapeutic index of active agent or drug.

The specific disease conditions treatable by with the subject conjugates are as varied as the types of drug moieties that can be present in the conjugate. Thus, disease conditions include cellular proliferative diseases, such as neoplastic diseases, autoimmune diseases, cardiovascular diseases, hormonal abnormality diseases, degenerative diseases, diseases of aging, diseases of the central nervous system (e.g., Alzheimer's disease, epilepsy, hyperlipidemias), psychiatric diseases and conditions (e.g., schizophrenia, mood disorders such as depression and anxiety), infectious diseases, enzyme deficiency diseases, lysosomal storage diseases such as those described above, and the like.

Treatment is meant to encompass any beneficial outcome to a subject associated with administration of a conjugate including a reduced likelihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

In specific embodiments, the disorder being treated is a lysosomal storage disease and the conjugate is administered as a pharmaceutical composition in an amount effective to decrease the amount of storage granules present in the brain tissue of said mammal. Typically, the symptoms of such a disorder are monitored through routine assessment of history, physical examination, echocardiography, electrocardiography, magnetic resonance imaging, polysomnography, skeletal survey, range of motion measurements, corneal photographs, and skin biopsy. Administration of a megalin-binding moiety conjugated to a therapeutic agent in such a disorder results in normalization of developmental delay and regression in said subject, reduction in high pressure hydrocephalus, reduction in spinal cord compression in said subject, and reduction in number and/or size of perivascular cysts around the brain vessels of said subject. Methods of monitoring and assessing such sequelae are known to those of skill in the art. Those of skill in the art are referred to U.S. Pat. No. 6,585,971; U.S. Pat. No. 6,569,661 and U.S. Pat. No. 6,426,208 and U.S. Patent Publication No. 20040009906 for additional descriptions of such sequelae.

In some aspects, it may be useful to increase the tolerance of the animal to the therapy being delivered. Such methods are described in U.S. patent application Ser. No. 10/429,314 filed May 5, 2003 and published as 20040009906 (incorporated herein by reference in its entirety).

In preferred embodiments, the animal is suffering from mucopolysaccharidosis I and has about 50% or less of a normal α-L-iduronidase activity. In such embodiments, it would be desirable to administered an effective dose of between about 0.001 mg/kg body weight and 0.5 mg/kg body weight of human α-L-iduronidase as part of the conjugate e.g., weekly to a subject suffering from a deficiency thereof. In other embodiments, the subject is given a dose of between about 0.01 mg/15 cc of CSF to about 5.0 mg/15 cc of CSF in the mammal of said human α-L-iduronidase weekly. The therapies contemplated herein promote the breakdown of glycosaminoglycan (GAG) in a brain cell of a subject having lysosomal storage disease. The brain cell may be a neuron, a neuroglial cell, an ependymal cell. Typically, the brain cells in which granule accumulation occurs and should be ameliorated by administering a conjugate of the invention include neurons, glial cells, microglial cells, astrocytes, oligodendroglial cells, perivascular cells, perithelial cells, meningeal cells, ependymal cells, arachnoid granulation cells, arachnoid membranes, dura mater, pia mater and choroid plexus cells. The therapy in preferred embodiments reduces storage granules in meningeal cells as compared to the number of lysosomal storage granules present in a similar cell in the absence of administration of said conjugate. This produces the therapeutic effects of relieving the symptoms of high pressure hydrocephalus in some subjects. and said administering reduces the amount of CSF fluid in the meningeal tissue of said subject.

A variety of hosts or subjects are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

XI. PRODUCTION OF MEGALIN LIGAND POLYPEPTIDES

In the present invention, numerous megalin ligands may be used to facilitate transcytosis of a given active agent. One exemplary such ligand is RAP. RAP and RAP polypeptides for use according to the invention include those disclosed in U.S. Pat. No. 5,474,766 that is enclosed herein by reference in its entirety for the purposes of disclosing such peptides and how they may be obtained for use in the compounds and compositions of the present invention. RAP, and RAP polypeptides, and other megalin ligands may be produced using any of protein preparation and purification methods known to those of skill in the art.

The ligand can be purified from a naturally occurring source of the protein, can be isolated from a recombinant host expressing the ligand, or can be synthesized using well known techniques in protein synthesis. A skilled artisan can readily adapt a variety of such techniques in order to obtain a megalin ligand that contain the megalin binding site. Such a megalin ligand may for example possess the megalin docking/binding site found on RAP. See, for instance, Melman et al., J. Biol. Chem. 276 (31): 29338-29346 (2001); Savonen et al., J Biol. Chem. 274(36): 25877-25882 (1999); Nielsen et al. Proc. Natl. Acad. Sci. USA 94:7521-7525 (1997); Medved et al., J. Biol. Chem. 274(2): 717-727 (1999); Rall et al., J. Biol. Chem. 273(37): 24152-24157 (1998); Orlando et al., Proc. Natl. Acad. Sci. USA 3161-3163 (1994).

The isolation of native RAP proteins has been described in Ashcom et al., J. Cell. Biol. 110:1041-1048 (1990) and Jensen et al., FEBS Lett. 255:275-280 (1989). Megalin ligand fragments containing the megalin binding site may be generated from isolated native protein which is converted by enzymatic and/or chemical cleavage to generate fragments of the whole protein. Exemplary such methods are taught in U.S. Pat. No. 6,447,775 which is herein incorporated by reference with particular reference to such methods for obtaining RAP polypeptides.

In addition, the megalin ligand or a megalin binding fragment of such a ligand can be expressed in a recombinant bacteria, as described, by Williams et al., J. Biol. Chem. 267:9035-9040 (1992) and Wurshawsky et al., J. Biol. Chem. 269:3325-3330 (1994).

As indicated herein throughout, RAP is a preferred megalin ligand. Procedures for purifying the 39 kDa RAP protein from a recombinant *E. coli* strain has been previously described by Herz et al., J. Biol. Chem. 266, 21232-21238 (1991). A modified version of that procedure can be used as described in U.S. Pat. No. 5,474,766 and below.

Cultures of *E. coli* strain DH5alpha carrying the expression plasmid pGEX-39 kDa can be grown to mid-log phase in LB medium with 100 µg/ml ampicillin at 37° C. Cultures can then be cooled to 30° C. and supplemented with 0.01% isopropylthio-beta-D-galactoside to induce expression of the glutathione-S-transferase-39 kDa fusion protein. Following a 4-6 hour induction at 30° C., cultures can be cooled with ice and recovered by centrifugation.

All of the following steps are to be carried out at 4° C. Cell pellets are lysed in PBS with 1% Triton X-100, 1 µM pepstatin, 2.5 µg/ml leupeptin, 0.2 mM phenylmethylsulfonyl fluoride (PMSF), and 1 µM ethylenediaminetetraacetate (EDTA). Sonication of this lysate with a Branson Model 450 Sonifier with separation of the resulting membranes and other cellular debris by centrifugation at 15,000 g for 15 minutes is then followed by retrieval of the supernatant. The supernatant from this step is incubated overnight with agarose immobilized glutathione beads (Sigma Chemical Co.) in PBS and 0.1% sodium azide. The beads can then be washed, and elution of the fusion protein can be carried out by competition with 5 mM reduced glutathione (Sigma Chemical Co.). Following dialysis, the fusion protein can be cleaved by an overnight incubation with 100 ng of activated human thrombin per 50 µg of fusion protein. The glutathione-5-transferase epitope can subsequently be removed by further incubation with agarose immobilized glutathione beads.

The 28 kDa protein fragment of the 39 kDa protein ("28 kDa protein") of the present invention has the following amino acid sequence set forth in the Sequence Listing as SEQ ID NO:2 (FIG. 16).

The 28 kDa protein has a molecular weight of 28,000 daltons on SDS-PAGE, is relatively stabile to acid hydrolysis, is soluble in 1% Triton X-100, and has approximately the same inhibitory activity (Ki) on t-PA binding to the hepatic receptor as the 39 kDa protein. The 28 kDa protein may be cloned and purified as further exemplified in U.S. Pat. No. 5,474,766 which is expressly incorporated herein by reference for such methods of cloning.

While the above method is described for the production and purification of RAP, as indicated above, other megalin ligands and megalin binding fragments also may be produced using similar techniques. A review of such ligands may be found in Christensen and Bim, (Am. J. Physiol. Renal Physiol., 280:F562-F573, 2001, see particularly Table 1 and references cited therein) Techniques for making and purifying such ligands are well known to those of skill in the art.

XI. EXAMPLES

The following example(s) is included to demonstrate preferred embodiments of the invention. It should be appreciated by those of skill in the art that the techniques disclosed in the example(s) that follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following examples provide exemplary protocols for assessing transcytosis in vitro and for characterizing the interaction of megalin ligands such as RAP with megalin and other receptors.

Example 1

Transcytosis of p97

Transcytosis experiments were performed as follows. One insert covered with bovine brain capillary endothelial cells (BBCECs) was set into a Transwell apparatus containing a six-well microplate with 2 ml of Ringer/Hepes and pre-incubated for 2 h at 37° C. $^{125}$I-p97 (250 nM) was added to the upper side of the filter covered with cells. At various times, the insert was transferred to avoid re-endocytosis of p97 by the abluminal side of the BBCECs. At the end of experiment, [$^{125}$I]-p97 was measured after TCA precipitation. Transcytosis is depicted in FIG. 17.

The effect of RAP on transcytosis of $^{125}$I-p97 was assessed. In FIG. 1, RAP, a known polypeptide inhibitor of the LRP family was applied to the cells (25 micrograms/ml). RAP significantly inhibited the transcytosis of p97, thus directly implicating the LRP family in transcytosis.

Example 2

Construction, Expression, Purification and Characterization of RAP Fusions

Expression constructs encoding fusions between the human receptor-associated protein (RAP) and human alpha-glucosidase (GAA), alpha-L-iduronidase (IDU) or glial cell-derived neurotrophic factor (GDNF) were prepared. For this purpose, a sequence that encodes RAP was fused to the 5'-end of sequences that encode the different fusion partners. All sequences were obtained by high-fidelity PCR amplification of human cDNA with the following primers shown in FIG. 2a. The GDNF fusion was designed for expression in bacteria. To this end, primer RAPBACF was substituted for RAPF in the RAP amplification for this construct (FIG. 2b).

The 5'-end of RAP was truncated to remove the signal peptide sequence. Instead, an in-frame BamHI site, which encodes the dipeptide GS, was added for the mammalian expression construct. Sequence encoding the tetrapeptide MGGS with an NcoI site at the 5'-end was added for the bacterial expression construct. The 3'-end of RAP was truncated to remove the tetrapeptide HNEL endoplasmic reticulum retention signal. Instead, the coding sequence for a six amino-acid spacer (AEAETG) was appended. The last two codons of the spacer specify an AgeI restriction site. The 5'-end of GAA was truncated to remove the signal peptide and pro-peptide sequences (Wisselaar, et al., J. Biol. Chem. 268 (3):2223-31, 1993). Instead, an AgeI site was added to permit fusion to the RAP-spacer portion of the fusion. The 5'-end of IDU was similarly truncated to remove the signal peptide and introduce the restriction site. The 5'-end of GDNF was truncated to remove both the signal peptide and pro-peptide sequences (Lin et al., Science, 260(5111): 1130-2, 1993).

The open-reading frames encoding the GAA and IDU fusions were ligated into the expression vector pCINmt using flanking BamHI and XhoI sites. The vector contains the human melanotransferrin signal peptide with an in-frame BamHI site at the 3'-end. The sequences of the resulting fusion proteins are shown in FIGS. 3 and 4. The pCINmt (derived from Invitrogen vector pcDNA3.1) control sequences consist of the human CMV promoter followed by the rabbit IVS2 and the rat preproinsulin RNA leader sequence. A bovine growth hormone terminator sequence is positioned at the 3'-end of the expression cassette. The vector includes a selectable marker composed of an attenuated neomycin phosphotransferase gene driven by the weak HSV-tk promoter (Yenofsky et al., Proc. Nat'l Acad. Sci., USA 87(9): 3435-9, 1990). Expression constructs for RAP-GAA and RAP-IDU were transfected into an Lrp-deficient CHO cell line (CHO13-5-1) and recombinants selected with 800 µg/mL G418.

The RAPGDNF fusion (FIG. 5) was cloned into the bacterial expression vector pBADhisA (Invitrogen) using the flanking NcoI and XbaI sites. The resulting expression vector was transfected into BL21 cells and recombinants selected with carbenicillin. Expressed, purified RAP-GDNF fusion may be assayed for the ability to protect dopaminergic neurons or other activities as previously described (Kilic et al., Stroke 34(5):1304-10, 2003).

Expression of RAP Fusions

Culture medium was JRH 302 supplemented with 2 mM L-glutamine, gentamycin, amphotericin, 800 µg/mL G418 and 2.5% fetal calf serum. Recombinant clones were grown in T225 flasks prior to seeding into 1 L Corning spinner flasks on Cytopore 1 beads (Amersham) in the presence of serum. Spinner flasks were maintained in a tissue culture incubator set at 37° C. and 5% $CO_2$. Medium was replaced every two days with serum-free medium until serum levels were undetectable. Subsequently, harvests were collected every two days and medium exchanged.

Purification of RAP-GAA for Uptake Assay:

RAP-GAA harvested in the medium from the spinner flasks was applied to a Blue-Sepharose column (Amersham) in low-salt buffer at neutral pH. Fusion was eluted with a linear salt gradient, and fractions containing fusion were loaded to a Heparin-Sepharose column (Amersham) and again eluted with a linear salt gradient. Eluted fractions containing activity were pooled and applied to a Phenyl-Sepharose column (Amersham). RAP-GAA was eluted from the Phenyl-Sepharose column with a decreasing salt step gradient. Eluted fractions were run on an SDS-PAGE gel and stained to determine relative percent purity. Based on gel analysis, peak activity fractions were about 70% pure. Fractions were pooled, concentrated using a 30 kD MWCO membrane (Millipore), and exchanged into phosphate-buffered saline at neutral pH.

The activity of the lysosomal enzyme in the fusion was determined to be unaffected by fusion to RAP. Purified human LRP (1 µg, recombinant, binding domain 2) was spotted onto PVDF filters in a 96-well dot-blot apparatus. Purified RAP-lysosomal enzyme fusion (RAP-LE) in Tris-buffered saline pH 7.5 with 5 mM $CaCl_2$ and 3% non-fat dry milk (TBS/Ca/BLOTTO) was overlayed on the immobilized LRP. Conditioned medium containing the RAP-LE, buffer alone and RAP alone were similarly incubated with immobilized LRP. Filters were washed three times to remove unbound protein. Duplicate filters were probed with anti-LE antibody or anti-RAP antibody. Blots were developed with chemiluminescent detection. The activity of the lysosomal enzyme was measured using fluorescent substrates. It was observed as shown in FIG. 10 that antibodies to either RAP or to the lysosomal enzyme detect LRP-bound RAP-LE, were found to bind to the fusion on Western blots, indicating that the fused proteins were intact and folded. Comparing signal intensity, it is further observed that the fusion is bound by the immobilized LRP to a similar extent as RAP alone.

Figure 6:
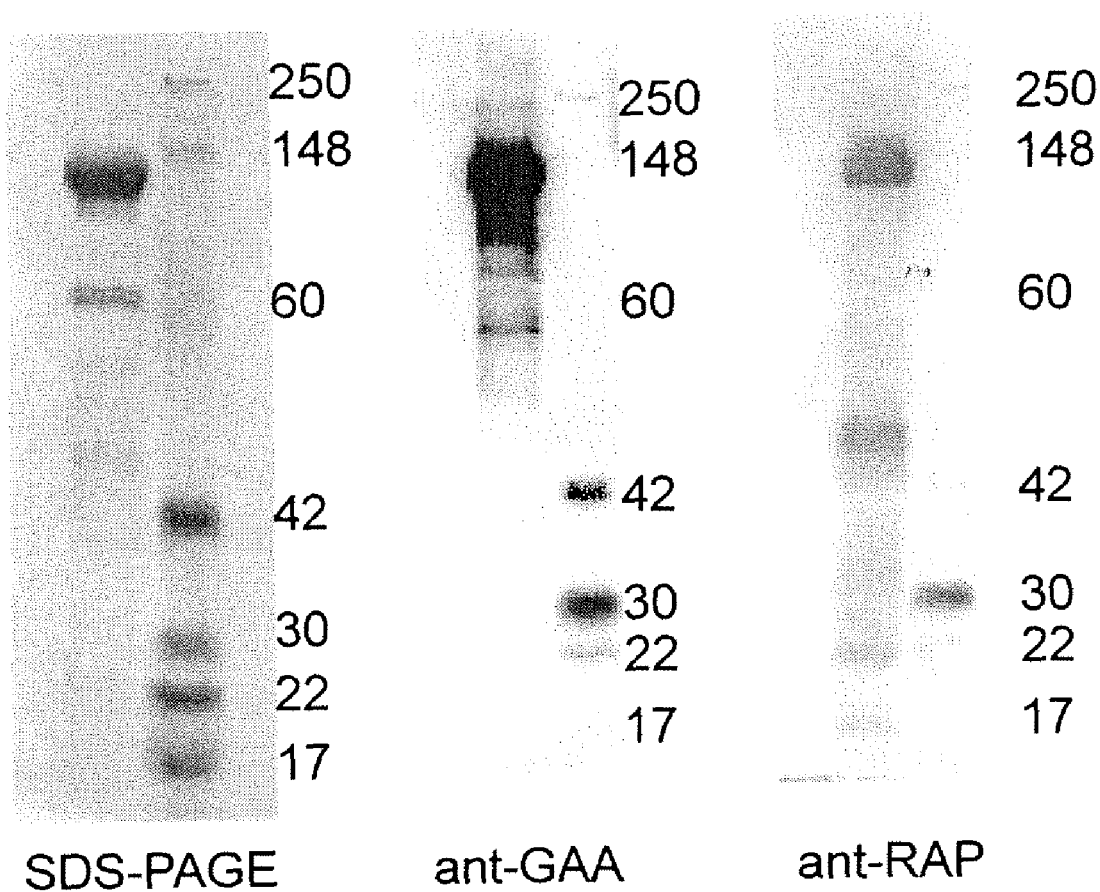
FIG. 6. Characterization of the RAP-GAA fusion.
Figure 7:
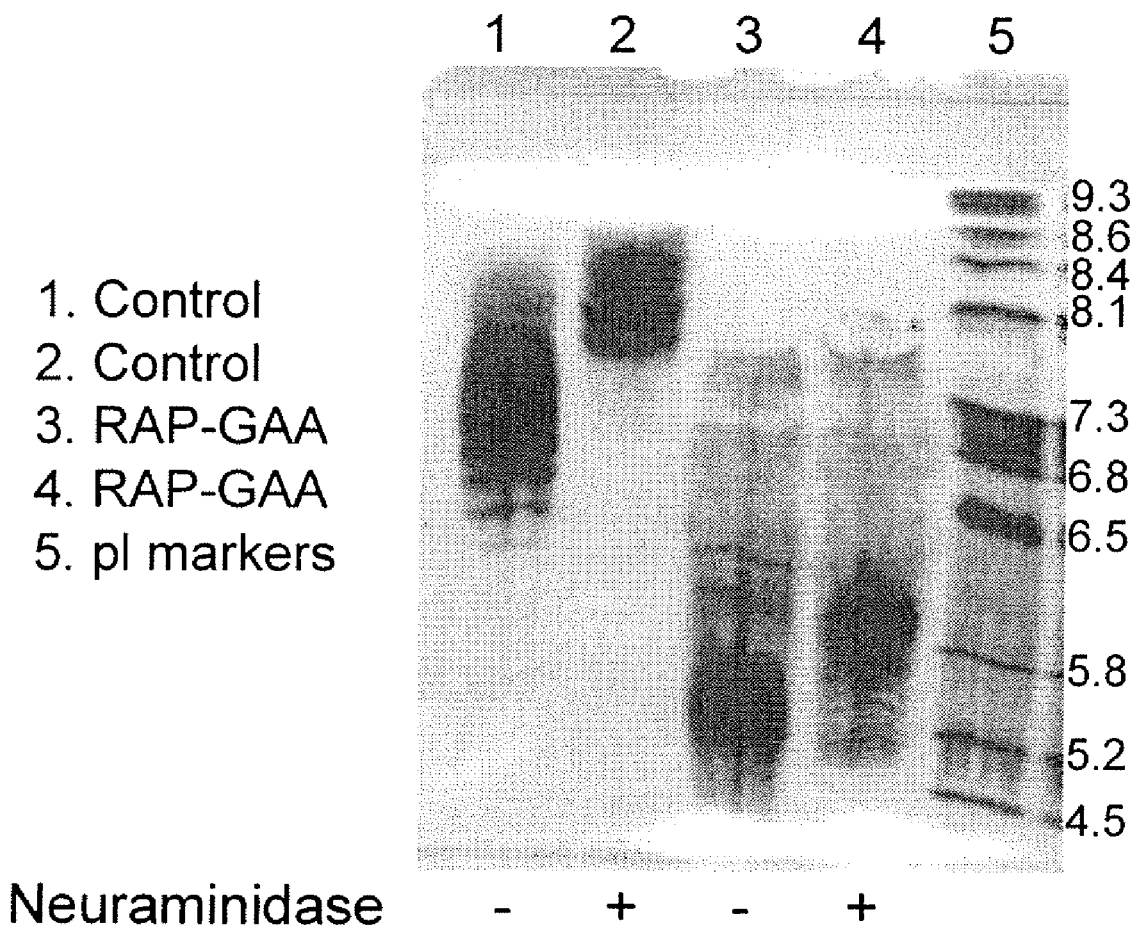
FIG. 7. Assay for complex oligosaccharides on RAP-GAA.
Figure 8:
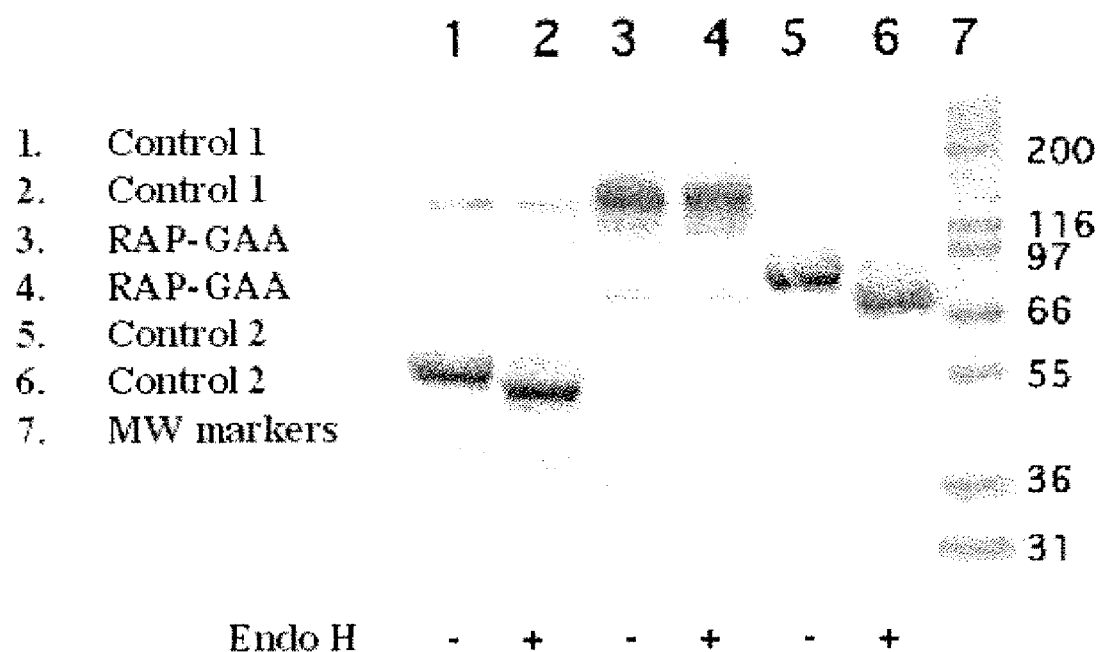
FIG. 8. Assay for high-mannose oligosaccharides on RAP-GAA.

Characterization of RAP-GAA Fusion:

Purified RAP-GAA was tested to determine identity, purity and carbohydrate content. For the identity test, fusion was resolved on SDS-PAGE, blotted to PVDF and probed with anti-GAA and anti-RAP antibodies. A single band of about 150 kD cross-reacted with both antibodies (FIG. 6). Fusion purity was determined by Coomassie Blue staining of the SDS-PAGE gel and was estimated to be >95%. Presence of complex oligosaccharides was measured by digestion with neuraminidase and comparison to undigested samples on an IEF gel. Neuraminidase digestion resulted in a quantitative shift in mobility to a more basic pI, consistent with the presence of complex oligosaccharides (FIG. 7). Endo H digestion was used to test for the presence of high-mannose oligosaccharides. Unlike control proteins, no change in molecular weight of the fusion was observed on SDS-PAGE gels after Endo H digestion. This suggests the absence of high-mannose oligosaccharides on the fusion (FIG. 8).

Figure 9:
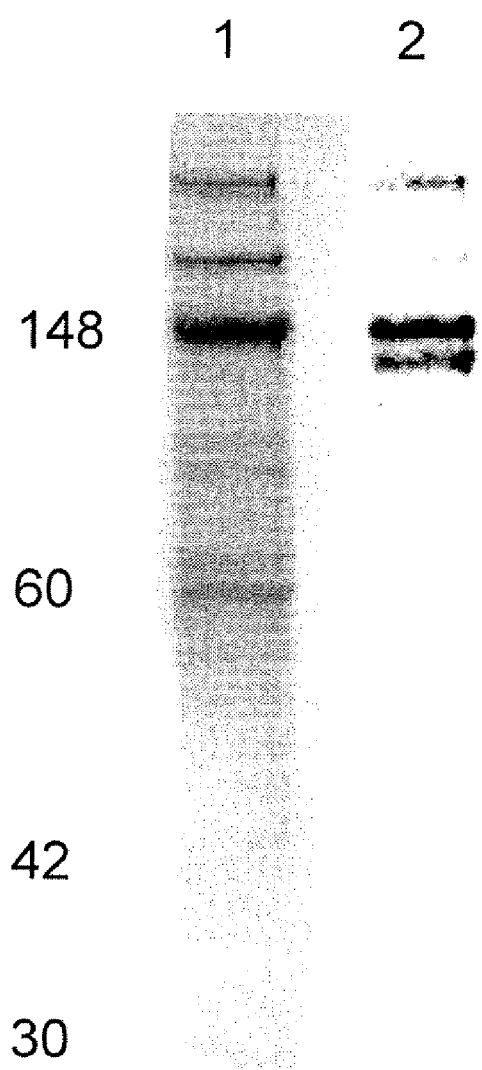
FIG. 9. Characterization of RAP-IDU fusion.

Purification of the RAP-IDU Fusion:

Blue sepharose 6 Fast Flow resin is used for the first purification step. The harvest fluid was adjusted to pH 7.0 and loaded onto a Blue-Sepharose column at a 70 mL/mL resin basis. The column was equilibrated with 75 mM NaCl, 20 mM $Na_2HPO_4$ pH 7.0. RAP-IDU eluted off the column at 1.2 M NaCl, 20 mM $Na_2HPO_4$ pH 7.0. The eluted fraction containing RAP-IDU (determined by iduronidase activity assay) was then exchanged into 75 mM NaCl, 20 mM $Na_2PO_4$ pH 7.0 and loaded onto a Heparin CL 6B resin. RAP-IDU was eluted from the Heparin column at 0.5 M NaCl pH 7.0. The eluted fusion was then adjusted to 2M NaCl, 20 mM $Na_2HPO_4$ pH 7.0 and loaded directly onto a Phenyl-Sepharose column. As a final step, RAP-IDU was eluted from this column at between 0.3 to 0.5M NaCl. Fusion purity was estimated by SDS-PAGE at >80% (FIG. 9).

Example 3

Uptake and Distribution of Unconjugated RAP to the Brain

The distribution of RAP to brain was measured using a mouse in situ perfusion model. Volumes of distribution (Vd) for RAP, the positive control transferrin and the negative control albumin, were determined over a perfusion interval of 5 minutes. In addition, the relative quantities of the test proteins in the vascular and parenchymal fractions of the perfused brain were determined using the capillary depletion technique (Gutierrez et al., J. Neuroimmunol., 47(2):169-76, 1993). The results shown in FIG. 11 include an observed, corrected Kinflx of 1 µL/g/min for transferrin. RAP had an observed, corrected $K_{influx}$ of 2.2 µL/g/min. RAP is taken up into brain.

Figure 11:
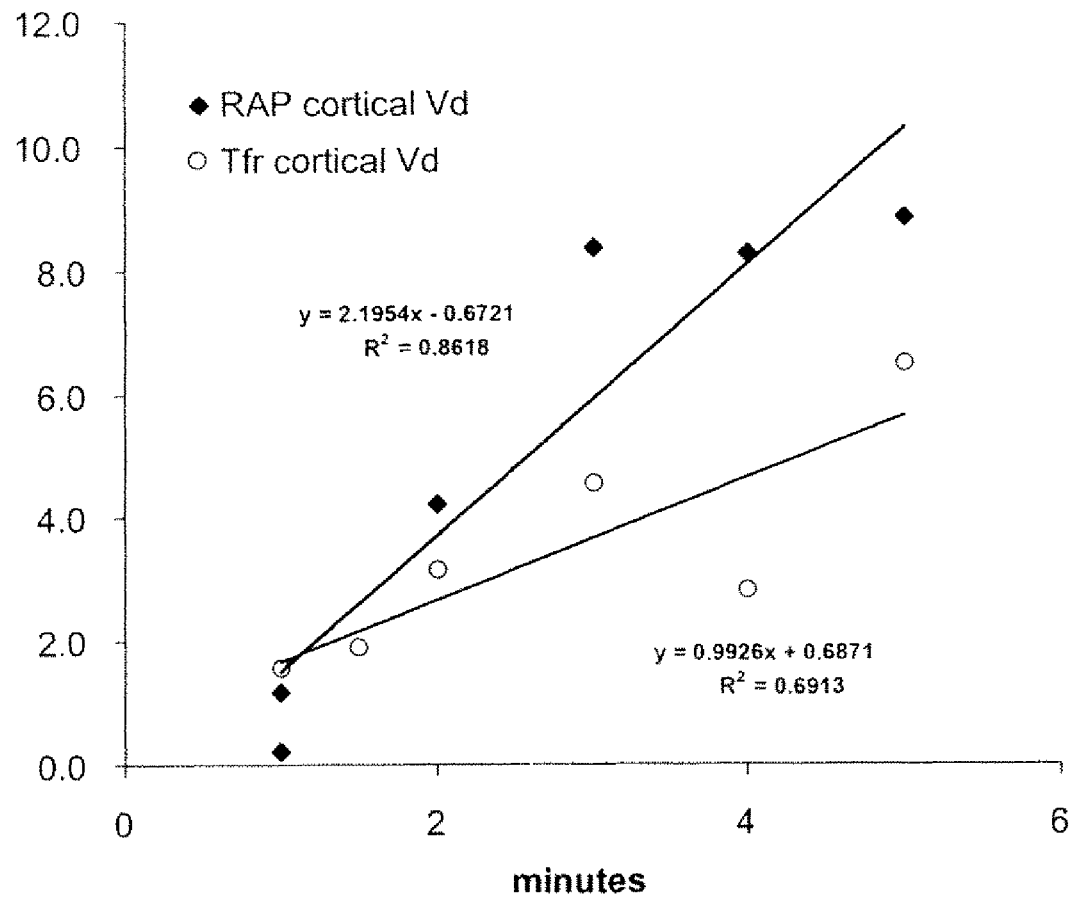
FIG. 11. Corrected Vd vs. perfusion time for iodinated RAP and transferrin at 15 minutes.
Figure 12:
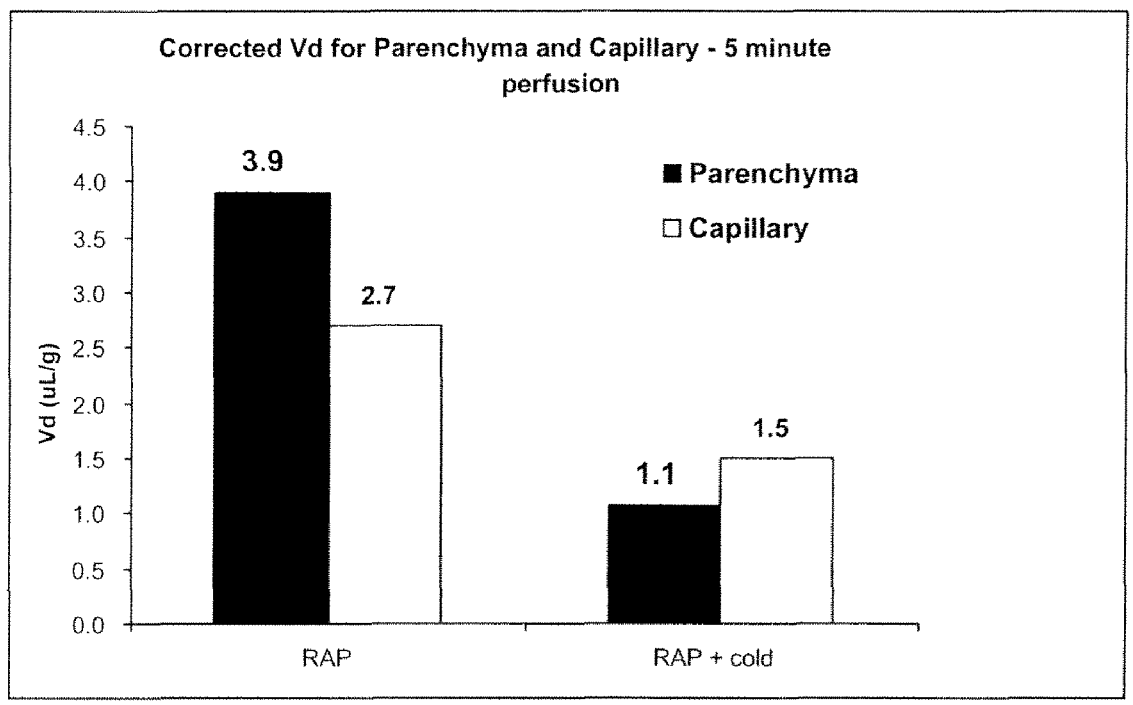
FIG. 12. Distribution of RAP between brain capillary endothelium and brain parenchyma.

A separate experiment was carried out at a single, 5-minute time-point to determine whether RAP is able to traverse the brain vasculature and enter the parenchyma. Brains were harvested as before, but were subjected to a capillary depletion procedure to determine the levels of RAP and albumin in the vascular and parenchymal spaces. Following harvest, the isolated cortex was weighed and placed in a Dounce homogenizer on ice. The cortex was immediately homogenized in 0.7 ml of capillary buffer (10 mM HEPES, 141 mM NaCl, 4 mM KCl, 2.8 mM $CaCl_2$, 1 mM $NaH_2PO_4$, 1 mM $MgSO_4$, 10 mM glucose, pH 7.4) for 10 strokes, after which 1.7 ml of 26% dextran was added and the mixture further homogenized with an additional 3 strokes on ice. To separate the different tissue fractions, 1.3 ml of the homogenate was loaded in an ultracentrifuge tube. The homogenate was centrifuged at 9000 rpm (5400×g) for 15 min at 4° C. in a Beckman TLV-100 swinging-bucket rotor. The parenchymal portion (supernatant) and the capillary portion (pellet) were than separately counted in a dual-channel gamma counter. A sample of post-CNS perfusate was also counted for the Vd calculation. Unlabeled RAP was included as a competitor in some cases to determine whether uptake into brain tissue was saturable (5 µg of unlabeled RAP per mouse, about 80-fold excess over labeled RAP). Results were plotted as corrected Vd (FIG. 11). Each data point is an average derived from 5-6 mice. FIG. 12 shows the distribution of RAP between brain capillary endothelium and brain parenchyma. These results indicate RAP crosses the blood-brain barrier to enter brain parenchyma and that the process of uptake is saturable.

Example 4

Measurement of Specific Uptake of RAP-GAA into Enzyme-Deficient Patient Fibroblasts The uptake of RAGA into cells deficient in GAA was characterized. The cell line used was GM244 (Coriell Cell Repository), a primary cell line isolated from a patient with glycogen storage disorder type II (Pompe's disease). These fibroblasts take up phosphorylated, recombinant GAA via the mannose-6-phosphate receptor, but also have LRP1 receptors, which bind RAP. In order to identify the receptors involved in uptake of different test ligands, samples containing excess free RAP or mannose-6-phosphate were prepared.

Dilutions of RAP-GAA were made in the uptake medium (Dulbecco's Modified Eagle's Medium supplemented with 25 mM HEPES pH 7.0, 2 mM L-glutamine and 250 µg/mL bovine serum albumin) to yield fusion protein concentrations of 33, 11, 3.7, 1.2, 0.4, and 0.1 nM. The effect of 3 mM mannose-6-phosphate, 500 nM RAP and a combination of the two on the uptake of 5 nM RAP-GAA was also assayed. The GM244 fibroblasts was seeded into 12-well plates and allowed to grow for 3 days prior to the uptake experiment.

To initiate uptake, the growth medium was aspirated from the wells and each sample dispensed into duplicate wells at 1 ml per well. Plates were incubated for 4 hours at 37° C., 5% $CO_2$. Samples were then aspirated from each well, the wells washed with phosphate-buffered saline (PBS), and pre-warmed 0.25% trypsin/0.1% EDTA added to each well at 370 for 5 minutes to release the adherent cells. Released cells were pelleted and rinsed with chilled PBS. Pre-chilled lysis buffer (phosphate-citrate buffer, pH 4.0 with 0.15% Triton X-100) was then added and the pellets resuspended by gentle vortexing. Lysed cells could be stored at −80° C.

To measure the levels of GAA activity in the lysed cells, the frozen lysates were thawed at room temperature. Lysate (50 µl) was added directly to duplicate wells in 96-well opaque microtiter plates. Pre-warmed GAA fluorescent substrate (4-methylumbelliferyl-alpha-D-glucoside, 100 µL) was added to each well to initiate the reaction. The plate was incubated at 37° C. for 30 minutes and the reaction terminated by addition of 150 µl glycine/carbonate buffer pH 10. Fluorescence was measured in a plate reader at an excitation wavelength of 366 nm and an emission wavelength of 446 nm.

The results in FIG. 13 show that RAP-GAA is taken up by GM244 fibroblast cells. The $K_{uptake}$ was ~19 nM as determined by a non-linear fit enzymatic algorithm described in the GraFit software program (Sando and Neufeld, Cell, 12(3): 619-27, 1977). Approximately 60-fold more RAP-GAA gets into the fibroblasts than recombinant GAA ($V_{max}$ ratio); 25-fold more at 10 nM. Additionally, 90% of the RAP-GAA fusion uptake is inhibited by 50 nM RAP while only 20% of the uptake is inhibited by 3 mM mannose 6-phosphate. The uptake of the native GAA is almost completely inhibited by mannose 6-phosphate, suggesting alternate receptor pathways for RAP-GAA and recombinant GAA.

Example 5

Measurement of RAP-GAA Uptake and Lysosomal Localization in LRPnuII CHO Cells Expressing Different LRP Receptor Family Members (LRP1B, LDLR, VLDLR) and into BN Cells Expressing only LRP2 (Megalin, gp330)

Iodine labeling: RAP-GAA or recombinant GAA were radiolabeled with $^{125}I$ using the IODO-GEN reagent.

Cells were seeded in 12-well plates at a density of 200,000 cells/well and used after overnight culture. On the day of the experiment, cells were rinsed twice in ice-cold ligand binding buffer (Minimal Eaglets medium containing 0.6% bovine serum albumin; BSA), and $^{125}I$-RAP-GAA or GAA alone were then added in the same buffer (0.5 ml/well). The initial ligand concentrations tested were 10 nM. Binding was carried out at 4° C. for 30 min with gentle rocking in the presence or absence of unlabeled 500 nM RAP or 10 mM mannose-6-phosphate to confirm receptor-binding specificity. Unbound ligand was then removed by washing cell monolayers three times with ice-cold binding buffer. Ice-cold stop/strip solution (0.2 M acetic acid, pH 2.6, 0.1 M NaCl) was then added to one set of plates without warming and kept on ice prior to counting. Dissociation constants for the receptor-ligand complexes were determined from the resulting binding data. The remaining plates were then placed in a 37° C. water bath, and 0.5 ml of ligand binding buffer prewarmed to 37° C. was added to the well monolayers to initiate internalization. At each time point (every 30 seconds for 2 minutes and every 3 minutes thereafter) the wells were placed on ice, and the ligand-binding buffer replaced with ice-cold stop/strip solution. Ligand that remained on the cell surface was stripped by incubation for 20 minutes (0.75 ml for 10 minutes, twice) and counted. Internalization rates were determined from this data. Cell monolayers were then solubilized with SDS lysis buffer (62.5 mM Tris-HCl, pH 6.8, 0.2% SDS, and 10% (v/v) glycerol) and counted. The sum of ligand that was internalized added to that which remained on the cell surface after each assay was used as the maximum potential internalization. The fraction of internalized ligand after each time point was calculated and plotted.

Measurement of ligand degradation efficiency (transport to lysosomes after internalization): Cells were seeded at a density of 200,000 cells/well into 12-well dishes 1 day prior to assays. On the day of the experiment, pre-warmed assay buffer containing RAP-GAA or GAA alone was added to cell monolayers in the presence or absence of unlabeled 500 nM RAP or 10 mM mannose 6-phosphate, followed by incubation for 4 hours at 37° C. Following incubation, the medium overlaying the cell monolayers was removed and proteins were precipitated by addition of BSA to 10 mg/ml and trichloroacetic acid to a final concentration of 20%. Lysosomal degradation of ligands was defined as the appearance of radioactive fragments in the medium that were soluble in 20% trichloroacetic acid. The protein concentrations of each cell lysate were measured in parallel dishes that did not contain LRP ligands. The RAP-GAA and GAA degradation efficiencies were calculated as the value of degraded radioactive material (soluble cpm/mg cell protein) divided by the number of cell surface LRP family receptors (as determined previously by flow cytometry, data not shown).

Example 6

Measurement of Specific Uptake of RAP-LE in to Enzyme-Deficient Patient Fibroblasts with Concomitant Clearance of Stored Glycosaminoglycans Patient fibroblasts are seeded and grown to confluence in 12-well plates. On the day of the experiment, cells are fed with fresh medium lacking $MgSO_4$ and containing 4 µCi/mL of $Na_2{}^{35}SO_4$. Cells are also supplemented with RAP-LE fusion or LE alone in the presence or absence of 500 nM RAP or 10 mM mannose 6-phosphate. Cells are harvested each day for 4 days. After rinsing with PBS, cells are lysed by freeze-thaw. Stored GAG is assayed by precipitation with 80% ethanol and quantitated by scintillation counting. Stored GAG values are normalized to the protein content of the cell lysates.

Example 7

Measurement of Lysosomal Distribution and Clearance of Storage in Intravenously-Administered RAP-GAA in GAA-Deficient Mice GAA knock out mice (C57B1/6 background) were randomized to four treatment groups and treated every two days with 100 µl of either phosphate-buffered saline, 1.3 mg/kg or 0.33 mg/kg RAP-GAA fusion protein four times via intravenous tail vein injection. Forty-eight hours after the fourth injection, mice were euthanized by carbon dioxide inhalation and the brain, heart, diaphragm, upper and lower body skeletal muscle and liver immediately collected and flash frozen. Three age-matched wild-type mice were also euthanized and tissues collected and frozen. Each tissue is prepared for GAA immunohistochemical staining by embedding in OCT blocks, and for glycogen staining by fixing in glutaraldehyde and embedding in paraffin. The remaining tissues were tested for GAA activity using the fluorescent substrate assay described in Example 4. Serum was collected at sacrifice and tested for GAA antibody.

| Dosing Regimen | | | | | |
|---|---|---|---|---|---|
| Group | # Animals | Test Articles Or Vehicle Articles | Dose (mg/kg) | # Doses | Dose Volume (µl) |
| 1 | 6 KO | PBS | — | 4 | 100 |
| 2 | 6 KO | RAP-GAA | 0.33 | 4 | 100 |
| 3 | 6 KO | RAP-GAA | 1.30 | 4 | 100 |
| 4 | 6 KO | GAA | 1.30 | 4 | 100 |
| 5 | 3 WT | None | None | None | None |

Study day 0   Inject groups 1-4
Study day 2   Inject groups 1-4
Study day 4   Inject groups 1-4
Study day 7   Inject groups 1-4
Study day 9   Bleed groups 1-4 and Sacrifice groups 1-5, Collect tissues groups 1-5

Example 8

Treatment of Patients with MPS-I Disorder

A pharmaceutical composition comprising a conjugated agent comprising therapeutic enzyme linked to RAP is administered intravenously. The final dosage form of the fluid includes the conjugated agent, normal saline, phosphate buffer at pH 5.8 and human albumin at 1 mg/ml. These are prepared in a bag of normal saline.

A preferred composition comprises the conjugated agent (therapeutic enzyme linked to RAP) in an amount ranging from 0.05-0.5 mg/mL or 12,500-50,000 units per mL; sodium chloride solution 150 mM; sodium phosphate buffer 10-50 mM, pH 5.8; human albumin 1 mg/mL. The composition may be in an intravenous bag of 50 to 250 ml.

Human patients manifesting a clinical phenotype of deficiency of lysosomal enzyme, such as in patients with MPS I with an alpha-L-iduronidase level of less than 1% of normal in leukocytes and fibroblasts are included in the study. All patients manifest some clinical evidence of visceral and soft tissue accumulation of glycosaminoglycans with varying degrees of functional impairment. Efficacy is determined by measuring the percentage reduction in urinary GAG excretion over time. The urinary GAG levels in MPS-I patients are compared to normal excretion values. There is a wide range of urine GAG values in untreated MPS-I patients. A greater than 50% reduction in excretion of undegraded GAGs following therapy with the conjugated agent is a valid means to measure an individual's response to therapy. For example, data is collected measuring the leukocyte iduronidase activity and buccal iduronidase activity before and after therapy in MPS I patients. Clinical assessment of liver and spleen size is performed as it is the most widely accepted means for evaluating successful bone marrow transplant treatment in MPS-I patients (Hoogerbrugge et al., Lancet 345:1398, 1995).

Example 9

Lysosomal Storage Diseases that May be Treated with Corresponding RAP-LE Conjugates The diseases that can be treated or prevented using the methods of the present invention are: Mucopolysaccharidosis I (MPS I), MPS II, MPS IIIA, MPS IIIB, Metachromatic Leukodystrophy (MLD), Krabbe, Pompe, Ceroid Lipofuscinosis, Tay-Sachs, Niemann-Pick A and B, and other lysosomal diseases. For each disease the conjugated agent would comprise a specific compound or enzyme. For methods involving MPS I, the preferred compound or enzyme is α-L-iduronidase. For methods involving MPS II, the preferred compound or enzyme iduronate-2-sulfatase. For methods involving MPS IIIA, the preferred compound or enzyme is heparan N-sulfatase. For methods involving MPS IIIB, the preferred compound or enzyme is α-N-acetylglucosaminidase. For methods involving Metachromatic Leukodystropy (MLD), the preferred compound or enzyme is arylsulfatase A. For methods involving Krabbe, the preferred compound or enzyme is galactosylceramidase. For methods involving Pompe, the preferred compound or enzyme is acid α-glucosidase. For methods involving CLN, the preferred compound or enzyme is tripeptidyl peptidase. For methods involving Tay-Sachs, the preferred compound or enzyme is hexosaminidase alpha. For methods involving Niemann-Pick A and B the preferred compound or enzyme is acid sphingomyelinase.

Example 10

Further Exemplification of Receptor Binding, Cell Uptake and Lysosomal Delivery of Fusions of RAP and α-L-Iduronidase or Acid α Glucosidase The present example provides additional data demonstrating the efficient LRP receptor binding, cell uptake and lysosomal delivery of therapeutic enzymes using RAP as a delivery vehicle.

Fusion expression constructs—The human RAP coding sequence, encompassing amino acids 35-353, was amplified from human liver cDNA using PfuTurbo polymerase (Stratagene) and the primers RAPF 5'-GCGATAGGAT CCTACTCGCGGGAGAAGAACCAGC-CCAAGCCGTCCCC GA-3' (SEQ ID NO:12) and RAPR 5'-GCGATAAACCGGTTTCTGC CTCGGCGC-GAGCTCTGGAGATCCTGCCGGACAGGTCC T-3' (SEQ ID NO:13). This fragment does not include sequence encoding either the signal peptide or the HNEL ER retention signal. The 5'-RAP primer incorporates an in-frame BamHI site at the 5' end. The 3'-RAP primer adds sequence encoding a six amino acid spacer (AEAETG; SEQ ID NO: 29) including an in-frame AgeI site at the 3'-end. The modified RAP sequence was cloned into the vector pC3B as an in-frame fusion with either human alpha-L-iduronidase (amino acids 27-652) or human alpha-glucosidase (amino acids 70-952). Both lysosomal enzyme sequences were 5'-modified to remove their signal peptides and to add an in-frame AgeI site. The expression vector is derived from pcDNA3.1 (+) (Invitrogen) and includes the rabbit beta-actin IVS2, the rat preproinsulin transcript leader sequence and the first 18 amino acids (signal peptide) of human melanotransferrin ending with an in-frame BamHI site.

Plasmid vectors were linearized with AclI and transfected into CHO-K1 LRP⁻ (CHOdL) using standard protocols. Clones were selected by limiting dilution in medium containing 800 μg/mL G418. Clones were screened for expression using fluorescent monosaccharide substrates for the respective lysosomal enzymes. A clone expressing RAP-IDU (CHOdL-R17) and a clone expressing RAP-GAA (CHOdL-RG20) were selected for further studies.

Expressions of fusions—CHOdL-R 7 and CHOdL-RG20 were cultured in T-flasks in a protein-free medium supplemented with 2.5% fetal bovine serum. Production was carried out in the absence of serum in pH, oxygen and temperature-controlled 3 L Applikon bioreactors. Cells were grown on Cytopore 1 beads (Amersham) for the production phase. Microcarriers were retained during perfusion using an internal settler (Biotechnology Solutions). Bioreactor perfusion rates were determined my monitoring residual glucose.

Purification and specific activity of RAP fusions—RAP-IDU cell culture medium was clarified by passage through a SartoPore 1.2 depth filter and then for sterility by passage through a 0.2 μm PES membrane filter. The sterile, clarified medium was pH adjusted and then sequentially resolved on Heparin Sepharose CL-6B (Amersham), Phenyl Sepharose HP (Amersham), and SP Sepharose Fast Flow (Amersham). Enzymatically active fractions were pooled, concentrated and, when necessary, buffer-exchanged for the next step using a 50 kDa mini-TFF membrane (Vivascience). The final buffer was 10 mM Sodium Phosphate pH 5.8, 150 mM Sodium Chloride. RAP-GAA was purified with or without non-binding passage through DEAE Fast Flow (Amersham). The RAP-GAA fusion was then sequentially resolved on Heparin Sepharose CL-6B (Amersham) and Phenyl Sepharose HP (Amersham). In-process and final eluates were treated as described for RAP-IDU.

Enzyme activity assays—Enzyme activity was measured by the hydrolysis of small fluorigenic monosaccharide substrates using 96-well plate adaptations of published methods. For RAP-IDU activity, the substrate 4-methylumbelliferyl iduronide (4-MUI) was used at a concentration of 2.5 mM. For RAP-GAA activity, the substrate 4-methylumbelliferyl-alpha-D-glucoside was used at a concentration of 5.4 mM. Activity units are defined as micromoles of substrate hydrolyzed per minute at 37° C.

Characterization of oligosaccharides by FACE—FACE analysis was performed essentially as described previously (Starr et al., J. Chromatogr. A., 720(1-2):295-321, 1996; Hague et al., Electrophoresis, 19(15):2612-20). Briefly, proteins were denatured and treated with N-glycanase to release N-linked oligosaccharides. Isolated oligosaccharides were then fluorescently labeled with aminonaphthalene-6-sulfonate by reductive amination and resolved on polyacrylamide gels with fluorescence detection. Band identity was inferred by measuring mobility relative to known standards. When necessary, oligosaccharide identities were confirmed by additional FACE analysis after digestion with specific exoglycosidases.

Characterization of sialylation by IEF—Purified fusions were treated with *Clostridium perfringens* neuraminidase (Sigma) in 50 mM Sodium Acetate buffer pH 5 at 37° C. for an hour. Treated samples and untreated controls were analyzed by IEF on a pH 3-9 gradient gel (Amersham Phastgel System).

Degradation of fusions by lysosomal proteases in vitro—Lysosomal proteases Cathepsin B, D and L were purchased from Calbiochem, resuspended in 50 mM Sodium Acetate pH 5 and stored frozen. For the digests, 0.5 μg of each fusion was incubated with 10 ng of an equimolar mixture of the cathepsins (approximately 300 μM final concentration for each) in 100 mM Sodium Acetate, 100 mM Sodium Chloride, 0.5 mM DTT, pH 4.5 for 1 hour at 37° C. Reactions were quenched with SDS-PAGE sample-loading buffer containing 2% SDS and heated for 5 minutes at 95° C. Samples were resolved on Nu-PAGE 4-12% Bis-Tris SDS-PAGE gels and stained with Coomassie blue.

Expression and purification of sLRP2—As previously described (Bu and Rennke, J. Biol. Chem., 271(36):22218-24 1996).

Expression of human lysosomal enzymes—Human alpha-L-iduronidase (Aldurazyme) was a kind gift from BioMarin Pharmaceutical and Genzyme Therapeutics. Human lysosomal alpha-glucosidase was expressed and purified using proprietary methods. The purified enzyme is greater than 95% pure and carries at least one bis-phosphorylated oligomannose structure per molecule of protein (based on FACE analysis and retention on a mannose 6-phosphate receptor column, unpublished results).

Ligand blots—PVDF membranes (Millipore) were pre-wet in methanol and then equilibrated in PBS (11.9 mM Sodium Phosphate, 137 mM Sodium Chloride, 2.7 mM Potassium Chloride pH 7.4). Membranes were then mounted in a Bio-Rad dot blot apparatus. The second ligand-binding domain of LRP1 (sLRP2, 1 µg/well) was applied to the membrane by vacuum filtration. The membrane was then cut into sections that were placed in separate wells of a 24-well plate. Membranes were blocked in TBS (20 mM Tris pH 7.4, 150 mM Sodium Chloride) with 5 mM Calcium Chloride and 3% non-fat dry milk for 30 minutes. Ligands were incubated with each membrane spot for 2 hours at room temperature. Individual blots were washed 2x5 minutes each with blocking buffer and then incubated with different antibodies in block buffer for one hour at room temperature to detect binding.

Uptake into cell lines—Human fibroblasts were obtained from the Coriell Cell Repository. Rat C6 glioblastoma cells and mouse C2C12 myoblasts were obtained from the American Type Culture Collection. Typically, uptake was performed in serum-free medium containing 20 mM HEPES pH 7.0 and 0.5 mg/mL bovine serum albumin. Appropriate test proteins and inhibitors were diluted into the same medium and incubated with cells for various intervals. Cells were then rinsed with PBS, and trypsinized. Pellets were collected by low-speed centrifugation, washed with PBS, and lysed by freezing at −80° in the presence of 0.1% Triton X-100. Lysates were clarified by centrifugation. The soluble lysate fractions were assayed for enzyme activity and for total protein using the bicinchonic acid method.

Glycosaminoglycan clearance in human Hurlerfibroblasts mediated by the RAP-idu fusion—Human GM01391 Hurler fibroblasts were obtained from the Coriell Cell Repository and grown in DMEM 10% Fetal Bovine Serum and 2 mM glutamine. Four days prior to the clearance experiment, cells were seeded on 6-well plates at 250,000 cells per well. On the day of the experiment, cells were fed with sulfate-free medium (S-MEM, Irvine Scientific), 15% dialyzed Fetal Bovine Serum, 5 mM Calcium Chloride, 110 mg/L Sodium Pyruvate for an hour and then the same with 4 µCi/mL 35S-sodium sulfate and 5 nM of either RAP-idu or iduronidase alone. Cells were incubated in this medium for 48 hours at 37° C. in a humidified cell-culture incubator with 5% $CO_2$/95% air. Cell layers were rinsed three times with PBS before and after trypsinization. Pellets were lysed in 0.5N Sodium Hydroxide and neutralized with 1 M Hydrochloric Acid. Protein concentrations were determined by BioRad Protein assay in 96-well plates. Lysate was counted in Beckman Ready Caps.

Results

Expression and characterization of fusions—RAP fusions were configured such that the RAP coding sequence was located N-terminally to the lysosomal enzyme coding sequence. The order of the sequences was based on previously published studies demonstrating that GST-RAP fusions, in which RAP is located C-terminally to GST, had up to ten-fold lower affinity for LRP than RAP alone Warshawsky et al., J Clin Invest 92, 937-944, 1993). A CHO-K1 mutant (CHOdL) was chosen for production of the RAP fusions (FitzGerald et al., J. Biol. Chem., 129, 1533-1541, 1995). CHOdL does not express any LRP receptors, preventing reuptake and degradation of secreted protein by the over-expressing cell line. Fusions between RAP and both IDU (RAP-IDU) and GAA (RAP-GAA) were expressed in this system. Clones for each fusion were selected based on enzyme activity in the cell culture medium and scaled-up for production in bioreactors. Volumetric productivity values were calculated from activity concentrations (U/L) and the specific activities (U/mg) of purified rhIDU or rhGAA. Calculated in this way, the average daily reactor productivities were 1-2 mg/L-day for RAP-IDU and 10-15 mg/L-day for RAP-GAA.

Figure 19A:
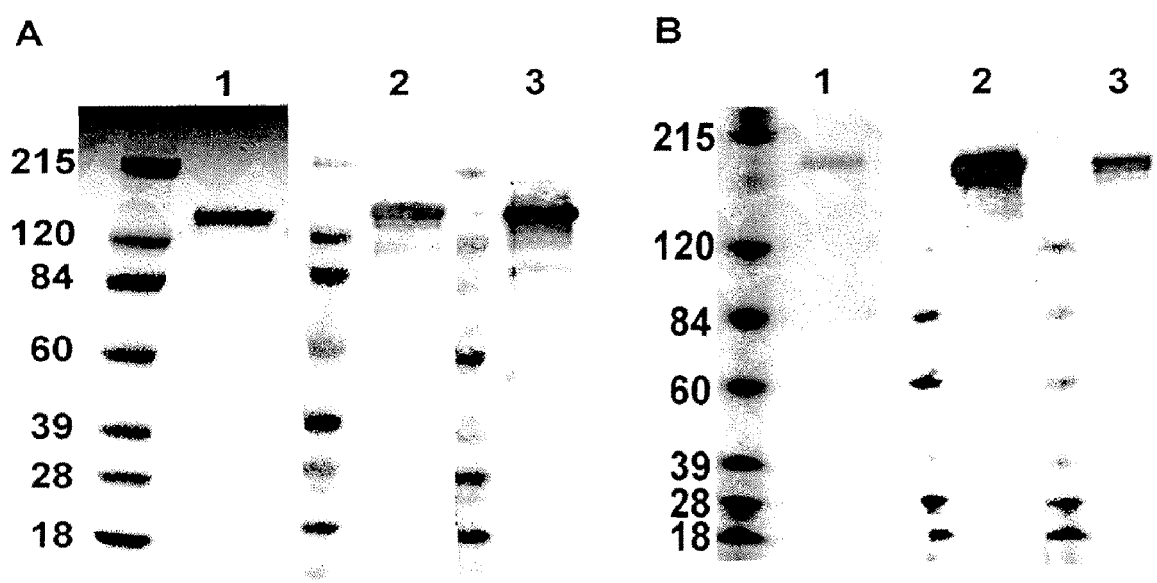
FIG. 19A-19C.

Purification and characterization of fusions—Fusions were purified to >95% using conventional resins (FIG. 19A, lane 1). Anti-RAP antibodies (FIG. 19A, lane 2) and either anti-IDU or anti-GAA antibodies (FIG. 19A, lane 3) co-stained bands consistent with the molecular weights of each fusion on Western blots of conditioned cell culture medium. While stable in conditioned medium, the fusions were observed to be sensitive to proteolytic cleavage events during purification that resulted in the removal of RAP from the N-terminus of both fusion proteins. Proteolysis was mitigated by addition of protease inhibitors to the conditioned medium prior to purification.

Molar specific activities of the purified fusions were calculated by dividing enzyme activity concentrations (U/mL) by protein concentrations (nmol/mL) of the fusion. Fusion concentrations were calculated from $A_{280}$ measurements and theoretical extinction coefficients (Table A).

TABLE A

Physical parameters of RAP fusion proteins

|  | rhIDU | RAP-IDU | rhGAA | RAP-GAA |
| --- | --- | --- | --- | --- |
| Amino acids | 627 | 952 | 883 | 1208 |
| Apparent MW (SDS-PAGE) | 83 kD | 125 kD | 110 kD | 150 kD |
| Theoretical protein MW | 70 kD | 108 kD | 98 kD | 136 kD |
| Theoretical $\epsilon M^{-1} cm^{-1}$ | 118280 | 154410 | 159890 | 196020 |
| Activity concentration | 104 U/mL | 7.4 U/mL | 6.2 U/mL | 5.1 U/mL |
| Protein concentration | 8.3 nmol/mL | 1.3 nmol/mL | 21 nmol/mL | 16 nmol/mL |
| Molar specific activity | 12.5 U/nmol | 5.7 U/nmol | 0.29 U/nmol | 0.32 U/nmol |
| $K_m$ (4-MUI) | 0.3 mM | 0.3 mM | NA | NA |
| $V_{max}$ (Units at 24° C.) | 1.65 | 1.22 | NA | NA |
| Bis-7 | +++ | + | +++ | − |

Figure 19B:
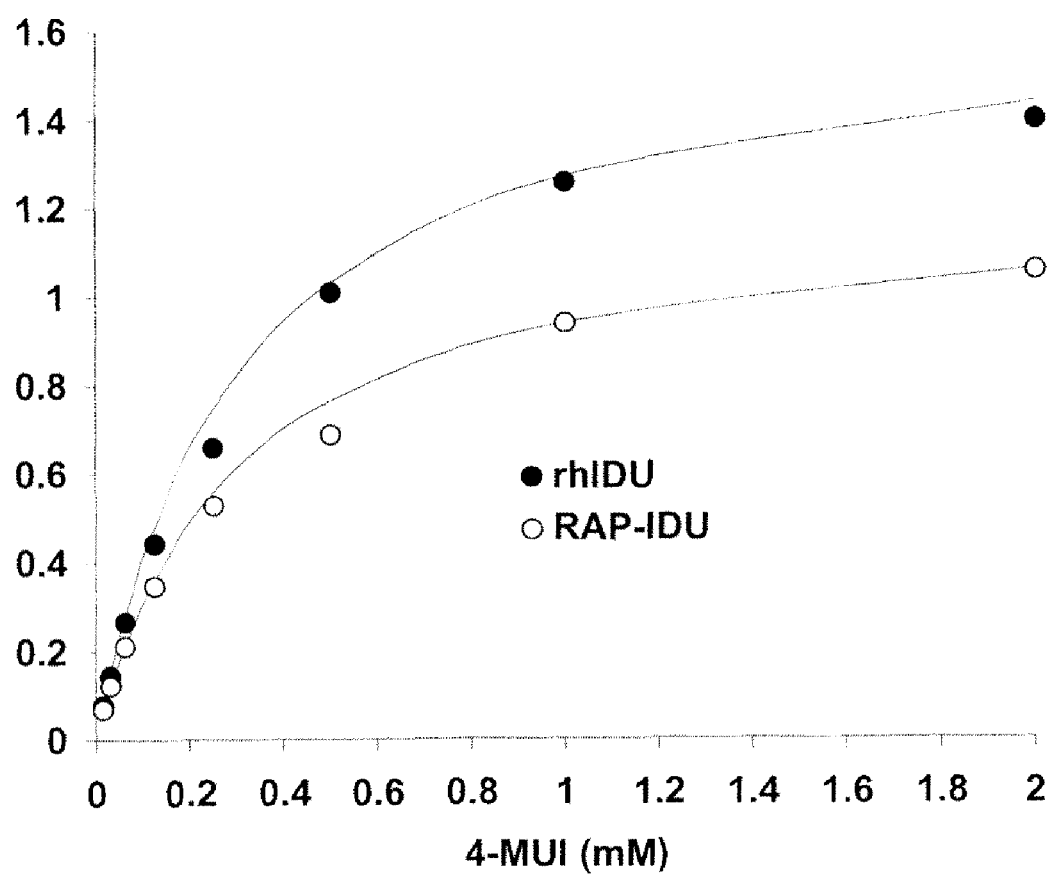

RAP-IDU had a molar specific activity of 5.7 U/nmol, while rhIDU had a molar specific activity of 12.5 U/nmol. The substantial difference in molar specific activities for RAP-IDU and rhIDU suggests that RAP interferes in some way with the catalytic activity of IDU within the context of the fusion. The diminished activity of the fusion could involve restriction of access to the active site, alterations in the folding of IDU or other conformational constraints that affect protein motions involved in catalysis. In order to gain more insight into the catalytic differences between rhIDU and RAP-IDU, kinetic parameters for cleavage of 4-MUI were measured (FIG. 19B). While the $K_m$ values for the two proteins were indistinguishable, the $V_{max}$ for rhIDU exceeded that of RAP-IDU by 25%. This difference is consistent with some constraint being imposed on the motion of IDU within the context of the fusion rather than restricted access to the active site. RAP-GAA and rhGAA were found to have nearly identical molar specific activities.

Figure 19C:
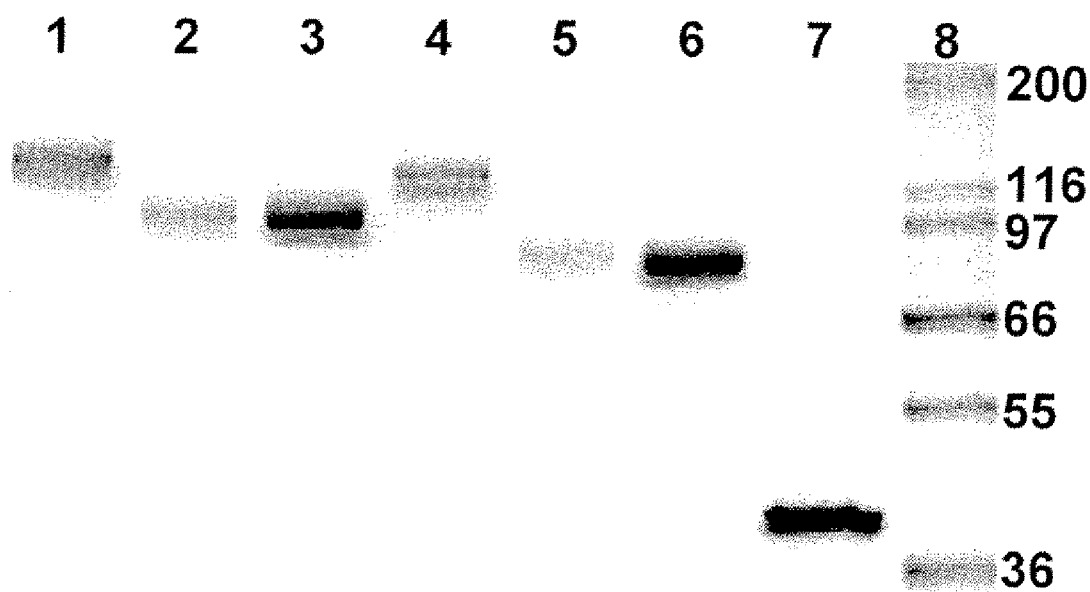

Digestion of RAP fusions with lysosomal proteases—To simulate the behaviour of the fusions in the lysosome, preparations of RAP-IDU and RAP-GAA were incubated with a mixture of cathepsin D, B and L at pH 4.5 at 37° C. for 1 hour. Digested proteins were analyzed by SDS-PAGE. RAP was degraded under these conditions, leaving the lysosomal enzyme intact (FIG. 19C, lanes 2 and 5). The major band remaining for each of the two fusions was slightly larger than rhIDU and rhGAA. The additional mass may be an indication that some RAP or linker sequence remains after treatment. N-terminal sequencing and peptide mapping indicate that cleavage occurs at multiple sites within the last 20 amino acids of RAP and the linker sequence. GAA activity per volume of digest was not significantly affected by in vitro proteolysis. This result is consistent with the similar molar specific activities of RAP-GAA and rhGAA. IDU activity per volume of digest increased by 26% after in vitro proteolysis of the fusion, suggesting a partial restoration of the enzymatic activity of the released IDU moiety compared to rhIDU. The specific activity of fusion-derived IDU after delivery to the lysosome was not determined.

Figure 20A:
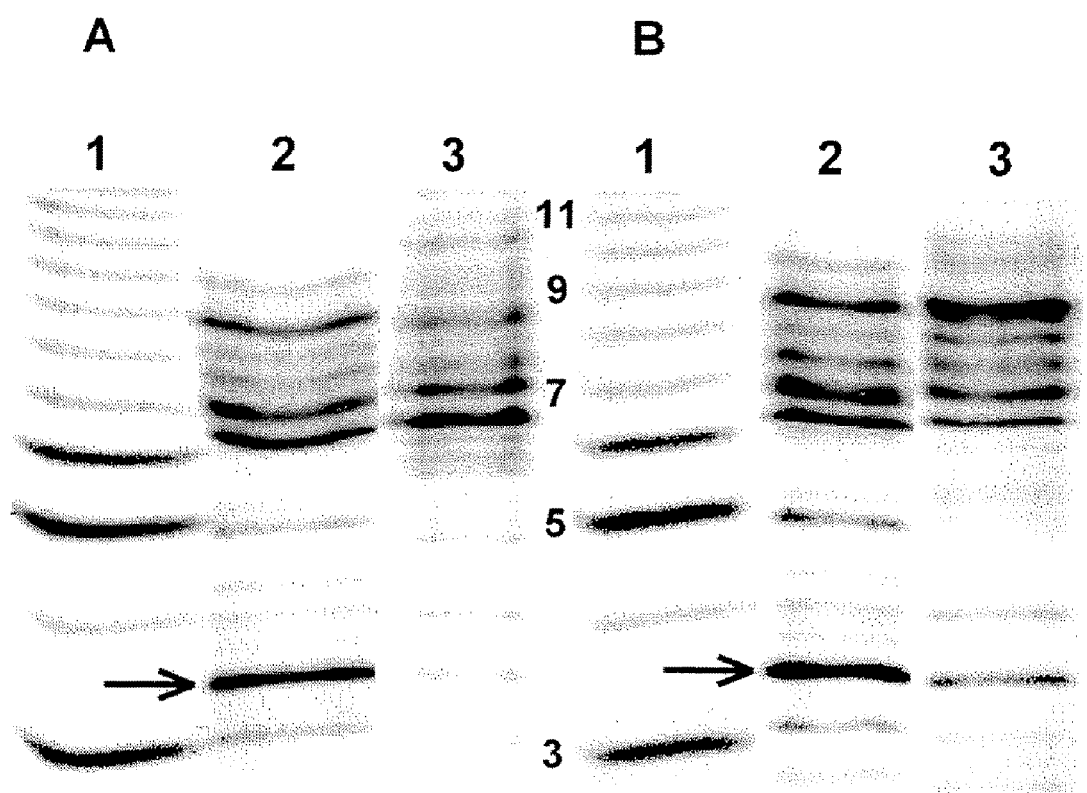
FIG. 20A-20C.
Figure 20B:
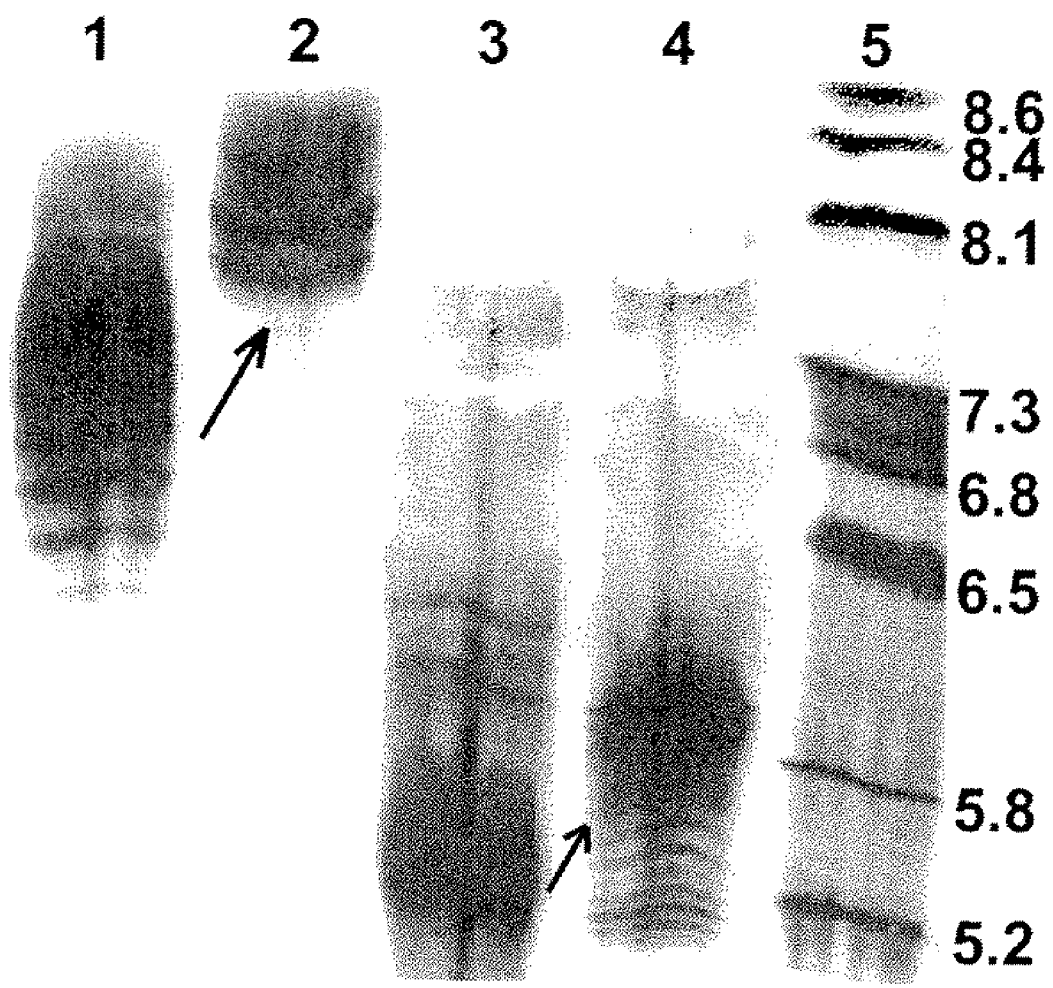

Characterization of RAP fusion oligosaccharides—Given the important role that oligosaccharide receptors play in the uptake of lysosomal enzymes in vivo, the identity and types of oligosaccharides present on the RAP fusions was determined. First, purified fusions were subjected to FACE analysis to measure levels of phosphorylated oligosaccharides relative to the native lysosomal enzymes (FIG. 20A). Phosphorylated oligosaccharides are readily identified by their characteristic mobilities on FACE gels. Both rhIDU and rhGAA possessed significant amounts of bis-phosphorylated oligomannose 7 (Bis-7), a structure that is bound tightly by the MPR (Zhao et al., J Biol Chem 272, 22758-22765, 1997; FIG. 20A, lane 2, arrow). Each oligosaccharide band was quantitated by fluorescence intensity. Bis-7 accounted for 30 and 20% of all oligosaccharides on rhIDU and rhGAA, respectively. In both cases, these percentages are consistent with 1-2 molecules of Bis-7 for each molecule of enzyme. While the rhIDU and RAP-IDU oligosaccharide profiles were otherwise similar, the fusion carried 60% less Bis-7 compared to the enzyme alone (FIG. 20B, lane 3). This value equates to roughly one molecule of Bis-7 for every three molecules of RAP-IDU fusion. The rhGAA and RAP-GAA oligosaccharide profiles were also similar (compare FIG. 20A, lanes 2 and 3), but, in contrast to RAP-IDU, no phosphorylated oligosaccharides were found in significant amounts on the RAP-GAA fusion.

To test for complex oligosaccharides terminating in sialic acid, the RAP-GAA fusion was subjected to IEF analysis after treatment with neuraminidase (FIG. 20B). A shift of the fusion to more basic isoelectric points provided evidence that RAP-GAA contained sialylated complex oligosaccharide (compare FIG. 20B lanes 1 and 2). The positive control, rhIDU, underwent a similar shift upon treatment with neuraminidase (compare FIG. 20B lanes 3 and 4).

Figure 20C:
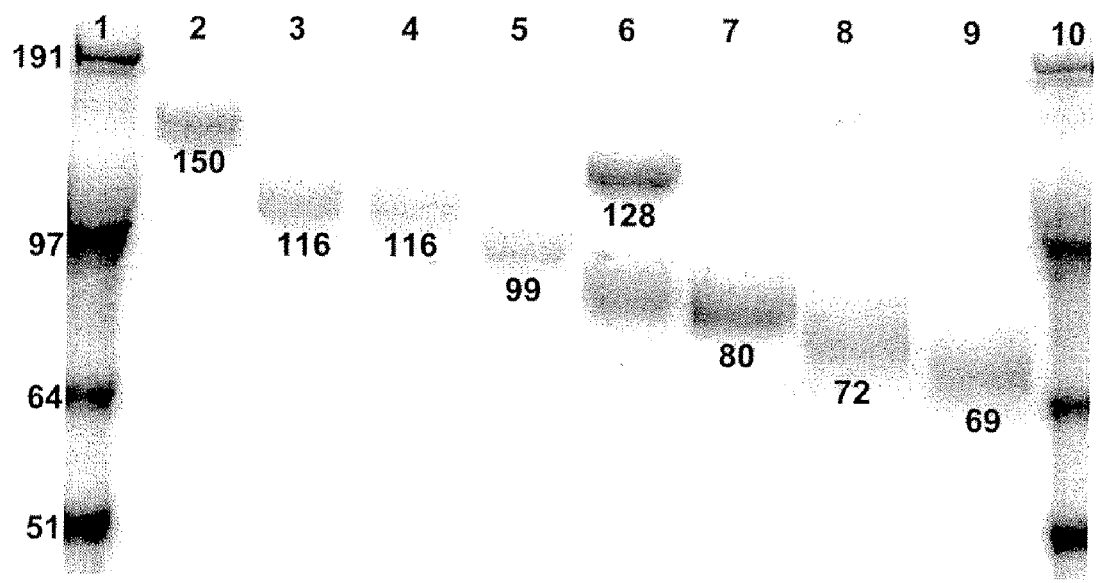

The large size of the fusions made it difficult to analyze oligosaccharide mass and content by digestion with glycosidases. To reduce the size of the protein component, samples of RAP-IDU and RAP-GAA were digested with cathepsins. Proteolyzed fusions were then further digested with Endo H or N-glycanase to release high-mannose oligosaccharides and total oligosaccharides, respectively. This experiment does not address the oligosaccharide content of the RAP portion of the fusion since this is lost upon cathepsin proteolysis. RAP has one glycosylation site. Endo H digestion of proteolyzed RAP-GAA had little effect on band mobility, indicating minimal high-mannose or hybrid oligosaccharides on the GAA part of the fusion (FIG. 20C, compare lanes 3 and 4). Digestion of proteolyzed RAP-GAA with N-glycanase resulted in a band shift of 17 kD. This result is consistent with the isoelectric focusing experiment in that both demonstrate high levels of complex oligosaccharides on the RAP-GAA fusion. In contrast with RAP-GAA, Endo H digestion of proteolyzed RAP-IDU resulted in a significant band-shift, consistent with the presence of high-mannose or hybrid oligosaccharides on fusion-derived IDU (compare FIG. 20C lanes 7 and 8). The RAP-IDU sample used for this experiment was already partly proteolyzed during purification. By mass, the loss upon digestion of IDU with endo H accounted for the majority of the total loss observed upon digestion with N-glycanase (FIG. 20C lane 9).

Figure 21:
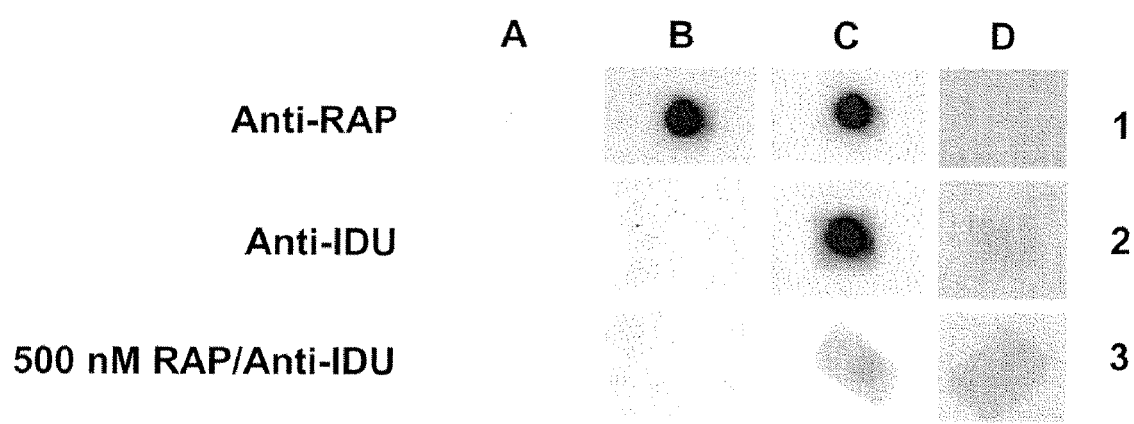
FIG. 21. sLRP2 ligand blot: The second ligand-binding domain of LRP1 was blotted to nylon membrane and probed with ligands in the presence or absence of excess RAP. Bound ligands were detected by Western blotting with indicated antibodies. Ligands were: Buffer alone, column A; RAP, column B; RAP-IDU, column C; rhIDU, column D.

Ligand blotting—Recombinant sLRP2, the entire second ligand-binding domain of human LRP1, was spotted onto nylon membrane filters (FIG. 21). After blocking, individual filters were incubated with RAP (column B), RAP-IDU (column C) or rhIDU (column D) in binding buffer. Filters were washed and probed with anti-RAP (row 1) or anti-IDU antibodies (row 2). Judging by signal intensity, RAP-IDU bound to the receptor fragment as well as RAP alone under these conditions (columns B and C, row 1). Binding of RAP and RAP-IDU could be blocked with excess cold RAP (column C, row 3). Recombinant human IDU did not bind to sLRP2 (column D). These results demonstrate that the RAP moiety within the RAP-IDU fusion retains the ability to specifically bind to LRP.

Uptake of RAP fusions into patient fibroblasts—To determine whether RAP fusions could be taken up into cells in culture, RAP-IDU, RAP-GAA, rhIDU or rhGAA were added to primary human fibroblasts isolated from either Hurler (IDU-deficient, GM1391) or Pompe (GAA-deficient, GM244) patient. Test protein concentrations for the uptake experiments were calculated from $A_{280}$ measurements and theoretical extinction coefficients. Following an interval of one to two hours to allow for uptake, cells were harvested, lysed and assayed for lysosomal enzyme activity. Uptake signal is reported in units of fluorescent substrate cleaved per volume of lysate. Identical numbers of cells were used in each well and normalizing the activity data to total protein in each sample did not change the results. Curves were fitted to hyperbolic functions and uptake parameters derived using GraphFit (Erithacus Software). The hyperbolic asymptote value is defined here as the maximum uptake capacity. The concentration of fusion or enzyme giving half-maximal uptake is defined, as it has been previously, as $K_{uptake}$ (Sando and Neufeld, Cell, 12(3):619-27, 1977).

Figure 22A:
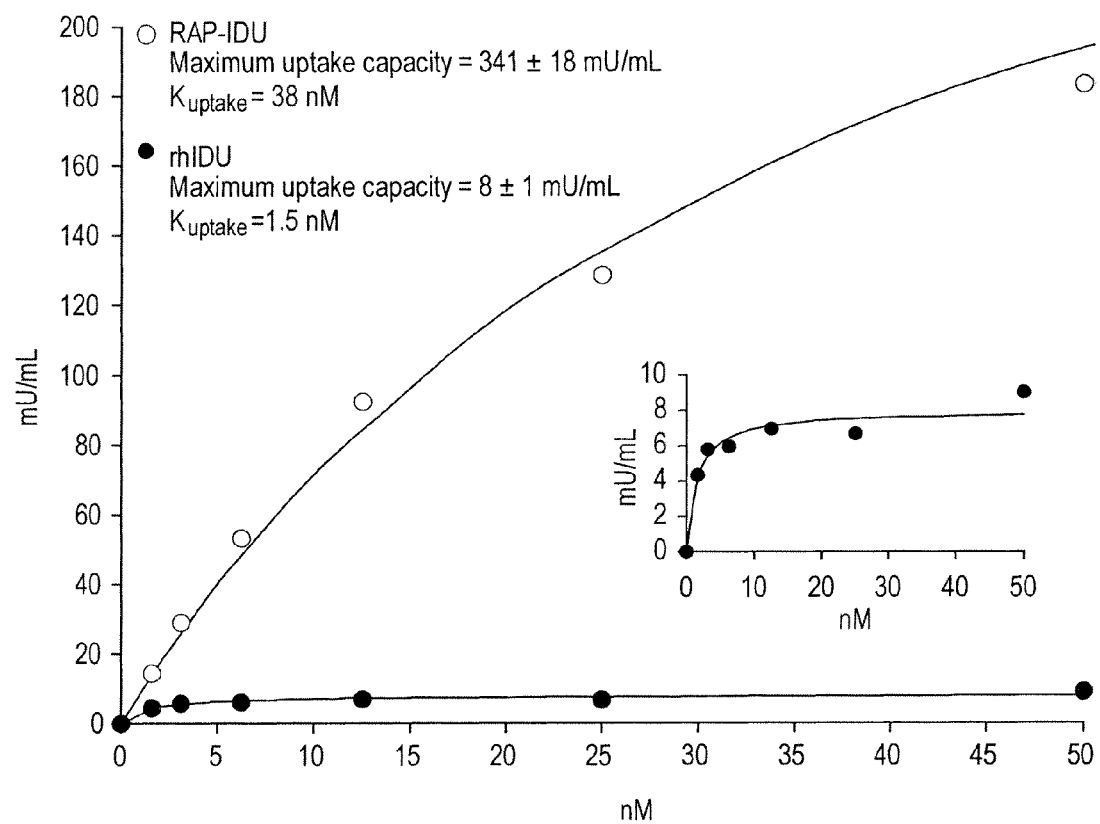
FIG. 22A-22F.
Figure 22B:
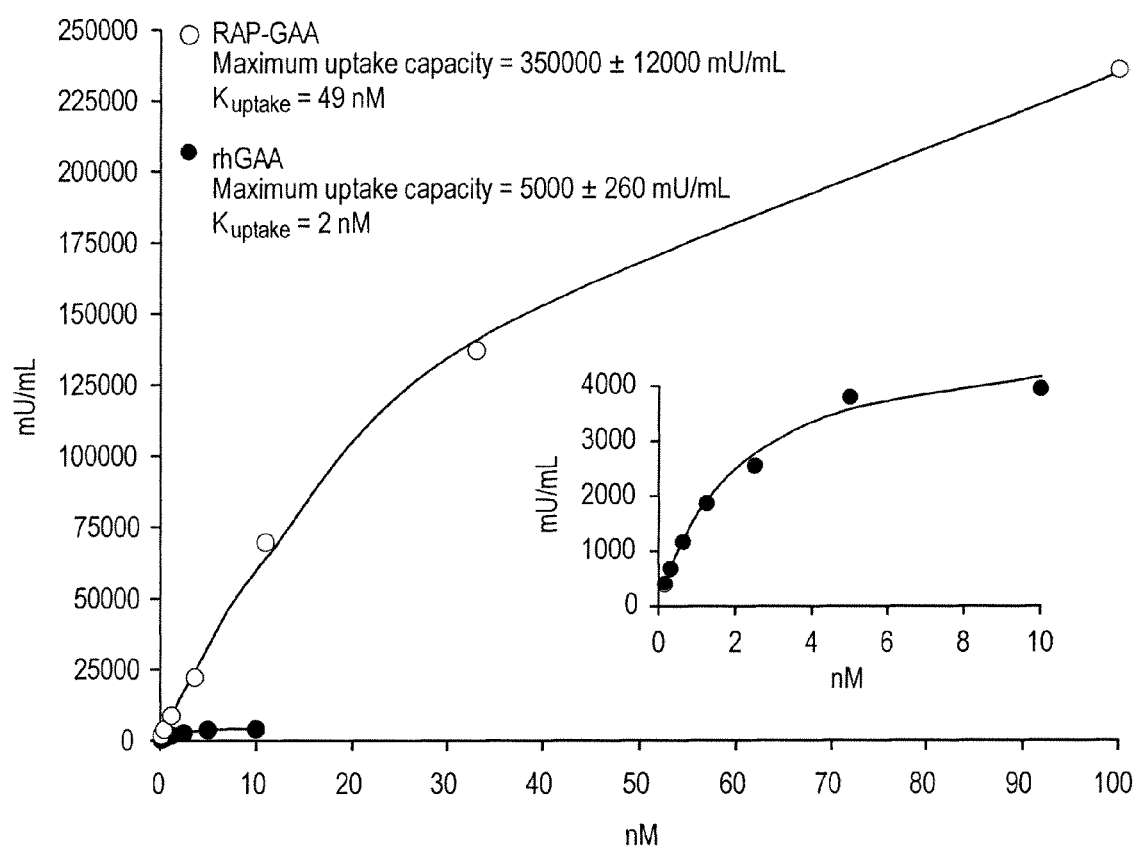

Fibroblasts in culture were found to take up significantly more RAP fusion than enzyme alone (FIG. 22A, B and Table B). This difference became more pronounced at higher concentrations of fusion and enzyme. In particular, the maximum uptake capacity for the fusion in Hurler fibroblasts exceeded that of the free enzyme by 43-fold in the case of RAP-IDU despite a 25-fold $K_{uptake}$ advantage for the rhIDU. Since the specific activity of the RAP-IDU fusion is about half that of rhIDU, uptake of fusion may be underestimated in this experiment. The maximum uptake capacity for RAP-GAA in Pompe fibroblasts exceeded that of rhGAA by 70-fold despite a 25-fold $K_{uptake}$ advantage for rhGAA (FIG. 22B).

TABLE B

Ratios of fusion to enzyme uptake at equimolar concentrations in different cell lines

| Fusion | enzyme | cell type | Uptake ratio (fusion/enzyme) | | | $K_{uptake}$ |
| --- | --- | --- | --- | --- | --- | --- |
| | | | 5 nM | 50 nM | saturation | |
| RAP-IDU | rhIDU | fibroblast | 7 | 27 | 43 | 25 |
| RAP-GAA | rhGAA | fibroblast | 9 | 37 | 70 | 25 |
| RAP-GAA | rhGAA | C6 glioma | 8 | | | |
| RAP-GAA | rhGAA | C2C12 myoblast | 18 | | | |

Figure 22C:
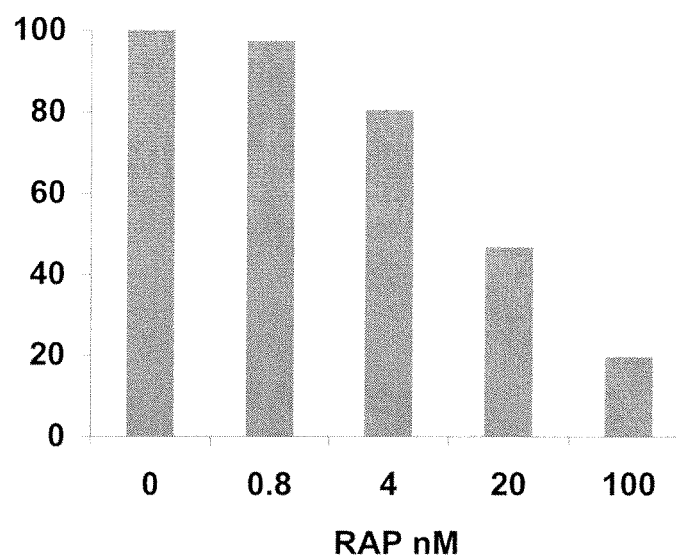
Figure 22D:
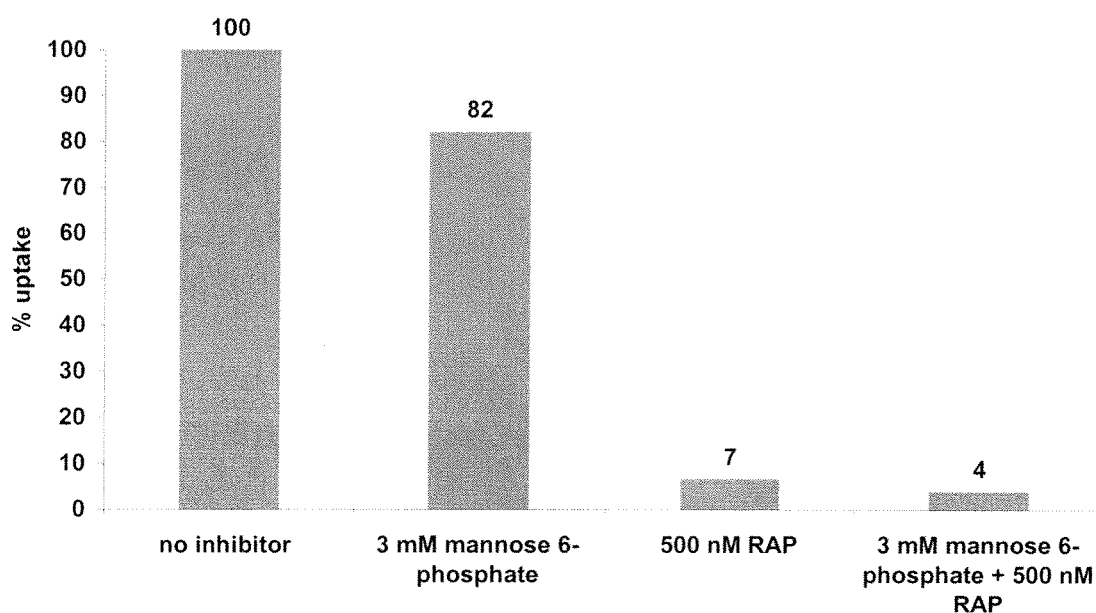

Inhibitors of LRP (RAP) and MPR (mannose 6-phosphate) systems were included in the culture media to determine whether RAP-IDU and RAP-GAA uptake into fibroblasts was receptor-specific. Excess RAP significantly inhibited uptake of RAP-IDU and RAP-GAA in fibroblasts (FIG. 22C and FIG. 22D). Conversely, excess mannose 6-phosphate had minimal effects on the uptake of RAP-GAA into the same cells (FIG. 22D).

Figure 22E:
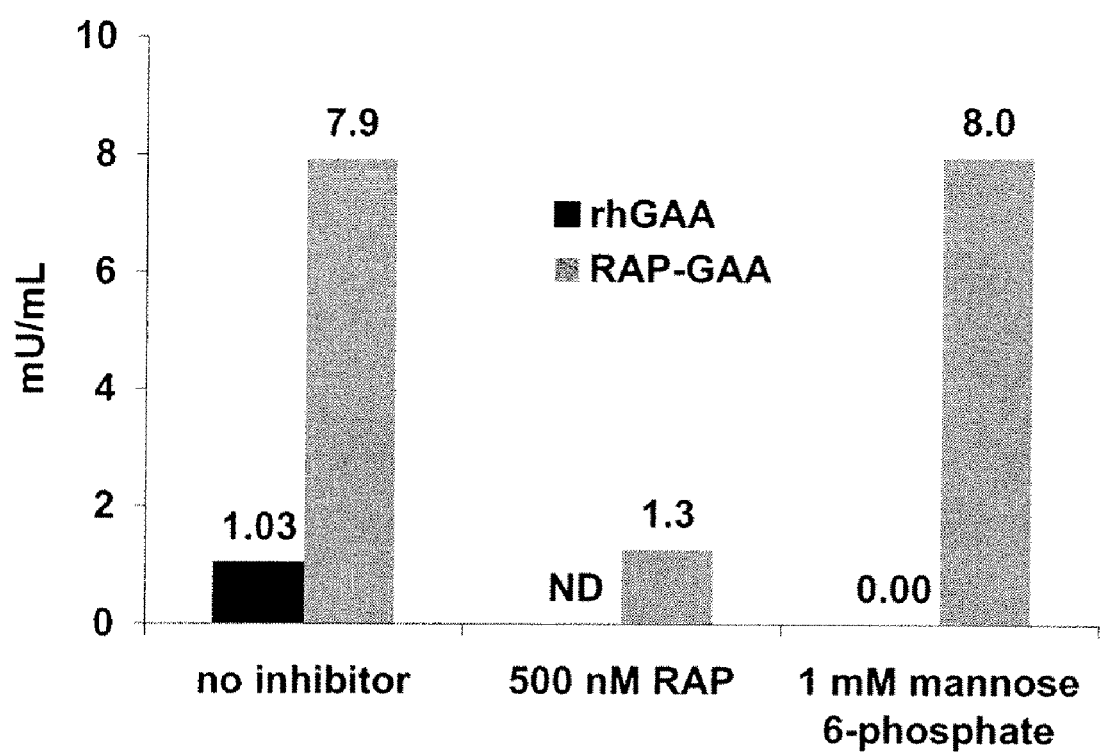
Figure 22F:
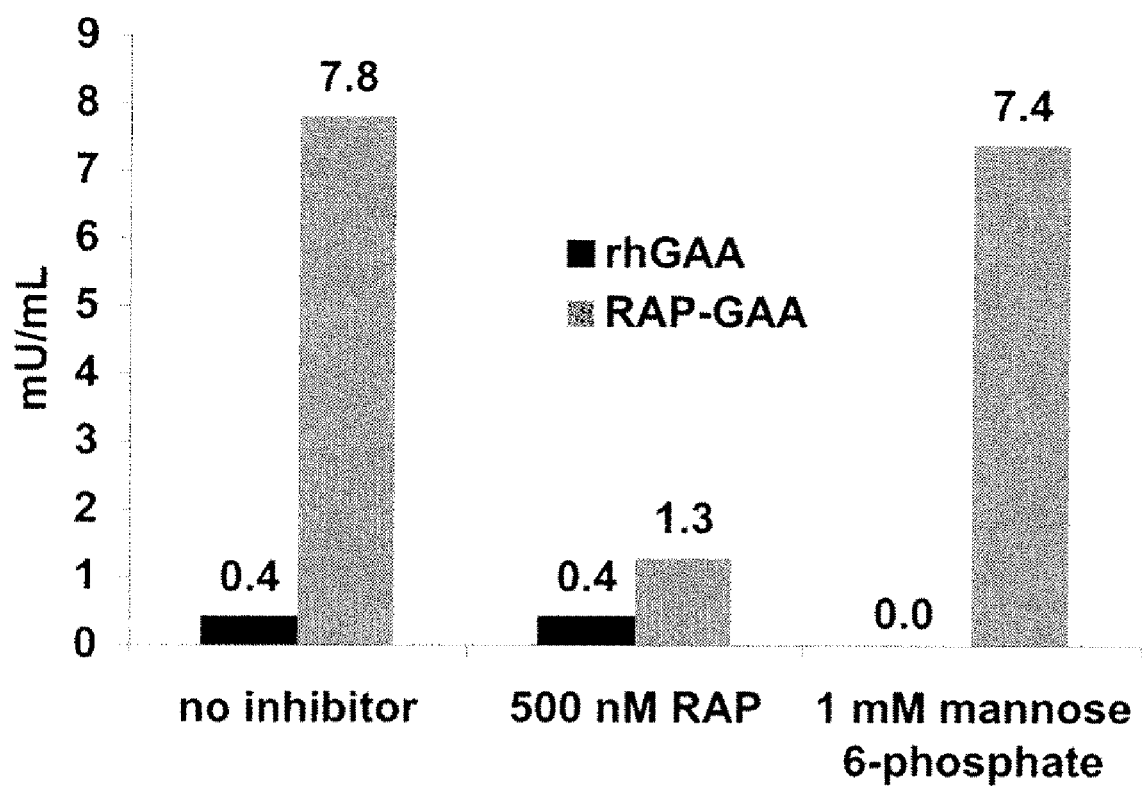

Similar experiments were then carried out using a brain cell line, rat C6 glioma cells (FIG. 22E) and a muscle cell line, mouse C2C12 myoblasts (FIG. 22F). At 5 nM concentrations, the uptake of RAP-GAA into C6 glioma cells was over 7-fold more efficient than rhGAA. Under the same conditions, uptake of RAP-GAA was 18-fold more efficient than rhGAA in C2C12 myoblasts. As was the case in the fibroblasts, uptake of RAP-GAA into either cell line was inhibited by RAP but not by mannose 6-phosphate. These results show that fusions were efficiently endocytosed by cells in culture and that endocytosis occurred via LRP. The relative efficiencies of uptake for the MPR and LRP systems likely depend on the relative density of each receptor on each particular cell type.

Figure 23:
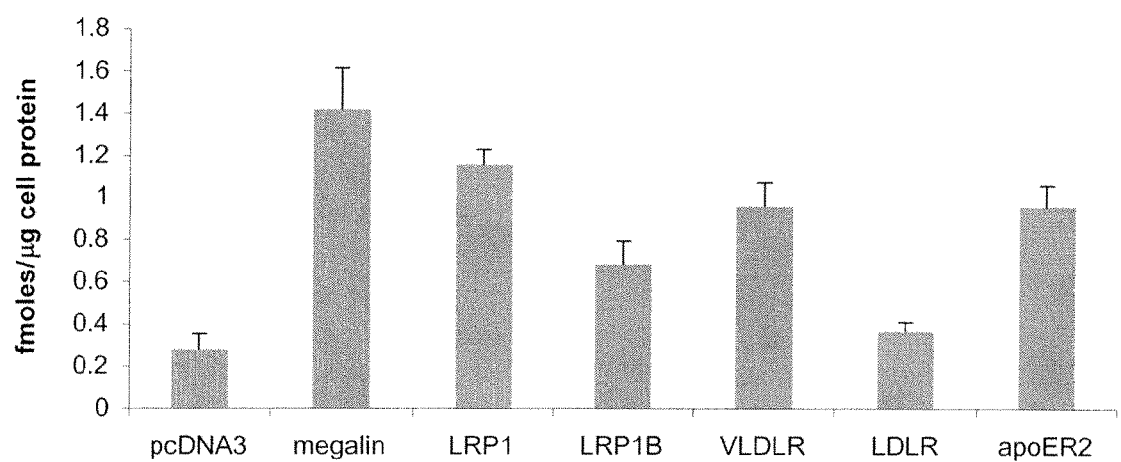
FIG. 23 RAP-GAA uptake mediated by different LRP receptors: Values represent the difference between uptake in the presence and absence of excess cold RAP (receptor-specific uptake). Femtomoles of solubilized $^{125}$I were normalized to total protein in each sample.

Uptake of RAP-GAA by different LRP receptors—In order to determine whether uptake could be mediated by specific LRP receptors, RAP-GAA was radio-iodinated and incubated with a panel of recombinant CHOdL lines expressing different LDLR family members. Brown Norway rat yolk-sac cells (BN) were used as the test line for megalin. LRP1 and LRP1B were represented by mini-receptors comprising roughly the C-terminal third of the full-length proteins, which includes the fourth ligand-binding domain, capable of mediating high-affinity binding of RAP. Additionally, these mini-receptors possess intact cytoplasmic tails and have been previously shown to faithfully reproduce the trafficking behavior of the full-length receptors (Li et al., J. Biol. Chem., 276, 18000-18006, 2001; Obermoeller-McCormick et al., J Cell Sci 114, 899-908, 2001). Uptake of the fusion was determined by measuring the appearance of soluble counts in the cell culture medium. Soluble counts have previously been demonstrated to reflect uptake, lysosomal delivery, degradation and release of labeled amino acids from the cells (Iadonato et al., Biochem J 296 (Pt 3), 867-875, 1993). LRP receptor-specific uptake was calculated by subtracting signal obtained in the presence of excess cold RAP competitor (FIG. 23). RAP-GAA was specifically taken up and degraded by cells expressing megalin, LRP1, LRP1B, VLDLR and apoER2 but not LDLR or cells containing empty vector. These findings are consistent with the fact that LDLR binds to RAP with significantly lower affinity when compared to other members of the LDLR family ($K_d \approx 250$ nM, Medh et al., J Biol Chem 270, 536-540). This experiment confirms that the binding behavior of RAP is predictive of the binding behavior of RAP fusions. Similarly, RAP-inhibitable production of soluble counts indicates that RAP-GAA is endocytosed and lysosomally targeted by the different LRP receptors.

Figure 24:
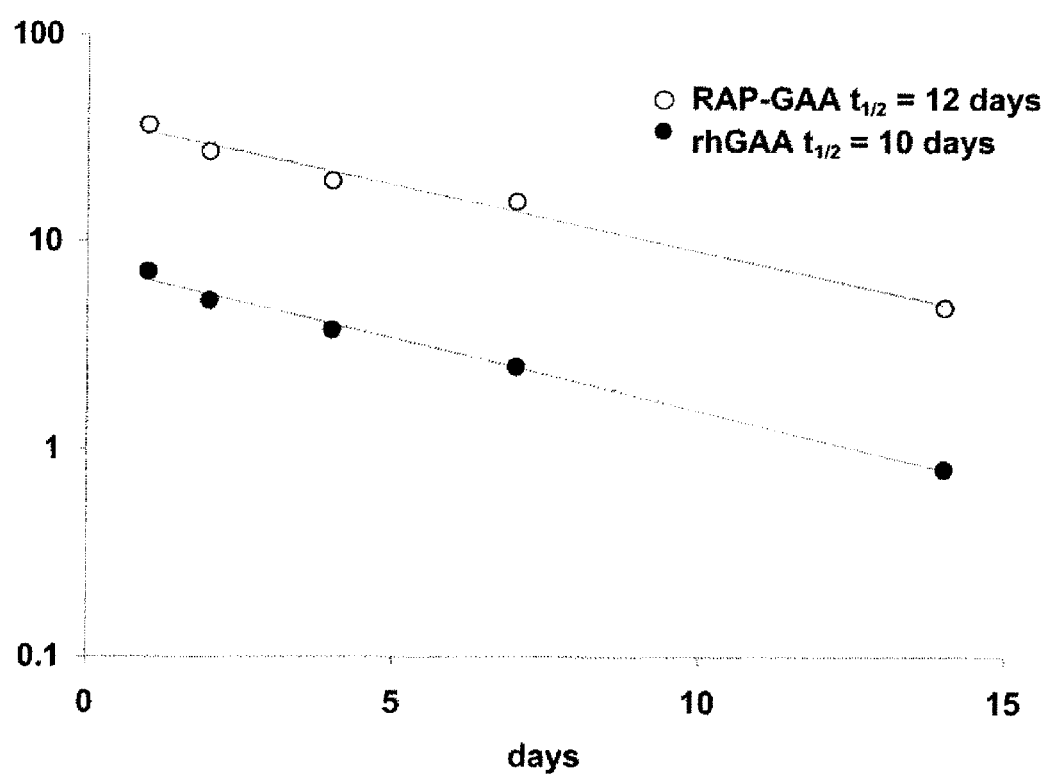
FIG. 24 Intra-cellular half-life of RAP-GAA and rhGAA in GM244 fibroblasts: Proteins were incubated with fibroblasts for 24 hours. Medium was changed and cells were allowed to grow for intervals from 2 to 14 days, followed by lysis and alpha-glucosidase enzyme assay.

Intracellular half-life of RAP-GAA—To test the stability of RAP-delivered lysosomal enzyme in the lysosome, RAP-GAA or rhGAA was incubated with Pompe patient fibroblasts (GM244) in multi-well plates for 24 hours, transferred them to growth medium lacking the test proteins and then harvested the cells over a period of two weeks. Cell lysates were then assayed for GAA activity. Fusion-derived GAA and rhGAA had nearly identical intracellular half-lives of approximately 12 and 10 days, respectively (FIG. 24). Because GAA has a half-life at neutral pH that is measured in hours, the nearly identical, multi-day half-lives of rhGAA and fusion-derived GAA imply delivery of both to an acidic compartment after endocytosis, most likely the lysosome. Delivery of phosphorylated rhGAA to the lysosome is well-documented in the literature and is the basis for ERT with rhGAA (Van der Ploeg et al., J Clin Invest 87, 513-518, 1991; Yang et al., Pediatr Res 43, 374-380, 1998). Any changes imposed upon GAA as a result of fusion to RAP do not seem to affect the stability of the enzyme in the lysosome.

Figures 25A, 25B:
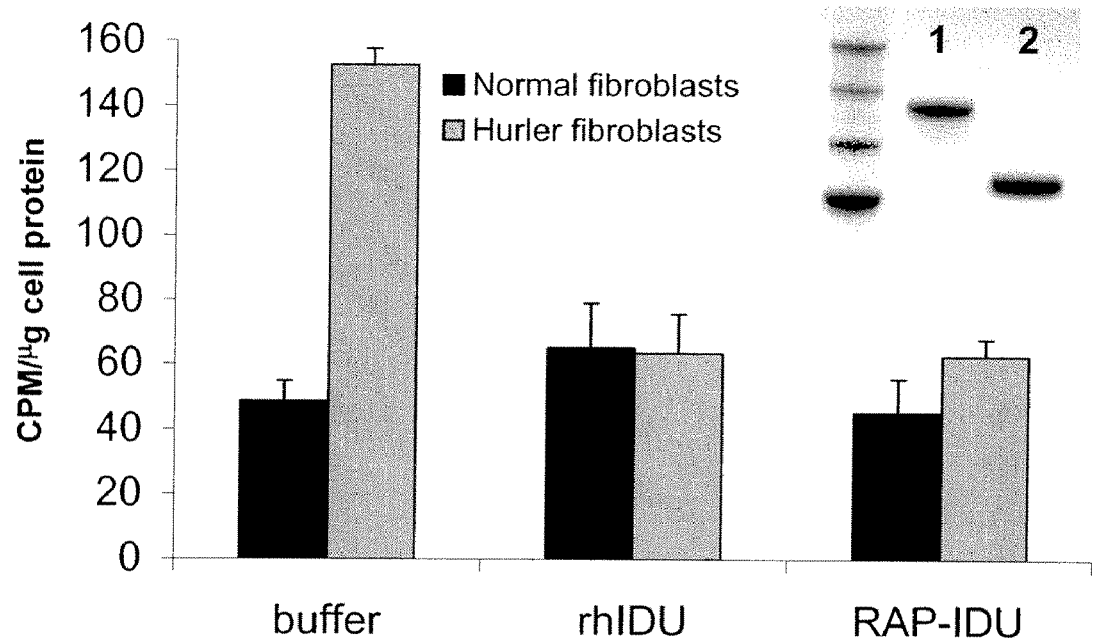
FIG. 25A-25B.

Clearance of lysosomal storage with RAP-IDU—Given the attenuated enzymatic activity of fusion-derived IDU in vitro, experiments were done to determine whether RAP-IDU could prevent the accumulation of glycosaminoglycan in patient fibroblasts. Hurler fibroblasts were grown in sulfate-free medium (S-MEM) in the presence of $^{35}$S-sulfate (Barton and Neufeld, J Biol Chem 246, 7773-7779, 1971). RAP-IDU, rhIDU or buffer was included in the growth medium at a concentration of 5 nM. The purities of the RAP-IDU and rhIDU test materials were confirmed by SDS-PAGE (FIG. 25B (inset)). Stored $^{35}$S-glycosaminoglycan was measured 48 hours later and normalized to total protein concentration. Total radioactivity per sample ranged from 4,000 to 20,000 cpm; total protein concentrations did not vary significantly between samples. Both RAP-IDU and IDU prevented $^{35}$S-GAG storage to the same extent, indicating that fusion-derived IDU is competent to digest the natural substrate.

Example 11

Megalin Mediates Transcytosis Across the Blood Brain Barrier

The present Example describes studies performed using tight monolayers of MDCK cells in Transwell plates as a model system for transcytosis. This model was employed to demonstrate that megalin rather than LRP1 mediates transcytosis of RAP. MDCK cells had been transfected with mini-receptors consisting of the fourth ligand binding and transmembrane domains of LRP I with either the C-terminal cytoplasmic tail of LRP1 (mLRP/LRPTmT=LRPt) or of megalin (mLRP/LRPTmMegT=MEGt). The system takes advantage of the superior expression levels of these minireceptors as well as the modularity of different LRP receptor domains. The premises of the system are that the LRP1 ecto-domain and the megalin ecto-domain bind RAP similarly, and that megalin tail-mediated trafficking in MDCK is similar to that in other epithelial cell layers, including the brain capillary endothelium.

In Vitro Transport Assays

Stably transfected MDCK cells and the parent MDCK line were obtained from Dr. Maria-Paz Marzolo (Santiago, Chile). LRPt is distributed basolaterally as shown by indirect immunofluorescence with an anti-HA antibody, and MEGt localizes to the apical surface of the transfected MDCK cells (Marzolo et al., Traffic, 4(4):273-88, 2003). Cells were plated on the surface of polyacetate membrane inserts of the Transwell system (Costar, Cambridge, Mass.) with a uniform pore size of 0.4 μm. Cells were seeded at a density of $2 \times 10^5$ cell/ml and cultured in DMEM supplemented with 10% FBS with medium change every three days. Cells were kept in a 5% $CO_2$ incubator at 37° C. Transcytosis studies were performed in triplicates of Transwells of six groups for either apical-to-basolateral or basolateral-to-apical transport, with or without inclusion of 2 μg/ml of excess unlabeled RAP.

Twenty minutes prior to the transport assay, the Transwell insert and its supporting endothelial cell monolayer were equilibrated in the transport buffer (Hank's balanced salt solution with 25 mM HEPES and 0.1% albumin) at 37° C. Transport was initiated by addition of $^{125}$I-RAP (1 μCi/ml) and $^{99m}$Tc-albumin (2 μCi/ml) to the upper or lower chambers at time-zero. The plate was kept at 37° C. with gentle mixing at about 130 rpm during the entire procedure. At 5, 10, 15, 20, 30, 40, 50, and 60 min, 10 μl of sample was collected in the lower chamber of each well. At 60 min, solution in the upper and lower chambers was transferred to separate test tubes at 4° C. The radioactivity of $^{125}$I- and $^{99m}$Tc-albumin was measured simultaneously in a gamma counter with a dual-channel program. The amount of intact $^{125}$I-RAP and $^{99m}$Tc-albumin after transport was measured by acid precipitation. HPLC analysis was performed on selected samples, with a linear gradient of 10-90% acetonitrile in 0.1% trifluoroacetic acid over 40 min, and 1 ml fractions were collected.

At the time of study, the TEER of the confluent monolayers, a parameter indicating of the tightness of the barrier, was 757 Ω/cm2 for native MDCK, 364 Ω/cm2 for LRPt-transfected MDCK, and 370 Ω/cm2 for MEGt-transfected MDCK.

The transcytosis assays were initiated by addition of $^{125}$I-RAP and the paracellular permeability marker $^{99m}$Tc-albumin simultaneously at time-zero. At the end of the study (60 minutes), intact $^{125}$I-RAP accounted for 99% of the acid precipitable radioactivity in the donor chamber and 91% of that in the acceptor chamber. This indicates that the majority of radioactivity measured represented intact $^{125}$I-RAP. Extending the study period to 120 minutes did not change the percentage of intact $^{125}$I-RAP or the flux rate.

For apical-to-basolateral flux, in non-transfected MDCK cells, the permeability coefficient of $^{125}$I-RAP after 60 min of transport was $5.1 \pm 0.8 \times 10^{-6}$ cm/sec. By contrast, in MDCK cells transfected with MEGt, the permeability coefficient of $^{125}$I-RAP was $18.1 \pm 1.2 \times 10^{-6}$ cm/sec. Surprisingly, in MDCK cells transfected with LRPt, there was no significant flux. In all groups, $^{99m}$Tc-albumin also had no significant flux.

Addition of excess unlabeled RAP at 2 μg/ml significantly decreased the permeability coefficient of $^{125}$I-RAP in MEGt-transfected cells ($6.3 \pm 0.4 \times 10^{-6}$ cm/sec) [F(1,12)=86.1, p<0.0001]. Whereas the non-transfected cells had no, significant flux after addition of excess RAP, the difference between the groups with and without excess RAP was also statistically significant [F(1,11)=24, p<0.0005]. Thus, the results support the presence of a saturable transport system for RAP at the apical surface and the essential role of megalin in the transport process.

Figure 18:
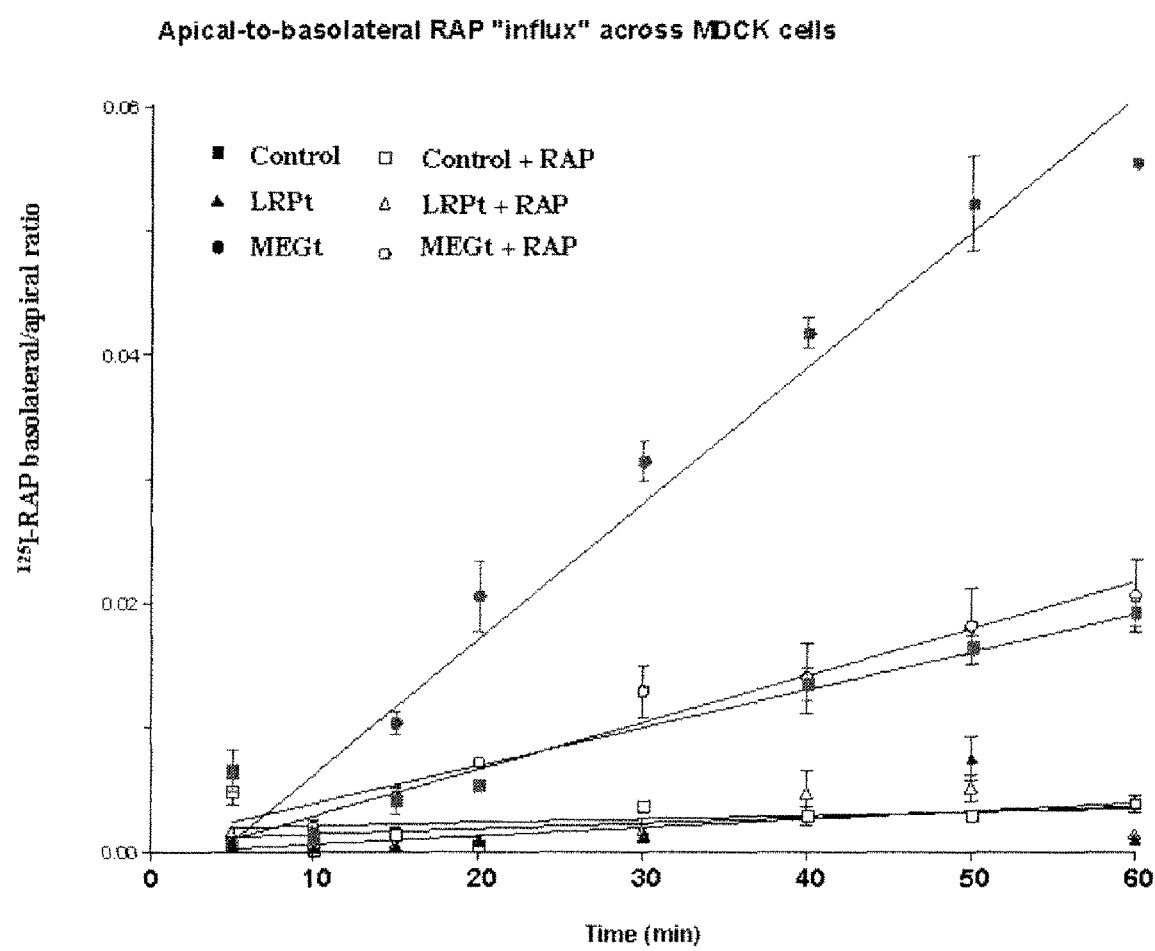
FIG. 18. Transport of $^{125}$I-RAP in MDCK cells showing basolateral-to-apical flux.

For basolateral-to-apical flux, the transport of $^{125}$I-RAP in all three groups was not significantly higher than that of $^{99m}$Tc-albumin, the marker for paracellular permeability (FIG. 18). For MDCK cells stably transfected with MEGt, the apical-to-basolateral permeability coefficient of $^{125}$I-RAP was 460 times higher than the basolateral-to-apical permeability coefficient. Taken together, these results support megalin tail-mediated transcytosis of RAP.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. A conjugate comprising a receptor associated protein (RAP) polypeptide and a therapeutic or diagnostic/investigational agent, wherein the RAP polypeptide consists of an amino acid sequence at least 80% identical to amino acids 221-323 of RAP (SEQ ID NO: 1).

2. The conjugate of claim 1, wherein the therapeutic agent is a chemotherapeutic agent.

3. The conjugate of claim 2, wherein the chemotherapeutic agent is selected from the group consisting of an alkylating agent, an alkaloid, an anti-metabolite, an antibiotic, and an anti-proliferative agent.

4. The conjugate of claim 3, wherein the chemotherapeutic agent is selected from the group consisting of Mechlorethamine hydrochloride, Cyclophosphamide, Ifosfamide, Chlorambucil, Melphalan, Busulfan, Thiotepa (Triethylenethiophosphoramide), Carmustine, Lomustine, Streptozocin, Vincristine, Vinblastine, Paclitaxel, Methotrexate, Mercaptopurine, Thioguanine, Fluorouracil, Cytarabine, Azacitidine, Dactinomycin, Doxorubicin, Daunorubicin, Idarubicin, Bleomycin, Picamycin, Mitomycin, Hydroxyurea, Procarbazine, Dacarbazine, Cisplatin, Carboplatin, Asparaginase, Etoposide, Amsarcrine, Mitotane, and Mitoxantrone.

5. The conjugate of claim 1, wherein the therapeutic agent is a neurotrophic factor.

6. The conjugate of claim 5, wherein the therapeutic agent is a neurotrophic factor selected from the group consisting of Glial-Derived Neurotrophic Factor, Nerve Growth Factor, Brain-Derived Neurotrophic Factor, Neurotrophin-3, Neurotrophin-4/5, aFGF, bFGF, CNTF, Leukemia Inhibitory Factor, Cardiotrophin-1, TGFβ, BMPs, GDFs, Neurturin, Artemin, Persephin, EGF, TGFα, Neuregulins, IGF-1, IGF-2, ADNF and PDGF.

7. The conjugate of claim 6, wherein the therapeutic agent is brain-derived neurotrophic factor (BDNF).

8. The conjugate of claim 2, wherein the agent is a diagnostic/investigational agent and comprises a detectable label.

9. The conjugate of claim 1, wherein the agent is conjugated to the RAP amino acid sequence via covalent bonding.

10. The conjugate of claim 1, wherein the agent is conjugated to the RAP amino acid sequence via a peptide linker.

11. The conjugate of claim 1, wherein said RAP polypeptide is further missing the endoplasmic reticulum retention signal at residues 320-323 of SEQ ID NO: 1.

12. The conjugate of claim 1, wherein the conjugate is a fusion protein of the RAP polypeptide and a therapeutic agent.

13. A sterile composition comprising the conjugate of any one of claim 1, 2, 3 or 5 and a pharmaceutically acceptable carrier.

* * * * *